US006770267B2

(12) United States Patent
Daluge et al.

(10) Patent No.: US 6,770,267 B2
(45) Date of Patent: Aug. 3, 2004

(54) METHODS OF TREATING PERIODONTAL DISEASE

(75) Inventors: Susan Mary Daluge, Chapel Hill, NC (US); Cynthia Holder Jurgensen, Raleigh, NC (US); Michael Tolar Martin, Durham, NC (US); Martin Howard Osterhout, Raleigh, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 325 days.

(21) Appl. No.: 10/106,772

(22) Filed: Mar. 26, 2002

(65) Prior Publication Data

US 2003/0032804 A1 Feb. 13, 2003

Related U.S. Application Data

(62) Division of application No. 09/762,559, filed as application No. PCT/EP99/05814 on Aug. 11, 1999.

(30) Foreign Application Priority Data

Aug. 13, 1998 (GB) .............................................. 9817623

(51) Int. Cl.[7] .............................. A61K 7/16; A61K 7/22
(52) U.S. Cl. ........................................... 424/54; 424/49
(58) Field of Search ............................................ 424/54

(56) References Cited

U.S. PATENT DOCUMENTS

| 4,442,125 A | * | 4/1984 | Thiele ........................ 424/318 |
| 4,879,296 A | | 11/1989 | Daluge et al. |
| 4,968,672 A | | 11/1990 | Jacobson et al. |
| 5,015,647 A | | 5/1991 | Daluge et al. |
| 5,395,831 A | | 3/1995 | Gemmill et al. |
| 5,496,814 A | | 3/1996 | Gemmill et al. |
| 5,712,102 A | * | 1/1998 | Darveau .................... 435/7.32 |
| 5,714,494 A | | 2/1998 | Connell et al. |
| 5,840,302 A | * | 11/1998 | Darveau .................. 424/150.1 |
| 6,117,878 A | | 9/2000 | Linden et al. |
| 6,214,992 B1 | | 4/2001 | Gebert et al. |

FOREIGN PATENT DOCUMENTS

| EP | 0 369 744 | 5/1990 |
| EP | 0 389 282 | 9/1990 |
| EP | 0 590 919 | 4/1994 |
| EP | 0 812 844 | 12/1997 |
| WO | WO02 03721 | 12/1986 |
| WO | WO92 09203 | 6/1992 |
| WO | WO93 23401 | 11/1993 |
| WO | WO94 03456 | 2/1994 |
| WO | WO96 04280 | 2/1996 |
| WO | WO 97/34616 | 9/1997 |
| WO | WO97 34616 | 9/1997 |
| WO | WO98 35966 | 8/1998 |
| WO | WO 99 43673 | 2/1999 |
| WO | WO00 09507 | 2/2000 |
| WO | WO 01 45703 A1 | 6/2001 |

OTHER PUBLICATIONS

Mole N. Kennel–de March A, et al. "High levels of soluble intercellular adhesion molecule–1 (ICAM–1) in crevicular fluid of periodontitis patients with plaque" Journal of Clinical Periodontology 25(9):754–8, Sep. 1998.
Del Castillo LF., et al. "Immunohistochemical localization of very late activation integrins in healthy and diseased human gingiva" Journal of Periodontal Research, 31(1):36–42, Jan. 1996.
Walsh, LJ, et al. "Relationship between mast cell degranulation and inflammation in the oral cavity" Journal of Oral Pathology & Medicine, 24(6):266–72, Jul. 1995.
Gemmell, E., et al. Cellular adhesion molecules on periodontal lymphocytes Australian Dental Journal, 40(2):129–9–34, Apr. 1995.
Tonetti, MS., et al. "Vascular adhesion molecules and initial development of inflammation in clinically healthy human keratinized mucosa around teeth and osseointegrated implants" Journal of Periodontal Research, 29(6):386–92, Nov. 1994.
Takahashi, K., et al. "Role of cytokine in the induction of adhesion molecules on cultured human gingival fibroblasts" Journal of Periodontology, 65(3):230–5, Mar. 1994.
Gemmell, E., et al. "Adhesion molecule expression in chronic inflammatory periodontal disease tissue" Journal of Periodontal Research, 29(1):46–53, Jan. 1994.
Jurgensen et al., "Deazaadensine Inhibits Leukocyte Adhesion and Icam–1 Biosynthesis in Tumor Necrosis Factor–Stimulated Human Endothelial Cells,"*Journal of Immunology*, vol. 144, No. 2, pp. 653–661, (Jan. 15, 1990).
Yong–Chul Kim et al., "Anilide Derivatives of an 8–Phenylxanthine Carboxylic Congener are Highly Potent and Selective Antagonists at Human A2B Adenosine Receptors, "*J. Med. Chem* , vol. 43, pp. 1165–1172 (2000).
Daluge, S., J. Med. Chem., 15:p. 171 (1972).
Nagasawa et al., J. Med. Chem., 15:p. 177 (1972).
Braun, Cardiovascular Research, 41: pp. 395–401 (1999).
Granger, J., Leukocyte Biology, 55: p. 662 (May, 1994).
Harlan, "Adhesion: Its Role in Inflammatory Disease", pp. 117–159, (1990).
Korthius, Ronald J., et al., Journal of Critical Care, vol 9(1), Mar. 1994, pp. 47–71.
Seymour GJ., et al. "Immunopathogenesis of chronic inflammatory periodontal disease: cellular and molecular mechanisms" (Review) (60 refs), Journal of Periodontal Research, 28(6 Pt 2):478–86, Nov. 1993.
Nylander, K., et al. "Expression of the endothelial leukocyte adhesion molecule–1 (ELAM–1) on endothelial cells in experimental gingivits in humans" Journal of Periodontology, 64(5):355–7, May 1993.

(List continued on next page.)

*Primary Examiner*—Shep K. Rose
(74) *Attorney, Agent, or Firm*—Lorie Ann Morgan

(57) ABSTRACT

The present invention relates to methods of treating periodontal disease.

7 Claims, No Drawings

OTHER PUBLICATIONS

Tajima, M., et al. "The detection of a mutation of CD18 gene in bovine leukocyte adhesion deficiency (BLAD)" Journal of Veterinary Medical Science, 55(1):145–6, Feb. 1993.

Nylander, K., "The ELAM–1 ligand sialosyl–Le(X) is present on Langerhans cells isolated from stratified epithelium" Experimental Dermatology, 1(5):236–41, Dec. 1992.

Moughal, NA, et al. "Endothelial cell leukocyte adhesion molecule–1 (ELAM–1) and intercellular adhesion molecule–1 (ICAM–1) expression in gingival tissue during health and experimentally–induced gingivitic " Journal of Periodontal Research, 27(6)623–30, Nov. 1992.

Crawford, JM, et al. "Distribution of ICMA–1, LFA–3 and HLA–DR in healthy and diseased gingival tissues" Journal of Periodontal Research, 27(4 Pt 1):291–8, Jul. 1992.

Deslaurier, M., et al. "Epitope mapping of hemagglutinating adhesion HA–Ag2 of Bacteroides (Porphyromonas) gingivalis" Infection & Immunity, 60(7):2791–9, Jul. 1992.

Watanabe, K., et al. "Generalized juvenile periodontitis in a thirteen–year–old child " ASCD Journal of Dentistry for Children, 58(5):390–5, Sep.–Oct. 1991.

Kinane, DF., et al. "Immunocytochemical characterization of cellular infiltrate, related endothelial changes and determination of GCF acute–phase proteins during human experimental gingivitis" Journal of Periodontal Research, 26(3 Pt 2):286–8, May. 1991.

* cited by examiner

METHODS OF TREATING PERIODONTAL DISEASE

CROSS-REFERENCES TO RELATED APPLICATIONS

This Application is a divisional of U.S. patent application Ser. No. 09/762,559, filed Feb. 9, 2001, which was filed pursuant to 35 U.S.C. §371 as a United States National Phase Application of International Application No. PCT/EP99/05814, filed Aug. 11, 1999 and published as WO 00/09507, Feb. 14, 2000, which claims priority to Great Britain Application No. 9817623.3, filed Aug. 13, 1998.

FIELD OF THE INVENTION

The present invention relates to glycol derivatives of xanthines, processes for their preparation, pharmaceutical formulations comprising them, and their use in medicine, particularly in the treatment and prophylaxis of inflammatory conditions, immune disorders, septic shock, circulatory disorders and gastrointestinal inflammation, infection or damage.

BACKGROUND OF THE INVENTION

Leukocyte adhesion to vascular endothelium plays a critical role in the pathogenesis of various diseases. This adhesion is an early and requisite step in the migration of leukocytes into surrounding tissues, and is essential for the initiation and perpetuation of inflammatory and immune disorders. The adhesion process is dependent on the induction or upregulation of adhesion molecules on the endothelium, thereby representing an important target for diseases in which leukocytes contribute significantly to vascular and tissue damage.

The discovery and development of small molecules which specifically block or inhibit the adhesive interactions of leukocytes and the endothelium is an attractive area of therapeutic intervention, particularly for inflammatory diseases. Current antiiflammatory treatments have limited efficacy, often accompanied by severe side-effects. We here describe the discovery of a series of complex esters and amides of selected phenyl xanthine derivatives which, at low concentrations, inhibits the expression of adhesion molecules on cultured human umbilical vein endothelial cells. These compounds are therefore indicated for the treatment of inflammatory conditions, immune disorders, infectious diseases, circulatory disorders, and a number of other conditions in which the adhesion between leukocytes and endothelium plays a major role.

PCT application publication No. WO 9604280 describes compounds of formula:

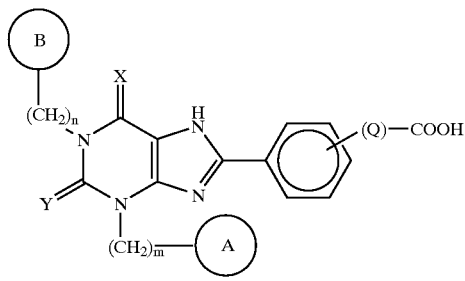

Wherein m and n are independently integers from 0 to 10;
X and Y are independently oxygen or sulphur;
(—Q—) is (—$CH_2$—)$_p$ or (—CH=CH—)$_p$ where p is an integer of from 1 to 4; and A and B are independently methyl, branched $C_{3-6}$alkyl, $C_{3-8}$cycloalkyl or $C_{3-8}$cycloalkenyl;

and salts, solvates and pharmaceutically acceptable esters and amides thereof; and their use in treatment of inflammatory diseases, immune disorders, septic shock, circulatory disorders and gastrointestinal inflammation, infection or damage.

SUMMARY OF THE INVENTION

Accordingly the present invention provides a compound of formula (I):

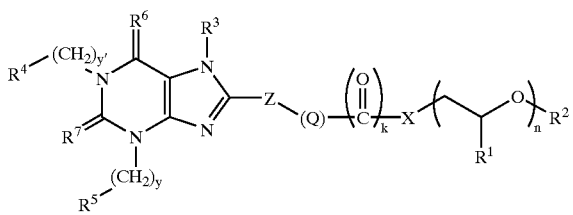

wherein
Z represents a 5 or 6 membered cycloalkyl, aryl, substituted cycloalkyl, or substituted aryl, said cycloalkyl, aryl, substituted cycloalkyl, or substituted aryl optionally containing one or more heteroatoms selected from O, N or S;

$R^1$ represents hydrogen or methyl;

$R^2$ represents hydrogen, $C_{1-12}$alkyl, aryl, or aralkyl;

k represents 0 or 1 n represents an integer of 1 to 50;

X represents —O—, —N(H), —N($C_{1-6}$alkyl)—, —N($C_{3-8}$ cycloalkyl)—, —N($C_{1-8}$alkyl)($C_{3-8}$ cycloalkyl), —N[($CH_2CH_2O$)$_m$($C_{1-12}$alkyl, aryl, or aralkyl)]—, —$CH_2O$—, —$CH_2NH$—, —$CH_2N$($C_{1-6}$ alkyl)—, —$CH_2N$($C_{3-8}$cycloalkyl), or —$C_{1-12}$alkyl—, m represents 0–12

Q represents (—$CH_2$)$_p$, (—CH=CH—)$_p$, (—C≡C—)$_p$, (—(O)$_{p1}CH_2$—)$_p$ or (—$CH_2$(O)$_{p1}$)$_p$ where p and p$^1$ independently represent an integer of from 0 to 4;

y and y' independently represent integers from 0 to 10;

$R^3$ represents H, straight or branched $C_{1-12}$alkyl (optionally substituted by phenyl, —CO-phenyl, CN, —CO($C_{1-3}$)alkyl, —$CO_2$($C_{1-3}$)alkyl, or containing one or more O atoms in the alkyl chain); $C_{1-6}$straight or branched alkenyl (optionally substituted by phenyl, —CO-phenyl, CN, —CO($C_{1-3}$)alkyl, —$CO_2$($C_{1-3}$) alkyl, or containing one or more O atoms in the alkyl chain); $C_{1-6}$ straight or branched alkynyl or a group —$C_{1-3}$alkyl —$NR^8R^9$ wherein $R^8$ and $R^9$ are independently H, $C_{1-3}$alkyl or together form a 5 or 6 membered heterocyclic group, optionally containing other heteroatoms selected from O, N or S;

$R^4$ and $R^5$ independently represent
$C_{3-8}$cycloalkyl
straight chain or branched $C_{1-6}$alkyl
hydrogen
straight or branched $C_{2-6}$alkenyl
aryl or substituted aryl;
heterocyclic group or subsituted heterocyclic group, including heteroaryl and substituted heteroaryl groups;

$R^6$ and $R^7$ independently represent O or S;
with the proviso that when
 y and y' both represent 1,
 k represents 1,
 $p^1$ represents zero,
 $R^2$ represents H or Me,
 $R^3$ represents H,
 X represents O or NH, and
 Z represents phenyl
$R^4$ and $R^5$ do not both represent cyclohexyl;
or a solvate thereof.

The present invention also provides a compound of formula (Ia):

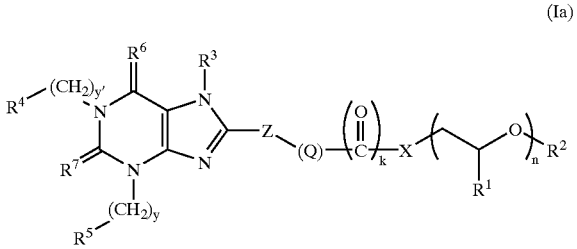

(Ia)

wherein
Z represents a 5 or 6 membered cycloalkyl, aryl, substituted cycloalkyl, or substituted aryl, said cycloalkyl, aryl, substituted cycloalkyl, or substituted aryl optionally containing one or more heteroatoms selected from O, N or S;
$R^1$ represents hydrogen or methyl;
$R^2$ represents hydrogen, $C_{1-12}$alkyl, aryl, or aralkyl;
k represents 0 or 1
n represents an integer of 1 to 50;
X represents —O—, —N(H)—, —N($C_{1-6}$alkyl)—, —N($C_{3-8}$cycloalkyl)—, —N[($CH_2CH_2O)_m$($C_{1-12}$alkyl aryl, or aralkyl)]—, —$CH_2$O—, —$CH_2$NH—, —$CH_2$N($C_{1-6}$alkyl)—, —$CH_2$N($C_{3-8}$cycloalkyl)—, or —$C_{1-12}$alkyl—,
m represents 0–12
Q represents $(—CH_2)_p$, $(—CH=CH—)_p$, $(—C≡C—)_p$, $(—O)_{p1}CH2—)_p$ or $(CH_2(O)_{p1})_p$ where p and $p^1$ independently represent an integer of from 0 to 4;
y and y' independently represent integers from 0 to 10;
$R^3$ represents H, straight or branched $C_{1-12}$alkyl (optionally substituted by phenyl, —CO-phenyl, CN, —CH($C_{1-3}$)alkyl, $CO_2$($C_{1-3}$)alkyl, or containing one or more O atoms in the alkyl chain); $C_{1-6}$straight or branched alkenyl, $C_{1-6}$straight or branched alkynyl or a group —$C_{1-3}$alkyl —$NR^8R^9$
 wherein $R^8$ and $R^9$ are independently H, $C_{1-3}$alkyl or together form a 5 or 6 membered heterocyclic group, optionally containing other heteroatoms selected from O, N or S;
$R^4$ and $R^5$ independently represent
 $C_{3-8}$cycloalkyl
 straight chain or branched $C_{1-6}$alkyl
 hydrogen
 straight or branched $C_{2-6}$alkenyl
 aryl or substituted aryl;
 heterocyclic group or substituted heterocyclic group, including heteroaryl and substituted heteroaryl groups;
$R^6$ and $R^7$ independently represent O or S;
with the proviso that when
 y and y' both represent 1,
 k represents 1,
 $p^1$ represents zero,
 $R^3$ represents H,
 X represents O or NH, and
 Z represents phenyl
$R^4$ and $R^5$ do not both represent cyclohexyl;
or a solvate thereof.

DETAILED DESCRIPTION OF THE INVENTION

As used herein, the term "aryl" refers to a carbocyclic group having 6–14 carbon atoms with at least one aromatic ring (e.g., phenyl or biphenyl) or multiple condensed rings in which at least one ring is aromatic, (e.g., 1,2,3,4,-tetrahydronaphthyl, naphthyl, anthryl, or phenanthryl).

As used herein, the term "substituted aryl" refers to aryl optionally substituted with one or more functional groups, e.g., halogen, lower alkyl, lower alkoxyl lower alkylthio, trifluoromethyl, amino, amido, carboxyl, hydroxyl, aryl, aryloxy, heterocycle, hetroaryl, substituted heteroaryl, nitro, cyano, alkylthio, thiol, sulfamido and the like.

As used herein, the term "aralkyl" refers to a $C_{1-12}$alkyl that may be a straight or a branched alkyl group that is substituted by an aryl or substituted aryl group.

As used herein, the term "substituted alkyl" or "substituted cycloalkyl" refers to alkyl or cycloalkyl optionally substituted with one or more functional groups, e.g., halogen, lower alkyl, lower alkoxy, lower alkylthio, trifluoromethyl, amino, amido, carboxyl, hydroxyl, aryl, aryloxy, heterocycle, hetroaryl, substituted heteroaryl, nitro, cyano, alkylthio, thiol, sulfamido and the like.

As used herein, the term "heterocylic group" refers to a saturated, unsaturated, or aromatic carbocyclic group having up to seven members in a single ring (e.g. imidazolidinyl, piperidyl, piperazinyl, pyrrolidinyl, morpholinyl, pyridyl, pyridazinyl, pyrimidinyl, pyrazinyl, pyrrolyl, pyrazolyl, imidazolyl, pyranyl, furyl, thienyl, oxazolyl, isoxazolyl, oxadiazolyl, thiazylyl, thiadiazolyl, triazolyl or tetrazolyl.) or multiple condensed rings (e.g. naphthpyridyl, qunoxalyl, indolizinyl or benzo[b]thienyl) and having from one to three heteroatoms, such as N, O, or S, within the ring. The heterocydic group can optionally be unsubstituted or substituted (i.e., a "substituted heterocydic group") with e.g. halogen, lower alkyl, lower alkoxy, lower alkylthio, trifluoromethyl, amino, amido, carboxyl, hydroxyl, aryl, aryloxy, heterocyclic group, hetroaryl, substituted heteroaryl, nitro, cyano, alkylthio, thiol, sulfamido and the like.

As used herein, the term "heteroaryl" refers to a heterocyclic group in which at least one heterocyclic ring is aromatic.

As used herein, the term "substituted heteroaryl" refers to a heterocyclic group optionally substituted with one or more substituents including halogen, lower alkyl, lower alkoxy, lower alkylthio, trifluoromethyl, amino, amido, carboxyl, hydroxyl, aryl, aryloxy, heterocycle, hetroaryl, substituted heteroaryl, nitro, cyano, alkylthio, thiol, sulfamido and the like.

The term "$C_{1-12}$alkyl" as used herein represents straight or branched alkyl groups containing the indicated number of carbon atoms.

The term "$C_{2-6}$alkenyl" refers to straight or branched chain alkenyl groups containing 2 to 6 carbon atoms for example propenylene.

The term "$C_{3-8}$cycloalkyl" includes cyclic groups containing 3–8 carbon atoms such as cyclopropane, cyclobutane, cyclopentane, cyclohexane, cycloheptane and cyclooctane and includes bridged cycloalkyl groups, for example norbornyl.

In one particular aspect, the invention provides a compound of formula (I) or (Ia) wherein $R^4$ and $R^5$ independently represent:

$C_{3-8}$cycloalkyl;

straight chain or branched $C_{1-6}$alkyl;

hydrogen; or, straight or branched $C_{2-6}$akenyl.

In another aspect, the invention provides a compound of formula (I) or (Ia) wherein $R^4$ and $R^5$ independently represent aryl or substituted aryl.

In another aspect, the invention provides a compound of formula (I) or (Ia) wherein $R^4$ and $R^5$ independently represent a heterocyclic group or substituted heterocyclic group, including hetemoaryl and substituted heteroaryl groups.

In another aspect, the invention provides a compound of formula (I) or (Ia) wherein $R^3$ represents $C_{1-3}$alkyl$NR^8R^9$ and $R^8$ and $R^9$ independently represent H or $C_{1-3}$alkyl.

In another aspect, the invention provides a compound of formula (I) or (Ia) wherein $R^3$ represents $C_{1-3}$alkyl$NR^8R^9$ and $R^8$ and $R^9$ together form a 5 or 6 membered heterocyclic group, optionally containing other heteroatoms selected from O, N or S.

In another aspect, the invention provides a compound of formula (I) or (Ia) wherein Z represents a 5 or 6 membered cycloalkyl, aryl, substituted cycloalkyl or substituted aryl containing no heteroatoms.

In another aspect, the invention provides a compound of formula (I) or (Ia) wherein Z represents a 5 or 6 membered cycloalkyl, aryl, substituted cycloalkyl or substituted aryl containing from one to three heteroatoms independently selected from O, N or S.

In one preferred embodiment, the compounds of formula I are defined where Z represents a phenyl ring, thiophene ring or pyridine ring, more preferably phenyl.

Preferably the grouping

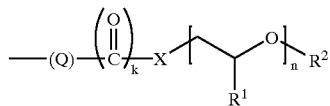

may be attached to Z in any suitable position. When Z is phenyl, preferably this group is attached to the phenyl ring in the para position.

In one preferred embodiment, the compounds of formula I are defined where $R^1$ is H.

In another preferred embodiment, the compounds of formula I are defined where $R_2$ is methyl or ethyl.

In one preferred embodiment, the compounds of formula I are defined where k is 1.

Another preferred set of compounds within formula I are defined where n is from 8 to 20, more preferably from 8 to 15. However in certain embodiments of the present invention, such as wherein $R^3$ is other than H, n may preferably be shorter than 8 to 20, such as 5 to 20. Similarly, when k is 0, n may preferably be shorter than 8 to 20, such as 5–20.

Still another preferred set of compounds within formula I is defined where X is —O—, —N(H)—, or —N(CH$_3$)—.

In one preferred embodiment, the compounds of formula I are defined where Q is (CH=CH—)$_p$. More preferably, compounds are defined where Q is (—CH=CH—)$_p$ and p is 1.

One preferred set of compounds of formula I are defined where y and y' are the same. More preferably, compounds of formula I are defined where y and y' are 1.

In another preferred embodiment, the compounds of formula I are defined where $R_3$ is methyl.

Another set of preferred compounds of formula I are defined where $R^4$ and $R^5$ are independently selected from the group consisting of $C_{1-6}$alkyl, $C_{3-8}$cycloalkyl and aryl. More preferably, $R^4$ and $R^5$ are independently selected from cyclobutyl, cyclopentyl, cyclohexyl, propyl, butyl, isopropyl, isobutyl, and phenyl. Although one preferred set of compounds is defined where $R^4$ and $R^5$ are different, another preferred set of compounds is defined where $R^4$ and $R^5$ are the same.

In another preferred embodiment, $R^6$ and $R^7$ are the same. More preferably, both $R^6$ and $R^7$ are O.

According to a further aspect, the present invention provides a compound of formula (I) or (Ia) as defined above wherein X is —O— and $R^1$ is H; of these, compounds wherein n is an integer of 8 to 20 are preferred, and those wherein n is an integer of 8 to 15 are more preferred.

It is to be understood that the present invention covers all combinations of particular and preferred groups described hereinabove.

The invention also includes mixtures of compounds of formula (I) or (Ia) in any ratio, for example wherein n varies within the same sample.

Particularly preferred compounds of the invention include:

(E)-4-(1,3-bis(benzyl)-1,2,3,6-tetrahydro-2,6-dioxo-9H-purin-8-yl)cinnamic Acid Nonaethylene Glycol Methyl Ether Ester;

(E)-4-[1,3-Bis(cyclohexylmethyl)-1,2,3,6-tetrahydro-2,6-dioxo-9H-purin-8-yl]cinnamic Acid Nonaethylene Glycol Methyl Ether Ester;

(E)-4-(1,3-bis(cyclopentylmethyl)-1,2,3,6-tetrahydro-2,6-dioxo-9H-purin-8-yl)cinnamic Acid Nonaethylene Glycol Methyl Ether Ester;

(E)-4-(1,3-bis(propyl)-1,2,3,6-tetrahydro-2,6-dioxo-9H-purin-8-yl)cinnamic Acid Nonaethylene Glycol Methyl Ether Ester;

(E)-4-(1,3-bis(cyclopropylmethyl)-1,2,3,6-tetrahydro-2,6-dioxo-9H-purin-8-yl)cinnamic Acid Nonaethylene Glycol Methyl Ether Ester;

(E)-3-((1-propyl-3-benzyl)-1,2,3,6-tetrahydro-2,6-dioxo-9H-purin-8-yl)cinnamic Acid Nonaethylene Glycol Methyl Ether Ester;

(E)-4-(1,3-bis(cycloheptylmethyl)-1,2,3,6-tetrahydro-2,6-dioxo-9H-purin-8-yl)cinnamic Acid Nonaethylene Glycol Methyl Ether Ester;

(E)-4-(1,3-bis(cyclohexylethyl)-1,2,3,6-tetrahydro-2,6-dioxo-9H-purin-8-yl)cinnamic Acid Nonaethylene Glycol Methyl Ether Ester;

(E)-4-(1,3-bis(phenyl)-1,2,3,6-tetrahydro-2,6-dioxo-9H-purin-8-yl)cinnamic Acid Nonaethylene Glycol Methyl Ether Ester;

(E)-4-(1,3-bis(2-methyl-propyl)-1,2,3,6-tetrahydro-2,6-dioxo-9H-purin-8-yl)cinnamic Acid Nonaethylene Glycol Methyl Ether Ester;

(E)-4-((1-propyl-3-cyclohexylmethyl)-1,2,3,6-tetrahydro-2,6-dioxo-9H-purin-8-yl)cinnamic Acid Nonaethylene Glycol Methyl Ether Ester;

(E)-4-(1,3-bis(bicyclo(2.2.1)hept-2-ylmethyl)-1,2,3,6-tetrahydro-2,6-dioxo-9H-purin-8-yl)cinnamic Acid Nonaethylene Glycol Methyl Ether Ester;

(E)-4-(1-cyclohexylmethyl-3-butyl)-1,2,3,6-tetrahydro-2,6-dioxo-9H-purin-8-yl)cinnamic Acid Nonaethylene Glycol Methyl Ether Ester;

(E)-4-((1-cyclohexylmethyl-3-propyl)-1,2,3,6-tetrahydro-2,6-dioxo-9H-purin-8-yl)cinnamic Acid Nonaethylene Glycol Methyl Ether Ester; (E)-4-(1,3-bis(benzyl)-1,2,3,6-tetrahydro-2-thioxooxo-9H-purin-8-yl)cinnamic Acid Nonaethylene Glycol Methyl Ether Ester;

(E)-4-(1-methyl-3-(3-cyanobenzyl)-1,2,3,6-tetrahydro-2,6-dioxo-9H-purin-8-yl)cinnamic Acid Nonaethylene Glycol Methyl Ether Ester;

(E)-4-((1,3-bis(3-fluorobenzyl)-1,2,3,6-tetrahydro-2,6-dioxo-9H-purin-8-yl)cinnamic Acid Nonaethylene Glycol Methyl Ether Ester;

(E)-4-((1,3-bis(2-fluorobenzyl)-1,2,3,6-tetrahydro-2,6-dioxo-9H-purin-8-yl)cinnamic Acid Nonaethylene Glycol Methyl Ether Ester;

(E)-4-((1,3-bisphenethyl)-1,2,3,6-tetrahydro-2,6-dioxo-9H-purin-8-yl)cinnamic Acid Nonaethylene Glycol Methyl Ether Ester;

(E)-4-((1-cyclohexylmethyl-3-methyl)-1,2,3,6-tetrahydro-2,6-dioxo-9H-purin-8-yl)cinnamic Acid Nonaethylene Glycol Methyl Ether Ester;

(E)-4-((1-H-3-(2-methyl-propyl)-1,2,3,6-tetrahydro-2,6-dioxo-9H-purin-8-yl)cinnamic Acid Nonaethylene Glycol Methyl Ether Ester;

(E)-4-(1,3-bis(4-fluorobenzyl)-1,2,3,6-tetrahydro-2,6-dioxo-9H-purin-8-yl)cinnamic Acid Nonaethylene Glycol Methyl Ether Ester;

(E)-4-(1,3-bis(cyclohexylmethyl)-1,2,3,6-tetrahydro-2,6-dioxo-9H-purin-8-yl)cinnamic Acid Hexaethylene Glycol dodecyl Ether Ester;

(E)-4-(1,3-bis(cyclobutylmethyl)-1,2,3,6-tetrahydro-2,6-dioxo-9H-purin-8-yl)cinnamic Acid Nonaethylene Glycol Methyl Ether Ester;

(E)-4-(1-methyl-3-cyclohexylmethyl)-1,2,3,6-tetrahydro-2,6-dioxo-9H-purin-8-yl)cinnamic Acid Nonaethylene Glycol Methyl Ether Ester;

(E)-4-(1-methyl-3-isobutyl)-1,2,3,6-tetrahydro-2,6-dioxo-9H-purin-8-yl)cinnamic Acid Nonaethylene Glycol Methyl Ether Ester;

4-(1,3-bis(cyclohexylmethyl)-1,2,3,6-tetrahydro-2,6-dioxo-9H-purin-8-yl)benzoic Acid Nonaethylene Glycol Methyl Ether Ester;

(E)-4-(1,3-bis(cyclohexyl)-1,2,3,6-tetrahydro-2,6-dioxo-9H-purin-8-yl)cinnamic Acid Nonaethylene Glycol Methyl Ether Ester;

(E)-4-(1,3-Bis(cyclohexylmethyl)-1,2,3,6-tetrahydro-2,6-dioxo-9H-purin-8-yl)cinnamic Acid Nonaethylene Glycol Methyl Ether Amide;

(E)-4-(1,3-bis(cyclopentylmethyl)-1,2,3,6-tetrahydroxo-2-thioxo-9H-purin-8-yl)cinnamic Acid Nonaethylene Glycol Methyl Ether Amide;

(E)-4-(1,3-bis(2-methyl-propyl)-1,2,3,6-tetrahydro-2,6-dioxo-9H-purin-8-yl)cinnamic Acid Nonaethylene Glycol Methyl Ether Amide;

(E)-4-((1-cyclohexylmethyl-3-propyl)-1,2,3,6-tetrahydro-2,6-dioxo-9H-purin-8-yl)cinnamic Acid Nonaethylene Glycol Methyl Ether Amide;

4-(1,3-Bis(cyclohexylmethyl)-1,2,3,6-tetrahydro-2,6-dioxo-9H-purin-8-yl)benzoic Acid Nonaethylene Glycol Methyl Ether Amide;

4-(1,3-Bis(cyclohexylmethyl)-1,2,3,6-tetrahydro-2,6-dioxo-9H-purin-8-yl)benzoic Acid-N-methyl-Nonaethylene Glycol Methyl Ether Amide;

(E)-4-(1,3-Bis(cyclohexylmethyl)-2,3,6,7-tetrahydro-2,6-dioxo-7-benzyl-1H-purin-8-yl)cinnamic Acid Nonaethylene Glycol Methyl Ether Ester;

(E)-4-(1,3-Bis(cyclohexylmethyl)-2,3,6,7-tetrahydro-2,6-dioxo-7-(2-oxo-2-phenylethyl)-1H-purin-8-yl)cinnamic Acid Nonaethylene Glycol Methyl Ether Ester;

(E)-4-(1,3-Bis(cyclohexylmethyl)-2,3,6,7-tetrahydro-2,6-dioxo-7-methyl-1H-purin-8-yl)cinnamic Acid Nonaethylene Glycol Methyl Ether Ester;

(E)-4-(1,3-Bis(cyclohexylmethyl)-2,3,6,7-tetrahydro-2,6-dioxo-7-(2-propynyl)-1H-purin-8-yl)cinnamic Acid Nonaethylene Glycol Methyl Ether Ester;

(E)-4-(1,3-Bis(cyclohexylmethyl)-2,3,6,7-tetrahydro-2,6-dioxo-7-(2-oxo-2-methylethyl)-1H-purin-8-yl)cinnamic Acid Nonaethylene Glycol Methyl Ether Ester;

(E)-4-(1,3-Bis(cyclohexylmethyl)-2,3,6,7-tetrahydro-2,6-dioxo-7-(3-morpholinopropyl)-1H-purin-8-yl)cinnamic Acid Nonaethylene Glycol Methyl Ether Ester;

(E)-4-(1,3-Bis(cyclohexylmethyl)-2,3,6,7-tetrahydro-2,6-dioxo-7-ethyl-1H-purin-8-yl)cinnamic Acid Nonaethylene Glycol Methyl Ether Ester;

(E)-4-(1,3-Bis(cyclohexylmethyl)-2,3,6,7-tetrahydro-2,6-dioxo-7-(2-ethoxy-2-oxoethyl)-1H-purin-8yl)cinnamic Acid Nonaethylene Glycol Methyl Ether Ester;

(E)-4-(1,3-Bis(cyclohexylmethyl)-2,3,6,7-tetrahydro-2,6-dioxo-7-(2-methyl-2-propenyl)-1H-purin-8-yl)cinnamic Acid Nonaethylene Glycol Methyl Ether Ester;

(E)-4-(1,3-Bis(cyclohexylmethyl)-2,3,6,7-tetrahydro-2,6-dioxo-7-(cyanomethyl)-1H-purin-8-yl)cinnamic Acid Nonaethylene Glycol Methyl Ether Ester;

4-(1,3-Bis(cyclohexylmethyl)-2,3,6,7-tetrahydro-2,6-dioxo-7-benzyl-1H-purin-8-yl)benzoic Acid Nonaethylene Glycol Methyl Ether Ester;

4-(1,3-Bis(cyclohexylmethyl)-2,3,6,7-tetrahydro-2,6-dioxo-7-methyl-1H-purin-8-yl)benzoic Acid Nonaethylene Glycol Methyl Ether Ester;

4-[(1,3-Bis(cyclohexylmethyl)-2,3,6,7-tetrahydro-2,6-dioxo-7-methyl-1H-purin-8-yl)phenyl]propionic Acid Nonaethylene Glycol Methyl Ether Ester;

(E)-4-(1,3-Bis(cyclohexylmethyl)-2,3,6,7-tetrahydro-2,6-dioxo-7-methyl-1H-purin-8-yl)cinnamic Acid Nonaethylene Glycol Methyl Ether Amide;

(E)-4-(1,3-Bis(cyclohexylmethyl)-2,3,6,7-tetrahydro-2,6-dioxo-7-benzyl-1H-purin-8-yl)cinnamic Acid Nonaethylene Glycol Methyl Ether Amide;

4-(1,3-Bis(cyclohexylmethyl)-2,3,6,7-tetrahydro-2,6-dioxo-7-benzyl-1H-purin-8-yl)benzoic Acid Nonaethylene Glycol Methyl Ether Amide;

4-(1,3-Bis(cyclohexylmethyl)-2,3,6,7-tetrahydro-2,6-dioxo-7-methyl-1H-purin-8-yl)benzoic Acid Nonaethylene Glycol Methyl Ether Amide;

1,3-Bis(cyclohexylmethyl)-8-[4-(2,5,8,11,14,17,20,23,26,29-decaoxatriacont-1-yl)phenyl]-3,7-dihydro-1H-purine-2,6-dione;

(E)-3-[5-[1,3-bis(cyclohexylmethyl)-2,3,6,7-tetrahydro-2,6-dioxo-1H-purin-8-yl]-2-thienyl]-2-propenoic Acid Nonaethylene Glycol Methyl Ether Ester;

6-(1,3-Bis(cyclohexylmethyl)-1,2,3,6-tetrahydro-2,6-dioxo-9H-purin-8-yl)nicotinic Acid Nonaethylene Glycol Methyl Ether Amide;

(E)-3-(1,3-Bis(cyclohexylmethyl)-1,2,3,6-tetrahydro-2,6-dioxo-9H-purin-8-yl)cinnamic Acid N-cyclopropylmethyl Nonaethylene Glycol Methyl Ether Amide;

(E)-4-(1,3-Bis(cyclohexylmethyl)-1,2,3,6-tetrahydro-2,6-dioxo-9H-purin-8-yl)cinnamic Acid Hexaethylene Glycol Benzyl Ether Amide;

(E)-4-[(3-Cyclohexylmethyl)-2,3,6,7-tetrahydro-2,6-dioxo-7-methyl-1H-purin-8-yl]cinnamic Acid Heptaethylene Glycol Methyl Ether Ester;

(E)-4-[(3-Cyclohexylmethyl)-2,3,6,7-tetrahydro-2,6-dioxo-7-methyl-1H-purin-8-yl]cinnamic Acid Nonaethylene Glycol Methyl Ether Ester;

(E)-4-[(3-Cyclohexylmethyl)-2,3,6,7-tetrahydro-2,6-dioxo-1,7-dimethyl-1H-purin-8-yl]cinnamic Acid Nonaethylene Glycol Methyl Ether Ester;

4-[1,3-Bis(cyclohexylmethyl)-1,2,3,6-tetrahydro-2,6-dioxo-9H-purin-8-yl]benzylamine Heptaethylene Glycol Methyl Ether;

4-[1,3-Bis(cyclohexylmethyl)-1,2,3,6-tetrahydro-2,6-dioxo-9H-purin-8-yl]benzylamine N-Heptaethylene Glycol Methyl Ether Hydrochloride;

4-[1,3-Bis(cyclohexylmethyl)-1,2,3,6-tetrahydro-2,6-dioxo-9H-purin-8-yl]benzylamine N-Nonaethylene Glycol Methyl Ether;

1,3-Bis(cyclohexylmethyl)-8-[3,2,5,8,11,14,17,20,23,26,29-decaoxatriacont-1-yl)phenyl]-3,7-dihydro-1H-purine-2,6-dione;

(E)-4-(1,3-Bis(cyclohexylmethyl)-2,3,6,7-tetrahydro-2,6-dioxo-7-methyl-1H-purin-8-yl)cinnamic Acid Heptaethylene Glycol Methyl Ether Ester;

(E)-4-(1,3-Bis(cyclohexylmethyl)-2,3,6,7-tetrahydro-2,6-dioxo-7-methyl-1H-purin-8-yl)cinnamic Acid Pentaethylene Glycol Methyl Ether Ester;

(E)-4-(1,3-Bis(cyclohexylmethyl)-2,3,6,7-tetrahydro-2,6-dioxo-7-propyl-1H-purin-8-yl)cinnamic Acid Nonaethylene Glycol Methyl Ether Ester.

More particularly preferred compounds:

(E)-4-(1,3-bis(benzyl)-1,2,3,6-tetrahydro-2,6-dioxo-9H-purin-8-yl)cinnamic Acid Nonaethylene Glycol Methyl Ether Ester;

(E)-4-[1,3-Bis(cyclohexylmethyl)-1,2,3,6-tetrahydro-2,6-dioxo-9H-purin-8-yl]cinnamic Acid Nonaethylene Glycol Methyl Ether Ester;

(E)-4-(1,3-bis(cyclopentylmethyl)-1,2,3,6-tetrahydro-2,6-dioxo-9H-purin-8-yl)cinnamic Acid Nonaethylene Glycol Methyl Ether Ester;

(E)-4-(1,3-bis(propyl)-1,2,3,6-tetrahydro-2,6-dioxo-9H-purin-8-yl)cinnamic Acid Nonaethylene Glycol Methyl Ether Ester;

(E)-4-(1,3-bis(cycloheptylmethyl)-1,2,3,6-tetrahydro-2,6-dioxo-9H-purin-8-yl)cinnamic Acid Nonaethylene Glycol Methyl Ether Ester;

(E)-4-(1,3-bis(cyclohexylethyl)-1,2,3,6-tetrahydro-2,6-dioxo-9H-purin-8-yl)cinnamic Acid Nonaethylene Glycol Methyl Ether Ester;

(E)-4-(1,3-bis(phenyl)-1,2,3,6-tetrahydro-2,6-dioxo-9H-purin-8-yl)cinnamic Acid Nonaethylene Glycol Methyl Ether Ester;

(E)-4-(1,3-bis(2-methyl-propyl)-1,2,3,6-tetrahydro-2,6-dioxo-9H-purin-8-yl)cinnamic Acid Nonaethylene Glycol Methyl Ether Ester;

(E)-4-((1-propyl-3-cyclohexylmethyl)-1,2,3,6-tetrahydro-2,6-dioxo-9H-purin-8-yl)cinnamic Acid Nonaethylene Glycol Methyl Ether Ester;

(E)-4-(1,3-bis(bicyclo(2.2.1)hept-2-ylmethyl)-1,2,3,6-tetrahydro-2,6-dioxo-9H-purin-8-yl)cinnamic Acid Nonaethylene Glycol Methyl Ether Ester;

(E)-4-(1-cyclohexylmethyl-3-butyl)-1,2,3,6-tetrahydro-2,6-dioxo-9H-purin-8-yl)cinnamic Acid Nonaethylene Glycol Methyl Ether Ester;

(E)-4-(1-cyclohexylmethyl-3-propyl)-1,2,3,6-tetrahydro-2,6-dioxo-9H-purin-8-yl)cinnamic Acid Nonaethylene Glycol Methyl Ether Ester;

(E)-4-((1,3-bis(3-fluorobenzyl)-1,2,3,6-tetrahydro-2,6-dioxo-9H-purin-8-yl)cinnamic Acid Nonaethylene Glycol Methyl Ether Ester;

(E)-4-((1,3-bis(2-fluorobenzyl)-1,2,3,6-tetrahydro-2,6-dioxo-9H-purin-8-yl)cinnamic Acid Nonaethylene Glycol Methyl Ether Ester;

(E)-4-((1,3-bisphenethyl)-1,2,3,6-tetrahydro-2,6-dioxo-9H-purin-8-yl)cinnamic Acid Nonaethylene Glycol Methyl Ether Ester;

(E)-4-((1-H-3-(2-methyl-propyl)-1,2,3,6-tetrahydro-2,6-dioxo-9H-purin-8-yl)cinnamic Acid Nonaethylene Glycol Methyl Ether Ester;

(E)-4-(1,3-bis(4-fluorobenzyl)-1,2,3,6-tetrahydro-2,6-dioxo-9H-purin-8-yl)cinnamic Acid Nonaethylene Glycol Methyl Ether Ester;

(E)-4-(1,3-bis(cyclohexylmethyl)-1,2,3,6-tetrahydro-2,6-dioxo-9H-purin-8-yl)cinnamic Acid Hexaethylene Glycol dodecyl Ether Ester;

(E)-4-(1,3-bis(cyclobutylmethyl)-1,2,3,6-tetrahydro-2,6-dioxo-9H-purin-8-yl)cinnamic Acid Nonaethylene Glycol Methyl Ether Ester;

(E)-4-(1-methyl-3-isobutyl)-1,2,3,6-tetrahydro-2,6-dioxo-9H-purin-8-yl)cinnamic Acid Nonaethylene Glycol Methyl Ether Ester;

4-(1,3-bis(cyclohexylmethyl)-1,2,3,6-tetrahydro-2,6-dioxo-9H-purin-8-yl)benzoic Acid Nonaethylene Glycol Methyl Ether Ester;

(E)-3-(1,3-bis(cyclohexylmethyl)-1,2,3,6-tetrahydro-2,6-dioxo-9H-purin-8-yl)cinnamic Acid Nonaethylene Glycol Methyl Ether Amide;

(E)-4-(1,3-Bis(cyclohexylmethyl)-1,2,3,6-tetrahydro-2,6-dioxo-9H-purin-8-yl)cinnamic Acid-N-methyl Nonaethylene Glycol Methyl Ether Amide;

(E)-4-(1,3-Bis(cyclohexylmethyl)-1,2,3,6-tetrahydro-2,6-dioxo-9H-purin-8-yl)cinnamic Acid Nonaethylene Glycol Methyl Ether Amide;

4-(1,3-Bis(cyclohexylmethyl)-1,2,3,6-tetrahydro-2,6-dioxo-9H-purin-8-yl)benzoic Acid Nonaethylene Glycol Methyl Ether Amide;

(E)-4-(1,3-Bis(cyclohexylmethyl)-2,3,6,7-tetrahydro-2,6-dioxo-7-benzyl-1H-purin-8-yl)cinnamic Acid Nonaethylene Glycol Methyl Ether Ester;

(E)-(1,3-Bis(cyclohexylmethyl)-2,3,6,7-tetrahydro-2,6-dioxo-7-(2-oxo-2-phenylethyl)-1H-purin-8-yl)cinnamic Acid Nonaethylene Glycol Methyl Ether Ester;

(E)-4-(1,3-Bis(cyclohexylmethyl)-2,3,6,7-tetrahydro-2,6-dioxo-7-methyl-1H-purin-8-yl)cinnamic Acid Nonaethylene Glycol Methyl Ether Ester;

(E)-1,3-Bis(cyclohexylmethyl)-2,3,6,7-tetrahydro-2,6-dioxo-7-(2-propynyl)-1H-purin-8-yl)cinnamic Acid Nonaethylene Glycol Methyl Ether Ester;

(E)-4-(1,3-Bis(cyclohexylmethyl)-2,3,6,7-tetrahydro-2,6-dioxo-7-(2-oxo-2-methylethyl)-1H-purin-8-yl)cinnamic Acid Nonaethylene Glycol Methyl Ether Ester;

(E)-4-(1,3-Bis(cyclohexylmethyl)-2,3,6,7-tetrahydro-2,6-dioxo-7-(3-morpholinopropyl)-1H-purin-8-yl) cinnamic Acid Nonaethylene Glycol Methyl Ether Ester;

(E)-4-(1,3-Bis(cyclohexylmethyl)-2,3,6,7-tetrahydro-2,6-dioxo-7-ethyl-1H-purin-8-yl)cinnamic Acid Nonaethylene Glycol Methyl Ether Ester;

(E)-4-(1,3-Bis(cyclohexylmethyl)-2,3,6,7-tetrahydro-2,6-dioxo-7-(2-ethoxy-2-oxoethyl)-1H-purin-8-yl) cinnamic Acid Nonaethylene Glycol Methyl Ether Ester;

(E)-4-(1,3-Bis(cyclohexylmethyl)-2,3,6,7-tetrahydro-2,6-dioxo-7-(2-methyl-2-propenyl)-1H-purin-8-yl) cinnamic Acid Nonaethylene Glycol Methyl Ether Ester;

(E)-4-(1,3-Bis(cyclohexylmethyl)-2,3,6,7-tetrahydro-2,6-dioxo-7-(cyanomethyl)-1H-purin-8-yl)cinnamic Acid Nonaethylene Glycol Methyl Ether Ester;

4-(1,3-Bis(cyclohexylmethyl)-2,3,6,7-tetrahydro-2,6-dioxo-7-benzyl-1H-purin-8-yl)benzoic Acid Nonaethylene Glycol Methyl Ether Ester;

4-(1,3-Bis(cyclohexylmethyl)-2,3,6,7-tetrahydro-2,6-dioxo-7-methyl-1H-purin-8-yl)benzoic Acid Nonaethylene Glycol Methyl Ether Ester;

(E)-4-(1,3-Bis(cyclohexylmethyl)-2,3,6,7-tetrahydro-2,6-dioxo-7-methyl-1H-purin-8-yl)cinnamic Acid Nonaethylene Glycol Methyl Ether Amide;

(E)-4-(1,3-Bis(cyclohexylmethyl)-2,3,6,7-tetrahydro-2,6-dioxo-7-benzyl-1H-purin-8-yl)cinnamic Acid Nonaethylene Glycol Methyl Ether Amide;

4-(1,3-Bis(cyclohexylmethyl)-2,3,6,7-tetrahydro-2,6-dioxo-7-benzyl-1H-purin-8-yl)benzoic Acid Nonaethylene Glycol Methyl Ether Amide;

1,3-Bis(cyclohexylmethyl)-8-[4-(2,5,8,11,14,17,20,23,26,29-decaoxatriacont-1-yl)phenyl]-3,7-dihydro-1H-purine-2,6-dione;

(E)-3-[5-[1,3-bis(cyclohexylmethyl)-2,3,6,7-tetrahydro-2,6-dioxo-1H-purin-8-yl]-2-thienyl]-2-propenoic Acid Nonaethylene Glycol Methyl Ether Ester;

6-(1,3-Bis(cyclohexylmethyl)-1,2,3,6-tetrahydro-2,6-dioxo-9H-purin-8-yl)nicotinic Acid Nonaethylene Glycol Methyl Ether Amide;

(E)-3-(1,3-Bis(cyclohexylmethyl)-1,2,3,6-tetrahydro-2,6-dioxo-9H-purin-8-yl)cinnamic Acid N-cyclopropylmethyl Nonaethylene Glycol Methyl Ether Amide;

(E)-4-[(3-Cyclohexylmethyl)-2,3,6,7-tetrahydro-2,6-dioxo-7-methyl-1H-purin-8-yl]cinnamic Acid Nonaethylene Glycol Methyl Ether Ester;

4-[1,3-Bis(cyclohexylmethyl)-1,2,3,6-tetrahydro-2,6-dioxo-9H-purin-8-yl]benzylamine N-Heptaethylene Glycol Methyl Ether Hydrochloride;

1,3-Bis(cyclohexylmethyl)-8-[3-(2,5,8,11,14,17,20,23,26,29-decaoxatriacont-1-yl)phenyl]-3,7-dihydro-1H-purine-2,6-dione;

(E)-4-(1,3-bis(cyclopentylmethyl)-1,2,3,6-tetrahydro-6-oxo-2-thioxo-9H-purin-8-yl)cinnamic Acid Nonaethylene Glycol Methyl Ether Amide;

(E)-4-(1,3-Bis(cyclohexylmethyl)-2,3,6,7-tetrahydro-2,6-dioxo-7-propyl-1H-purin-8-yl)cinnamic Acid Nonaethylene Glycol Methyl Ether Ester.

The compounds of the present invention are capable of existing as geometric and optical isomers. All such isomers, individually and as mixtures, are included within the scope of the present invention. Where Q contains a double bond, compounds in the form of the Egeometric isomers are preferred.

As mentioned hereinbefore, compounds of formula (I) or (Ia) and solvates thereof, have use in the prophylaxis and treatment of inflammatory conditions, immune disorders, tissue injury, infectious diseases, cancer and any disorder in which altered leukocyte adhesion contributes to the pathogenesis of the disease. This is demonstrated hereinafter in the biological assays in which representative compounds of the present invention have been shown to be active.

Examples of inflammatory conditions or immune disorders are those of the lungs, joints, eyes, bowel, skin; particularly those associated with the infiltration of leukocytes into inflamed tissue. Conditions of the lung include asthma, adult respiratory distress syndrome, pneumonia bronchitis and cystic fibrosis (which may additionally or alternatively involve the bowel or other tissue(s)). Conditions of the joint include rheumatoid arthritis, rheumatoid spondylitis, osteoarthritis, gouty arthritis and other arthritic conditions. Inflammatory eye conditions include uveitis (including iritis) and conjunctivitis. Inflammatory bowel conditions include Crohn's disease, ulcerative colitis and distal proctitis. Other conditions of the gastro intestinal tract include periodontal disease, esophagitis, NSAID—induced gastrointestinal damage, chemotherapy-induced mucositis, AIDS related diarrhoea and infectious diarrhoea. Skin diseases include those associated with cell proliferation, such as psoriasis, eczema and dermatitis (whether or not of allergic origin). Conditions of the heart include coronary infarct damage. Other inflammatory conditions and immune disorders include tissue necrosis in chronic inflammation, endotoxin shock, smooth muscle proliferation disorders (for example, restenosis following angioplasty), and tissue rejection following transplant surgery. Examples of circulatory disorders are those involving tissue damage as a result of leukocyte infiltration into tissue, such as coronary infarct damage and reperfusion injury. Other disorders include cancer and infectious diseases such as cerebral malaria, viral infections such as acquired immune deficiency syndrome (AIDS), and any other infection in which altered expression of adhesion molecules contributes to the pathogenicity.

Accordingly, the present invention also provides a method for the prophylaxis or treatment of an inflammatory condition or immune disorder in a mammal, such as a human, which comprises administration of a therapeutically effective amount of a compound of formula (I) or (Ia), or a pharmaceutically acceptable solvate thereof. The present invention further provides a method for the prophylaxis or treatment of septic shock in a mammal, such as a human, which comprises administration of a therapeutically effective amount of a compound of formula (I) or (Ia), or a pharmaceutically acceptable solvate thereof.

In the alternative, there is also provided a compound of formula (I) or (Ia), or a pharmaceutically acceptable solvate thereof for use in medical therapy; particularly, for use in the prophylaxis or treatment of an inflammatory condition or immune disorder in a mammal, such as a human. The present invention further provides a compound of formula (I) or (Ia), or a pharmaceutically acceptable solvate thereof for use in the prophylaxis or treatment of septic shock.

In a further aspect of the present invention, there is provided a cell adhesion molecule inhibitor, preferably a endothelial cell adhesion molecule inhibitor, for use in the treatment of periodontal disease, and methods of treating periodontal disease using a cell adhesion molecule inhibitor, preferably a endothelial cell adhesion molecule inhibitor.

There is also provided compounds of formula (I) or (Ia) for use in the manufacture of a medicament for the treatment of periodontal disease and methods of treating periodontal disease using compounds of formula (I) or (Ia).

There is also provided compounds of formula (Ib)

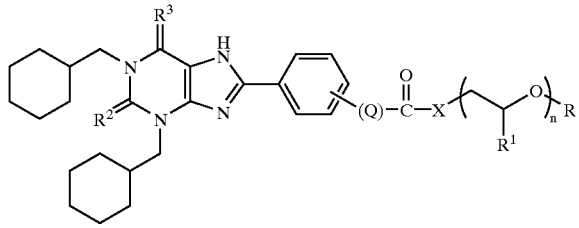

(Ib)

or a solvate thereof wherein:

X is —O— or —NH—;

Q is (—CH$_2$)$_p$, (—CH=CH—)$_p$, (—C≡C—)$_p$ where p is an integer of from 0 to 4;

R$^1$ is hydrogen or methyl;

R$^2$ and R$^3$ independently represent O or S, n is an integer of 1 to 50; and

R is hydrogen or methyl for use in the manufacture of a medicament for the treatment of periodontal disease and methods of treating periodontal disease by administration of a therapeutically effective amount of a compound of formula (Ib).

There is also provided a compound which is:

(E)-4-(1,3-Bis(cyclohexylmethyl)-1,2,3,6-tetrahydro-2,6-dioxo-9H-purin-8-yl)cinnamic Acid Decaethylene Glycol Methyl Ether Ester; and (E)-4-(1,3-Bis(cyclohexylmethyl)-1,2,3,6-tetrahydro-2,6-dioxo-9H-purin-8-yl)cinnamic Acid Nonaethylene Glycol Methyl Ether Ester;

(E)-3-[(1,3-Bis(cyclohexylmethyl)-1,2,3,6-tetrahydro-2,6-dioxo-9H-purin-8-yl]cinnamic Acid Nonaethylene Glycol Methyl Ether Ester;

(E)-4-[1,3-Bis(cyclohexylmethyl)-1,2,3,6-tetrahydro-2,6-dioxo-9H-purin-8-yl)cinnamic acid Nonaethylene Glycol Methyl Ether Amide; or, (E)-4-[1,3-Bis(cyclohexylmethyl)-1,2,3,6-tetrahydro-2,6-dioxo-9H-purin-8-yl)benzoic acid Nonaethylene Glycol Methyl Ether Ester for use in the manufacture of a medicament for the treatment of periodontal disease and methods of treating periodontal disease by administration of a therapeutically effective amount of said compound.

There is also provided (E)-4-(1,3-Bis(cyclohexylmethyl)-1,2,3,6-tetrahydro-2,6-dioxo-9H-purin-8-yl)cinnamic Acid Nonaethylene Glycol Methyl Ether Ester for use in the manufacture of a medicament for the treatment of periodontal disease and methods of treating periodontal disease by administration of a therapeutically effective amount of (E)-4-(1,3-Bis(cyclohexylmethyl)-1,2,3,6-tetrahydro-2,6-dioxo-9H-purin-8-yl)cinnamic Acid Nonaethylene Glycol Methyl Ether Ester.

The term "cell adhesion molecule" inhibitor includes compounds which specifically block or inhibit proteins on the surface of animal cells that mediate cell-cell binding. Preferably, the term "cell adhesion molecule inhibitor" includes compounds which inhibit the expression of cell adhesion molecules.

The term "endothelial cell adhesion molecule" inhibitor includes compounds which specifically block or inhibit the adhesive interactions of leukocytes and the endothelium. These compounds can be identified by performing the endothelial cell adhesion assay as described herein below. Preferably, the compounds have IC$_{50}$ values in this assay of 500 nM or less, more preferably 100 nM or less and even more preferably 50 nM or less. Preferably, the term "endothelial cell adhesion molecule inhibitor" includes compounds which inhibit the expression of endothelial cell adhesion molecules. More preferably, the endothelial cell adhesion molecules include ICAM-1 (Intercellular adhesion molecule-1), E-selectin, VCAM-1 and MadCAM.

The amount of a compound of formula (I) or (Ia) or pharmaceutically acceptable solvate thereof, which is required to achieve the desired biological effect will depend on a number of factors such as the use for which it is intended, the means of administration, and the recipient. A typical daily dose for the treatment of septic shock, for instance, may be expected to lie in the range of 0.005 mg/kg–100 mg/kg, preferably 0.5–100 mg/kg, and most preferably 0.5–20 mg/kg. This dose may be administered as a single unit dose or as several separate unit doses or as a continuous infusion. An intravenous dose may be expected to lie in the range of 0.0025 mg/kg to 200 mg/kg and would typically be administered as an infusion.

Similar dosages would be applicable for the treatment of other disease states. For administration to the lungs of a subject by aerosol an amount of the compound should be used sufficient to achieve concentrations on the airway surface liquid of the subject of about 2 to 1000 μmol. For inflammatory skin diseases, achievement of these same concentrations (2 to 1000 μmol) on the surface of the skin would be desirable for topical application of the compound. A daily dose administered orally for the treatment of inflammatory conditions may be expected to lie in the range of 0.05 mg/kg to 100 mg/kg, most preferably 0.5–20 mg/kg, which could be administered as a single unit dose or as several separate unit doses.

Thus, in a further aspect of the present invention, there are provided pharmaceutical compositions comprising, as active ingredient, a compound of formula (I) or (Ia) or a pharmaceutically acceptable salt or solvate thereof, together with at least one pharmaceutical carrier or recipient. These pharmaceutical compositions may be used in the prophylaxis and treatment of conditions such as septic shock, inflammatory conditions, and immune disorders. The carrier must be pharmaceutically acceptable to the recipient and must be compatible with, i.e. not have a deleterious effect upon, the other ingredients in the composition. The carrier may be a solid or liquid and is preferably formulated as a unit dose formulation, for example, a tablet which may contain from 0.05 to 95% by weight of the active ingredients. If desired other physiologically active ingredients may also be incorporated in the pharmaceutical compositions of the invention.

Possible formulations include those suitable for oral, sublingual, buccal, parenteral (for example subcutaneous, intramuscular, or intravenous), rectal, topical including transdermal, intranasal and inhalation administration. Most suitable means of administration for a particular patient will depend on the nature and severity of the condition being treated and on the nature of the active compound, but where possible, iv administration is preferred for the treatment of septic shock, for instance. For the treatment of a condition such as asthma, however, oral or inhalation, would be the preferred route of administration.

Formulations suitable for oral administration may be provided as discrete units, such as tablets, capsules, cachets, lozenges, each containing a predetermined amount of the active compound; as powders or granules; as solutions or suspensions in aqueous or non-aqueous liquids; or as oil-in-water or water-in-oil emulsions.

Formulations suitable for sublingual or buccal administration include lozenges comprising the active compound and, typically a flavoured base, such as sugar and acacia or tragacanth and pastilles comprising the active compound in an inert base, such as gelatine and glycerine or sucrose acacia.

Formulations suitable for parenteral administration typically comprise sterile aqueous solutions containing a predetermined concentration of the active compound; the solution is preferably isotonic with the blood of the intended recipient. Additional formulations suitable for parenteral administration include formulations containing physiologically suitable co-solvents and/or complexing agents such as surfactants and cyclodextrins. Oil-in-water emulsions are also suitable formulations for parenteral formulations. Although such solutions are preferably administered intravenously, they may also be administered by subcutaneous or intramuscular injection.

Formulations suitable for rectal administration are preferably provided as unit-dose suppositories comprising the active ingredient in one or more solid carriers forming the suppository base, for example, cocoa buffer.

Formulations suitable for topical or intranasal application include ointments, creams, lotions, pastes, gels, sprays, aerosols and oils. Suitable carriers for such formulations include petroleum jelly, lanolin, polyethyleneglycols, alcohols, and combinations thereof. The active ingredient is typically present in such formulations at a concentration of from 0.1 to 15% w/w.

Formulations of the invention may be prepared by any suitable method, typically by uniformly and intimately admixing the active compound with liquids or finely divided solid carriers or both, in the required proportions and then, if necessary, shaping the resulting mixture into the desired shape.

For example a tablet may be prepared by compressing an intimate mixture comprising a powder or granules of the active ingredient and one or more optional ingredients, such as a binder, lubricant, inert diluent, or surface active dispersing agent, or by moulding an intimate mixture of powdered active ingredient and inert liquid diluent.

Suitable formulations for administration by inhalation include fine particle dusts or mists which may be generated by means of various types of metered dose pressurised aerosols, nebulisers, or insufflators.

For pulmonary administration via the mouth, the particle size of the powder or droplets is typically in the range 0.5–10 $\mu$m, preferably 1–5 $\mu$m, to ensure delivery into the bronchial tree. For nasal administration, a particle size in the range 10–500 $\mu$m is preferred to ensure retention in the nasal cavity.

Metered dose inhalers are pressurised aerosol dispensers, typically containing a suspension or solution formulation of the active ingredient in a liquefied propellant. During use, these devices discharge the formulation through a valve adapted to deliver a metered volume, typically from 10 to 150 $\mu$l, to produce a fine particle spray containing the active ingredient. Suitable propellants include certain chlorofluorocarbon compounds, for example, dichloro-difluoromethane, trichlorofluoromethane, dichlorotetrafluoroethane and mixtures thereof. The formulation may additionally contain one or more co-solvents, for example, ethanol surfactants, such as oleic acid or sorbitan trioleate, anti-oxidants and suitable flavouring agents.

Nebulisers are commercially available devices that transform solutions or suspensions of the active ingredient into a therapeutic aerosol mist either by means of acceleration of a compressed gas typically air or oxygen, through a narrow venturi orifice, or by means of ultrasonic agitation. Suitable formulations for use in nebulisers consist of the active ingredient in a liquid carrier and comprising up to 40% w/w of the formulation, preferably less than 20%w/w. The carrier is typically water or a dilute aqueous alcoholic solution, preferably made isotonic with body fluids by the addition of, for example, sodium chloride.

Optional additives include preservatives if the formulation is not prepared sterile, for example, methyl hydroxybenzoate, anti-oxidants, flavouring agents, volatile oils, buffering agents and surfactants.

Suitable formulations for administration by insulation include finely comminuted powders which may be delivered by means of an insulator or taken into the nasal cavity in the manner of a snuff. In the insufflator, the powder is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation.

Therefore, according to a further aspect of the present invention, there is provided the use of a compound of formula (I) or (Ia) or a pharmaceutically acceptable solvate thereof in the preparation of a medicament for the prophylaxis or treatment of an inflammatory condition or immune disorder.

Compounds according to the invention can be made according to any suitable method of organic chemistry. Therefore, according to a further aspect of the invention, there is provided a process for preparing the compounds of formula (I) or (Ia), or solvates thereof which comprises reacting the compound of formula (II)

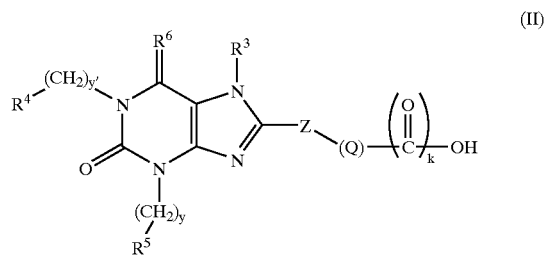

or an activated derivative thereof with a compound of formula (III)

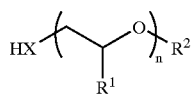

(III)

wherein Q, X, $R^1$, $R^2$, $R^4$, $R^5$, $R^6$, y, y' and n are as hereinbefore defined;

and optionally converting the compound of formula (I) or (Ia) so formed to a different compound of formula (I) or (Ia) or to a corresponding solvate. One skilled in the art can readily determine "activated derivatives" which may be employed in the instant process, using he tachings of T. W. Greene & P. G. M. Wuts in "Protective Groups in Organic Synthesis" John Wiley & Sons, Inc., New York, N.Y., 1991, pp 227–229.

When X is oxygen, the esterification may be effected by standard methods, for example using an acid catalyst and, optionally, an inert solvent such as toluene, benzene, or a xylene. Suitable acid catalysts include mineral acids; for example, sulphuric acid, hydrochloric acid, and phosporic acid; and organic acids; for example, methanesulphonic acid, or toluenesulphonic acid. The esterification is typically carried out at elevated temperature, for example, 50–150° C., preferably with removal of the water formed by distillation.

Where X is oxygen or —NH—, the reaction may be effected by first preparing an activated derivative of the compound of formula (II). Suitable activated derivatives include activated esters or acid halides and may either be isolated before reaction with the compound of formula (III) or prepared in situ. Suitable reagents for this process are thionyl chloride, oxalyl chloride, oxalyl bromide, phosphorous trichlodride, phosphorous tribromide, phosphorous pentachloride, phosphorous pentachloride, or diethyl chlorophosphate. Particularly useful activated esters of the compound of formula (II) are acylimidazoles which are readily prepared by reaction of the compound of formula (II) with N,N$^1$-carbonyldiimidazole.

Conversion of an activated derivative of the compound of formula (II) to a compound of formula (I) or (Ia) may be effected in an inert solvent, optimally in the presence of a non-nucleophilic base . Suitable solvents for the conversion of an activated derivative of the compound of formula (II) to a compound of formula (I) or (Ia) are those which do not change under the reaction conditions. These preferably include ethers such as diethyl ether, dioxane, tetrahydrofuran, glycol dimethyl ether, or hydrocarbons such as benzene, toluene, xylene, hexane, cyclohexane or petroleum fractions, or halogenated hydrocarbons such as dichloromethane, 1,2-dichloroethane, trichloromethane, tetrachloromethane, dichloroethylene, trichloroethylene, or chlorobenzene, or ethyl acetate, triethylamine, pyridine, dimethylsulphoxide, N,N-dimethylformamide, hexamethylphosphoramide, acetonitrile, acetone or nitromethane. It is also possible to use mixtures of the solvents mentioned. N,N-Dimethylformamide is preferred.

Bases which can be employed for the process are in general nonnucleophilic inorganic or organic bases. These preferably include alkali metal carbonates such as sodium carbonate or potassium carbonate, alkaline earth metal carbonates such as calcium carbonate, or alkali metal or alkaline earth metal alkoxides such as sodium or potassium tert-butoxide, or organic amines (trialkyl($C_1$–$C_6$)-amines such as triethylamine, or heterocycles such as 1,4-diazobicyclo[2.2.2]octane (DABCO), 1,8-diazobicyclo[5.40]undec-7-ene (DBU), pyridine, collidine, 4-dimethylaminopyridine, or N-methylpiperidine. It is also possible to employ as bases alkali metal hydrides such as sodium hydride. Potassium carbonate is preferred.

The reagents are in general employed in an amount from 0.5 to 3 mole equivalent, preferably from 1 to 1.5 mole equivalent, relative to 1 mole of the corresponding derivative of the compound of formula (II). In general, the base is employed in an amount from 0.05 to 10 mole equivalents, preferably from 1 to 2 mole relative to 1 mole of the compound of this invention.

The processes for manufacturing compounds according to the invention are in general carried out in a temperature of from about −30° C. to about 155° C., preferably from about −10° C. to about 75° C. The manufacturing processes are in general carried out at normal pressure. However, it is also possible to carry out the processes at elevated pressure or at reduced pressure (e.g. in a range from 0.5 to 5 bar).

In the general formula (I) or (Ia) where X is oxygen or —NH—, introduction of an $R^3$ substituent, where $R^3$ is as hereinbefore defined, may be effected by reaction with reactive alkyl or acyl halides in an inert solvent, optimally in the presence of a non-nucleophilic base. Suitable solvents for this process preferably include ethers such as diethyl ether, dioxane, tetrahydrofuran, glycol dimethyl ether or hydrocarbons such as benzene, toluene, xylene, hexane, cyclohexane or petroleum fractions, or halogenated hydrocarbons such as dichloromethane, 1,2-dichloroethane, trichlororhethane, tetrachloromethane, dichloroethylene, trichloroethylene, or chlorobenzene, or ethyl acetate, triethylamine, pyridine, dimethylsulphoxide, dimethylformamide, hexamethylphosphoramide, acetonitrile, acetone or nitromethane. It is also possible to use mixtures of the solvents mentioned. Dimethylformamide or 1,2-dichloroethane are preferred.

The compound of formula (II) may be prepared as described in PCT application No. GB 9501808 and U.S. Pat. No. 4,981,857 or by analogous methods apparent to a person skilled in the art.

Compounds of formula (III) are commercially available or may be prepared by literature methods. For example, R. A. Bartsch et al, J. Org. Chem. 1989, 54: 857–860 and J. M. Harris, Macromol. J.Sci. Rev. Polymer Phys. Chem. 1985, C25 (3): 325–373, and S. Zalopsky, Bioconjugate Chem. 1995, 6: 150–165. R. B. Greenwald, A. Pendri, D. Bolikal, J. Org. Chem. 1995, 60, 331–336; J. M. Harris, Rev. Macromol. Chem. Phys., 1985, C25(3), 325–373.

Alternatively, compounds of formula (I) or (Ia) may be prepared by condensation of a compound of formula (IV) or an acetal derivative thereof, or a compound of formula (V) or an activated derivative thereof, or a compound of formula (VI),

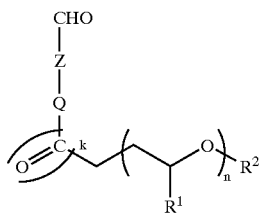

(IV)

-continued

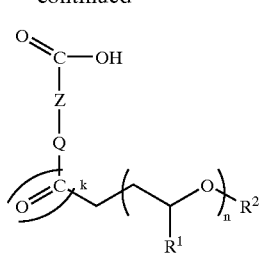

(V)

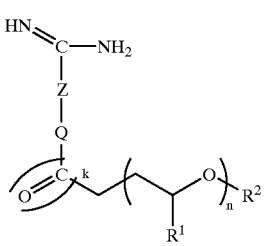

(VI)

wherein Q, X, Z. $R^1$, $R^2$ and n are as hereinbefore defined, with 1,3-disubstituted-5,6-diaminouracils (which may be prepared as described in the Examples). The condensation is suitably carried out in a polar solvent at non-extreme temperature as described in PCT Application No. GB9501808.

Compounds of formula (IV) may be prepared by coupling a compound of formula (III) with the appropriate carboxylic acid. Methods for effecting this coupling and for preparing the carboxylic acid are described in PCT Application No. GB9501808.

Conversion of a compound of formula (I) or (Ia) to a solvate thereof may be effected by standard methods known to a person skilled in the art.

Compounds of formula (Ib) may be prepared and formulated as described in PCT application publication No. WO 98.35966.

EXAMPLES

The invention will now be described by way of illustration only, by the following examples:

All reactions were performed in dried glassware under a positive pressure of dry argon or nitrogen, and were stirred magnetically unless otherwise indicated. Sensitive liquids and solutions were transferred via syringe or cannula, and introduced into reaction vessels through rubber septa. Unless otherwise stated, the term 'concentrated under reduced pressure' or 'in vacuo' refers to use of a Buchi rotary evaporator at approximately 15 mm Hg.

All temperatures are reported uncorrected in degrees Celsius (° C.). Unless otherwise indicated, all parts and percentages are by weight.

Commercial grade reagents and solvents were used without purification. Thin-layer chromatography (TLC) were performed on Merck KGA (EM Science) precoated glass-backed silica gel 60A F-254 250 Jim plates. Visualization of plates was effected by one or more of the following techniques: (a) ultraviolet illumination, (b) exposure to iodine vapor, (c) immersion of the plate in a 10% solution of phosphomolybdic acid in ethanol followed by heating, (d) immersion of the plate in cerium sulfate solution followed by heating, (e) immersion of the plate in 10% aqueous solution of potassium permanganate followed by heating, and/or (f) immersion of the plate in ammonium molybdenate solution followed by heating. Column chromatography (silica gel flash chromatography) was performed using 230–400 mesh Mallinckrodt SilirAR silica gel.

Melting points were determined using a Mel-Temp melting point apparatus and are uncorrected. Proton ($^1$H) nuclear magnetic resonance (NMR) spectra were measured with either a (300 MHz), Varian Unity 400 (400 MHz), or a Varian VXR 300 (300 MHz) spectrometer with either $Me_4Si$ ($\delta$ 0.00) or residual protonated solvent ($CHCl_3$ $\delta$ 7.26; MeOH $\delta$ 3.30; DMSO $\delta$ 2.49) as standard. Carbon ($^{13}$C) NMR spectra were measured with a Varian Unity 300 (75 MHz) spectrometer with solvent ($CDCl_3$ $\delta$ 7.00; MeOH-$d_3$ $\delta$ 49.0; DMSO-$d_6$ $\delta$ 39.5) as standard. Low resolution mass spectra were measured using either a Micromass Platform spectrometer operating in the positive ion electrospray mode or a VG 70SQ spectrometer equipped with a fast-atom bombardment (FAB) source (cesium gun). The Micromass instrument was calibrated with sodium iodide over the range 100–1100 atomic mass units (a.m.u.), yielding a mass accuracy of approximately 0.2 a.m.u. The resolution of the VG 70SQ instrument was set at approximately 1000 ppm (approximately 0.1 a.m.u.) for an accelerating voltage of 7 kV. Cesium iodide was used to calibrate this instrument in the 100–1500 a.m.u. range. FAB mass spectra were obtained using meta-nitrobenzyl alcohol as the sample matrix.

Elemental analyses were conducted by Atlantic Microlab, Inc. of Norcross, Ga. All compounds described below displayed NMR spectra, LRMS and either elemental analysis or HRMS consistent with assigned structures.

General Method for the Synthesis of Xanthine Carboxylic Acids

Example 1

Preparation of Compound 1

(E)-4-[1,3-bis(Cyclohexylmethyl)-1,2,3,6-tetrahydro-2,6-dioxo-9H-purin-8-yl]cinnamic Acid (a) 1,3-bis(Cyclohexylmethyl)urea A mixture of cyclohexanemethylamine (Aldrich, 68.66 g) and 5 N sodium hydroxide (Fisher, 200 ml) was stirred vigorously with cooling (–10° C.) while a solution of phosgene (30.0 g) in toluene (600 ml) was added rapidly. After stirring for 20 minutes, the resulting mixture was filtered and the precipitated solid was washed with water and dried (0.5 Torr) to give 1,3-bis(cyclohexylmethyl)urea as white powder (72.72 g, 95%), m.p. 150–152° C.; $^1$H-NMR (DMSO-$d_6$) $\delta$: 5.74 (br t, J=5.8 Hz, 2, 2 NH), 2.81 (t, J=6.3 Hz, 4, 2 $NCH_2$), 1.62, 1.25, and 0.85 (all m, 22, 2 cyclohexyl).

Anal. Calcd for $C_{15}H_{28}N_2O$: C, 71.38; H, 11.18; N, 11.10. Found: C, 71.22; H, 11.17; N, 11.15.

(b) 6-Amino-1,3-bis(cyclohexylmethyl)uracil

Cyanoacetic acid (Aldrich, 21.0 g) was dissolved in acetic anhydride (260 ml). This solution was added to 1,3-bis(cyclohexylmethyl)urea (from step (a), 54.5 g) and the solution maintained at 80° C. for 2 h under nitrogen. Volatiles were removed in vacuo and the residual oil dried by evaporation of portions of 10% water-ethanol (3×400 ml). The residual solids were dissolved in ethanol (600 ml)-water (300 ml) at 80° C. with adjustment of the pH to 10 by addition of 10% aqueous sodium carbonate. The hot solution was diluted with water (75 ml) and cooled to ambient temperature. The colorless crystals which formed were filtered off, washed with water and dried at 0.5 Torr to give 6-amino-1,3-bis(cyclohexylmethyl)uracil (64.98 g, 94%), m.p. 138–141° C.; $^1$H-NMR (DMSO-$d_6$) $\delta$: 6.73 (br s, 2, $NH_2$), 4.63 (s, 1, H-5), 3.67 (d, J=7.3 Hz, 2, $NCH_2$), 3.57 (d, J=7.3 Hz, 2, $NCH_2$), 1.55 and 1.09 (both m, 22, 2 cyclohexyl).

Anal. Calcd for $C_{18}H_{29}N_3O_2 \cdot H_2O$: C, 64.07; H, 9.26; N, 12.45. Found: C, 63.98; H, 9.27; N, 12.48.

(c) 6-Amino-1,3-bis(cyclohexylmethyl)-5-nitrosouracil

6-Amino-1,3-bis(cyclohexylmethyl)uracil (from step (b), 25.0 g) was dissolved in glacial acetic acid (440 ml), water (440 ml) and ethanol (440 ml) a reflux. To this solution was added sodium nitrite (5.65 g). The resulting mixture was stirred as it cooled slowly to ambient temperature. The lavender precipitate was filtered off, washed with 1:1 water-ethanol and dried to give 6-amino-1,3-bis(cyclohexylmethyl)-5-nitrosouracil as light purple crystals (23.46 g, 86%), m.p. 240–243° C. dec with effervescence; $^1$H-NMR (DMSO-$d_6$) δ: 13.23 (br s, 1, =NOH), 9.00 (br s, 1, =NH), 3.73 (br t, J=6.86, 4, 2 NCH$_2$), 2.0–1.6 and 1.7–1.1 (both m, total 22, 2 cyclohexyl).

Anal. Calcd for $C_{18}H_{28}N_4O_3$: C, 62.05; H, 8.10; N, 16.08. Found: C, 62.13; H, 8.12; N, 16.03.

(d) (E)-4-(1,3bis(Cyclohexylmethyl)-1,2,3,6-tetrahydro-2,6-dioxo-9H-purin-8-yl]cinnamic Acid The title compound was prepared from 1,3-bis(cyclohexylmethyl)-5,6-diaminouracil by the method of J. Perutmattam, Syn. Commun. 1989, 19:3367–3370. 1,3-Bis(cyclohexylmethyl)-5,6-diaminouracil was freshly prepared by shaking a mixture of 6-amino 1,3-bis(cyclohexylmethyl)-5-nitrosouracil (from step (c), 5.00 g) in methanol (250 ml)-water (25 ml) with 10% palladium on carbon (0.50 g) under hydrogen (50 psi) on a Parr shaker for 2 h. The catalyst was filtered off (Celite) and the colorless filtrate was concentrated to 25 ml. 4-Formylcinnamic acid (Aldrich, 2.53 g, 14.35 mmol) was added to this solution of 1,3-bis(cyclohexylmethyl)-5,6-diaminouracil and the resulting yellow mixture was concentrated and the residual yellow solid dried by evaporation of several portions of absolute ethanol. The resulting yellow powder (Schiff base intermediate) was stirred in dimethoxyethane (115 ml) with iodine (4.0 g) at 60° C. (oil bath) for 20 h. A saturated aqueous solution of sodium thiosulfate was added to the warm reaction mixture until complete decolorization of iodine resulted. The pale yellow precipitate was filtered off, washed with water, and dried at 0.5 Torr to give (E)-4-[1,3 bis(cyclohexylmethyl)-1,2,3,6-tetrahydro-2,6-dioxo-9H-purin-8-yl]cinnamic acid as a pale yellow powder (6.73 g, 91%), m.p. >300° C. Such samples were further purified by dissolving them in 1N aqueous sodium hydroxide, filtering the resulting hazy solution through Celite, and acidifying the clear filtrate with hydrochloric acid. The resulting precipitate was filtered and washed with water to give title compound as a pale yellow powder, m.p. >300° C.; $^1$H-NMR (DMSO-$d_6$) δ: 13.80 and 12.40 (both br m, 1 each, CO$_2$H and NH), 8.12 (d, J=8.3 Hz, 2, 2 phenyl CH), 7.84 (d, J=8.4 Hz, 2, 2 phenyl CH), 7.64 (d, J=16.0 Hz, 1, CH=), 6.64 (d, J=16.0 Hz, 1, CH=), 3.93 (d, J=7.0 Hz, 2, CH$_2$N), 3.79 (d, J=6.8 Hz, 2, CH$_2$N), 2.0–1.4 and 1.3–0.85 (both br m, 22 total, 2 cyclohexyl).

Anal. Calcd for $C_{28}H_{34}N_4O_4$: C, 68.55; H, 6.99; N, 11.42. Found: C, 68.45; H, 6.98; N, 11.48.

The compounds named in Table 1, below, were prepared by methods analogous to the method used above to prepare Example 1 and as described in WO 96/04280 (Feb. 15, 1996), U.S. Pat. No. 4,981,857 (Jan. 1, 1991) and U.S. Pat. No. 5,017, 577 (May 21, 1991).

TABLE 1

| EX. | NAME | ANALYTICAL | mp (° C.) |
|---|---|---|---|
| 2 | (E)-4-(1,3-bis(benzyl)-1,2,3,6-tetrahydro-2,6-dioxo-9H-purin-8-yl)cinnamic Acid | Calcd for $C_{28}H_{22}N_4O_4$: C, 70.28; H, 4.64; N, 11.71; Found: C, 70.04; H 4.67; N, 11.63 | >300 |
| 3 | (E)-4-(1,3-bis(cyclopentylmethyl)-1,2,3,6-tetrahydro-2,6-dioxo-9H-purin-8-yl)cinnamic Acid | Calcd for $C_{26}H_{30}N_4O_4$: C, 67.51; H, 6.54; N, 12.11; Found: C, 67.55; H 6.59; N, 12.15 | >300 |
| 4 | (E)-4-(1,3-bis(propyl)-1,2,3,6-tetrahydro-2,6-dioxo-9H-purin-8-yl)cinnamic Acid | Calcd for $C_{20}H_{22}N_4O_4$: C, 62.82; H, 5.80; N, 14.65; Found: C, 62.80; H 5.85; N, 14.60 | >300 |
| 5 | (E)-4-(1,3-bis(cyclopropylmethyl)-1,2,3,6-tetrahydro-2,6-dioxo-9H-purin-8-yl)cinnamic Acid | Calcd for $C_{22}H_{22}N_4O_4$: C, 65.01; H, 5.46; N, 13.78; Found: C, 65.14; H 5.52; N, 13.68 | >250 |
| 6 | (E)-3-((1-propyl-3-benzyl)-1,2,3,6-tetrahydro-2,6-dioxo-9H-purin-8-yl)cinnamic Acid | Calcd for $C_{24}H_{22}N_4O_4$: C, 66.97; H, 5.15; N, 13.02; Found: C, 66.82; H, 5.16; N, 12.85 | >350 |
| 7 | (E)-4-(1,3-bis(cycloheptylmethyl)-1,2,3,6-tetrahydro-2,6-dioxo-9H-purin-8-yl)cinnamic Acid | Calcd for $C_{30}H_{38}N_4O_4 \cdot 0.35 H_2O$: C, 68.64; H, 7.43; N, 10.67; Found: C, 68.61; H, 7.33; N, 10.71 | >250 |
| 8 | (E)-4-(1,3-bis(2-cyclohexylethyl)-1,2,3,6-tetrahydro-2,6-dioxo-9H-purin-8-yl)cinnamic Acid | Calcd for $C_{30}H_{38}N_4O_4$: C, 69.47; H, 7.38; N, 10.80; Found: C, 69.32; H, 7.36; N, 10.70 | >250 |
| 9 | (E)-4-(1,3-bis(phenyl)-1,2,3,6-tetrahydro-2,6-dioxo-9H-purin-8-yl)cinnamic Acid | Calcd for $C_{26}H_{18}N_4O_4$: C, 69.33; H, 4.02; N, 12.43; Found: C, 69.31; H, 4.05; N, 12.36 | >375 |
| 10 | (E)-4-(1,3-bis(2-methylpropyl)-1,2,3,6-tetrahydro-2,6-dioxo-9H-purin-8-yl)cinnamic Acid | Calcd for $C_{22}H_{26}N_4O_4$: C, 64.37; H, 6.39; N, 13.65; Found: C, 64.23; H, 6.42; N, 13.64 | >300 |
| 11 | (E)-4-((1-propyl-3-cyclohexylmethyl)-1,2,3,6-tetrahydro-2,6-dioxo-9H-purin-8-yl)cinnamic Acid | Calcd for $C_{24}H_{28}N_4O_4 \cdot 0.35 H2O$: C, 65.10; H, 6.53; N, 12.65; Found: C, 65.03; H, 6.52; N, 12.58 | >350 |
| 12 | (E)-4-(1,3-bis(bicyclo(2.2.1)hept-2-ylmethyl)-1,2,3,6-tetrahydro-2,6-dioxo-9H-purin-8-yl)cinnamic Acid | Calcd for $C_{30}H_{34}N_4O_4$: C, 70.02; H, 6.66; N, 10.89; Found: C, 69.96; H, 6.69; N, 10.86 | >250 |
| 13 | (E)-3-(1,3-bis(benzyl)-1,2,3,6-tetrahydro-2,6-dioxo-9H-purin-8-yl)cinnamic Acid | Calcd for $C_{28}H_{22}N_4O_4 \cdot 0.2 H2O$: C, 69.76; H, 4.68; N, 11.62; Found: C, 69.81; H, 4.66; N, 11.57 | >350 |

TABLE 1-continued

| EX. | NAME | ANALYTICAL | mp (° C.) |
|---|---|---|---|
| 14 | (E)-4-(1,3-bis(methyl)-1,2,3,6-tetrahydro-2,6-dioxo-9H-purin-8-yl)cinnamic Acid | Calcd for $C_{16}H_{14}N_4O_4 \cdot 1.0.H_2O$: C, 55.81; H, 4.68; N, 16.27; Found: C, 56.05; H, 4.69; N, 16.27 | >350 |
| 15 | (E)-4-(1-cyclohexylmethyl-3-butyl)-1,2,3,6-tetrahydro-2,6-dioxo-9H-purin-8-yl)cinnamic Acid | Calcd for $C_{25}H_{30}N_4O_4 \cdot 0.4.H_2O$: C, 65.60; H, 6.78; N, 12.24; Found: C, 65.60; H, 6.74; N, 12.29 | >350 |
| 16 | (E)-4-((1-cyclohexylmethyl-3-propyl)-1,2,3,6-tetrahydro-2,6-dioxo-9H-purin-8-yl)cinnamic Acid | Calcd for $C_{24}H_{28}N_4O_4 \cdot 0.3.H_2O$: C, 65.23; H, 6.52; N, 12.68; Found: C, 65.21; H, 6.48; N, 12.58 | >350 |
| 17 | (E)-4-(1,3-bis(benzyl)-1,2,3,6-tetrahydro-2-thioxo-6-oxo-9H-purin-8-yl)cinnamic Acid | Calcd for $C_{28}H_{22}N_4O_3S$: C, 68.00; H, 4.45; N, 11.33; S, 6.48; Found: C, 67.90; H, 4.53; N, 11.26; S, 6.43 | >350 |
| 18 | (E)-4-(1-methyl-3-(4-cyanobenzyl))-1,2,3,6-tetrahydro-2,6-dioxo-9H-purin-8-yl)cinnamic Acid | Calcd for $C_{23}H_{17}N_5O_4$: C, 64.63; H, 4.01; N, 16.38; Found: C, 64.58; H, 4.06; N, 16.36 | >350 |
| 19 | (E)-4-(1-methyl-3-(3-cyanobenzyl))-1,2,3,6-tetrahydro-2,6-dioxo-9H-purin-8-yl)cinnamic Acid | Calcd for $C_{23}H_{17}N_5O_4$: C, 64.63; H, 4.01; N, 16.38; Found: C, 64.40; H, 4.04; N, 16.45 | >300 |
| 20 | (E)-4-(1,3-bis(3-fluorobenzyl)-1,2,3,6-tetrahydro-2,6-dioxo-9H-purin-8-yl)cinnamic Acid | Calcd for $C_{28}H_{20}N_4O_4F_2$: C, 65.37; H, 3.92; N, 10.89; F, 7.38; Found: C, 65.21; H, 3.93; N, 10.84; F, 7.68 | >300 |
| 21 | (E)-4-(1,3-bis(2-fluorobenzyl)-1,2,3,6-tetrahydro-2,6-dioxo-9H-purin-8-yl)cinnamic Acid | Calcd for $C_{28}H_{20}N_4O_4F_2$: C, 65.37; H, 3.92; N, 10.89; F, 7.38; Found: C, 65.28; H, 3.94; N, 10.59; F, 7.53 | >350 |
| 22 | (E)-4-(1,3-bis(2-phenylethyl)-1,2,3,6-tetrahydro-2,6-dioxo-9H-purin-8-yl)cinnamic Acid | Calcd for $C_{30}H_{26}N_4O_4F_2$: C, 71.13; H, 5.17; N, 11.06; Found: C, 70.99; H, 5.21; N, 11.04 | >350 |
| 23 | (E)-4-((1-cyclohexylmethyl-3-methyl)-1,2,3,6-tetrahydro-2,6-dioxo-9H-purin-8-yl)cinnamic Acid | Calcd for $C_{22}H_{24}N_4O_4 \cdot 0.2.H_2O$: C, 64.13; H, 5.97; N, 13.60; Found: C, 64.18; H, 5.99; N, 13.60 | >300 |
| 24 | (E)-4-((1-H-3-(2-methylpropyl)-1,2,3,6-tetrahydro-2,6-dioxo-9H-purin-8-yl)cinnamic Acid | Calcd for $C_{18}H_{18}N_4O_4$: C, 61.01; H, 5.12; N. 15.81; Found: C, 60.85; H, 5.17; N, 15.74 | >300 |
| 25 | (E)4-(1,3-bis(4-fluorobenzyl)-1,2,3,6-tetrahydro-2,6-dioxo-9H-puri-8-yl)cinnamic Acid | Calcd for $C_{28}H_{20}N_4O_4F_2 \cdot 0.39.H2O$: C, 64.49; H, 4.02; N, 10.74; F, 7.29; Found: C, 64.37; H, 3.95; N, 10.64; F, 7.41 | >300 |
| 26 | (E)-3-[1,3-bis(propyl)-1,2,3,6-tetrahydro-2,6-dioxo-9H-purin-8-yl]cinnamic Acid | Calcd for $C_{20}H_{22}N_4O_4 \cdot 0.35.H_2O$: C, 61.80; H, 5.89; N, 14.41; Found: C, 61.76; H, 5.89; N, 14.42 | >350 |
| 27 | (E)-4-(1,3-bis(cyclobutylmethyl-1,2,3,6-tetrahydro-2,6-dioxo-9H-purin-8-yl)cinnamic Acid | Calcd for $C_{24}H_{26}N_4O_4 \cdot 0.5.H_2O$: C, 65.00; H, 6.14; N, 12.63; Found: C, 64.93; H, 6.11; N, 12.64 | >300 |
| 28 | (E)-4-((1-methyl-3-cyclohexylmethyl)-1,2,3,6-tetrahydro-2,6-dioxo-9H-purin-8-yl)cinnamic Acid | Calcd for $C_{22}H_{24}N_4O_4 \cdot 0.90.H_2O$: C, 62.22; H, 6.12; N, 13.19; Found: C, 62.17; H, 6.12; N, 13.16 | >300 |
| 29 | (E)-4-((1-methyl-3-(2-methylpropyl))-1,2,3,6-tetrahydro-2,6-dioxo-9H-purin-8-yl)cinnamic Acid | Calcd for $C_{19}H_{20}N_4O_4$: C, 61.95; H, 5.47; N, 15.21; Found: C, 61.85; H, 5.50; N, 15.18 | >300 |
| 30 | (E)-4-(1,3-Bis(3-pyridinylmethyl)-1,2,3,6-tetrahydro-2,6-dioxo-9H-purin-8-yl)cinnamic Acid | Calcd for $C_{26}H_{20}N_6O_4 \cdot 2.0.H_2O$: C, 60.46; H, 4.68; N, 16.27; Found: C, 60.50; H, 4.71; N, 16.26 | >300 |
| 31 | (E)-3-[1,3-Bis(cyclohexylmethyl)-1,2,3,6-tetrahydro-2,6-dioxo-9H-purin-8-yl]cinnamic Acid | Calcd for $C_{28}H_{34}N_4O_4 \cdot 0.10.H_2O$: C, 68.30; H, 7.00; N, 11.38; Found: C, 68.33; H, 6.93; N, 11.34 | >350 |
| 32 | 4-[(1,3-Bis(cyclohexylmethyl)-1,2,3,6-tetrahydro-2,6-dioxo-9H-purin-8-yl]benzoic Acid | Calcd for $C_{26}H_{32}N_6O_4 \cdot 0.25.H_2O$: C, 66.58; H, 6.98; N, 11.94; Found: C, 66.62; H, 6.98; N, 11.94 | >300 |
| 33 | (E)-4-[(1,3-Biscyclohexyl-1,2,3,6-tetrahydro-2,6-dioxo-9H-purin-8-yl)cinnamic Acid | Calcd for $C_{26}H_{18}N_4O_4$: C, 69.33; H, 4.03; N, 12.44. Found: C, 69.31; H, 4.05; N, 12.36 | >375 |

General Method for the Synthesis of Xanthine Carboxylic Acid Esters

Example 34

(E)-4-[(1,3-bis(Benzyl)-1,2,3,6-tetrahydro-2,6-dioxo-9H-purin-8-yl]cinnamic Acid Nonaethylene Glycol Methyl Ether Ester (a) Nonaethylene Glycol Monomethyl Ether Sodium hydride (8.6 g, 344 mmol as 95%) was added to a solution of hexaethylene glycol (Aldrich, 100 g) in anhydrous tetrahydrofuran (1000 mL) at 15° C. The resulting mixture was stirred while coming to ambient temperature over 1 h. Benzyl bromide (Aldrich, 59.9 g) was added dropwise over 1 h and the resulting mixture stirred at ambient temperature for 16 h. The cooled mixture was diluted with water (200 mL) and extracted with diethyl ether. The combined diethyl ether extracts were washed with water. The combined aqueous layers were saturated with sodium chloride and extracted with methylene chloride. The combined methylene chloride layers were washed with saturated sodium chloride and dried (magnesium sulfate). Removal of the volatiles under reduced pressure left hexaethylene glycol monobenzyl ether (80.5 g, 64%); $^1$H-NMR (CDCl$_3$) δ: 7.30 (m, 5, 5 phenyl CH), 4.53 (s, 2, benzyl CH$_2$), 3.69–3.54 (m, 22, 11 OCH$_2$), 3.06 (br s, 3, OH and CH$_2$O). A solution of hexaethylene glycol monobenzyl ether (80.0 g) in anhydrous THF (750 mL) was added to a suspension of sodium hydride (95%, 5.4 g) in tetrahydrofuran. The resulting mixture was stirred at ambient temperature for 30 min, and then a solution of triethylene glycol methyl tosyl ether (prepared as described in part (a) of Example 1, 68.4 g) in THF (100 mL) was added dropwise. The mixture was refluxed under nitrogen overnight. Additional sodium hydride (2.5 g) was added and reflux continued an additional 24 h. The mixture was cooled (ice bath), quenched with water (2 L), and extracted with diethyl ether. The aqueous layer was washed with methylene chloride. The combined organic layers were dried (magnesium sulfate) and concentrated to a brown oil which was filtered through a silica gel pad washed with methylene chloride. Methylene chloride was evaporated to leave nonaethylene glycol benzyl methyl ether as an oil (63.1 g, 57%). $^1$H-NMR (300 MHz, DMSO-d$_6$) δ: 7.23 (m, 5H, 5 phenyl CH), 4.38 (s, 2H, benzyl CH$_2$), 3.50–3.30 (m, 36H, 18 CH$_2$O), 3.13 (s, 3H, CH$_3$).

A solution of nonaethylene glycol benzyl methyl ether (10 g, 19.3 mmol) in ethanol (200 mL) was shaken with 10% palladium on activated charcal (Aldrich, 1.0 g) under hydrogen (50 psi) on a Parr apparatus for 3 h. The catalyst was filtered off (Celite), and the filtrate was concentrated in vacuo and dried by evaporation of toluene to provide nonaethylene glycol monomethyl ether as an oil (8.17 g, 99%). $^1$H-NMR (300 MHz, DMSO-d$_6$) δ: 4.56 (t, 1H OH), 3.60–3.35 (m, 36H, 18 OCH$_2$), 3.22 (s, 3H, CH$_3$).

Anal. Calcd for C$_{19}$H$_{40}$O$_{10}$: C, 53.26; H, 9.41. Found: C, 53.25; H, 9.41.

(b) (E)-4-[(1,3-bis(Benzyl)-1,2,3,6-tetrahydro-2,6-dioxo-9H-purin-8-yl]cinnamic Acid Nonaethylene Glycol Methyl Ether Ester A slurry of (E)-4-[(1,3-bis(benzyl)-1,2,3,6-tetrahydro-2, 6-dioxo-9H-purin-8-yl]cinnamic acid (Example 2, 0.50 g, 1.05 mmol) in anhydrous N,N-dimethylformamide (10 mL) was heated briefly to near reflux under nitrogen. N,N'-Carbonyldiimidazole (Aldrich, 0.210 g, 1.25 mmol) was added to the pale yellow slurry, which thinned and turned orange as a gas evolved. Within minutes the slurry turned a bright yellow and thickened as a yellow solid formed. The mixture was stirred for 18 h, diluted with dichloromethane (30 mL), and filtered. The bright yellow filter plug was washed with dichloromethane (30 mL), and dried at 40° C. to provide (E)-1,3-bis(benzyl)-8-(3-(2-(1H-imidazol-1-ylcarbonyl)vinyl)phenyl)-9H-purin-2,6(1H,3H)-dione as a yellow powder (0.415 g). A mixture of this compound (0.41 g, 0.77 mmol), nonaethylene glycol monomethyl ether, (from Example 24, part (a), 0.348 g, 0.81 mmol) and potassium carbonate, (Aldrich, 0.212 g, 1.54 mmol) in acetonitrile (10 ml) was stirred at reflux for 20 hours. Chloroform (50 ml) was added and the solution was washed with 1N hydrochloric acid, saturated aqueous sodium chloride, dried over magnesium sulfate, and filtered. This solution was concentrated under reduced pressure and the crude material was purified by silica gel chromatography by eluting with 10% methanol in chloroform. Evaporation of solvents gave the title compound (0.40 g, 59%) as a yellow waxy solid. $^1$H-NMR (300 MHz, DMSO-d$_6$) δ: 8.15 (d, J=8.2 Hz, 2H, phenylCH), 7.87 (d, J=8.4 Hz, 2H, 2 phenylCH), 7.68 (d, J=15.9 Hz, 1H, CH=), 7.45–7.20 (m, 10H, 2 C$_6$H$_5$), 6.75 (d, J=15.9 Hz, 1H, CH—), 5.24 and 5.10 (2s, 4H, 2CH$_2$phenyl), 4.25 (m, 2H, CH$_2$O), 3.70 (m, 2H, CH$_2$O), 3.60–3.30 (m, 32H, 16CH$_2$), 3.20(s, 3H, CH$_3$).

Anal. Calcd for C$_{47}$H$_{60}$N$_4$O$_{13}$: C, 63.50; H, 6.80; N, 6.30; Found: C, 63.41; H, 6.65; N, 6.52.

The compounds named in Table 2, below, were prepared by methods analogous to the methods used above to prepare Example 34. (SM=starting material).

TABLE 2

| EX. | NAME | MASS SPEC/ METHOD | ANALYTICAL | SM |
|---|---|---|---|---|
| 35 | (E)-4-[1,3-Bis(cyclohexylmethyl)-1,2,3,6-tetrahydro-2,6-dioxo-9H-purin-8-yl]cinnamic Acid Nonaethylene Glycol Methyl Ether Ester | 901 (M + H)$^+$; FAB | Calcd for C$_{47}$H$_{72}$N$_4$O$_{13}$: C, 62.65; H, 8.05; N, 6.22; Found: C, 62.33; H, 7.94; N, 6.25 | Example 1 |
| 36 | (E)-4-(1,3-bis(cyclopentylmethyl)-1,2,3,6-tetrahydro-2,6-dioxo-9H-purin-8-yl)cinnamic Acid Nonaethylene Glycol Methyl Ether Ester | 873 (M + H)$^+$; FAB | Calcd for C$_{45}$H$_{68}$N$_4$O$_{13}$.0.50.H$_2$O: C, 61.28; H, 7.88; N, 6.35; Found: C, 61.27; H, 7.69; N, 6.72 | Example 3 |
| 37 | (E)-4-(1,3-bis(propyl)-1,2,3,6-tetrahydro-2,6-dioxo-9H-purin-8-yl)cinnamic Acid Nonaethylene Glycol Methyl Ether Ester | 793 (M + H)$^+$; FAB | Calcd for C$_{39}$H$_{60}$N$_4$O$_{13}$.0.82.H$_2$O: C, 58.00; H, 7.69; N, 6.94; Found: C, 57.99; H, 7.36; N, 7.20 | Example 4 |
| 38 | (E)-4-(1,3-bis(cyclopropylmethyl)-1,2,3,6-tetrahydro-2,6-dioxo-9H-purin-8-yl)cinnamic Acid Nonaethylene Glycol Methyl Ether Ester | 817 (M + H)$^+$; FAB | Calcd for C$_{41}$H$_{60}$N$_4$O$_{13}$.0.93.H2O: C, 59.07; H, 7.48; N, 6.72; Found: C, 59.07; H, 7.21; N, 7.03 | Example 5 |
| 39 | (E)-3-((1-propyl-3-benzyl)-1,2,3,6-tetrahydro-2,6-dioxo-9H-purin-8-yl)cinnamic Acid Nonaethylene Glycol Methyl Ether Ester | 841 (M + H)$^+$; FAB | Calcd for C$_{43}$H$_{60}$N$_4$O$_{13}$: C, 61.41; H, 7.19; N, 6.66; Found: C, 61.19; H, 7.16; N, 6.74 | Example 6 |
| 40 | (E)-4-(1,3-bis(cycloheptylmethyl)-1,2,3,6-tetrahydro-2,6-dioxo-9H-purin-8-yl)cinnamic Acid Nonaethylene Glycol Methyl Ether Ester | 929 (M + H)$^+$; FAB | Calcd for C$_{49}$H$_{76}$N$_4$O$_{13}$: C, 63.34; H, 8.24; N, 6.03; Found: C, 63.35; H, 8.19; N, 6.07 | Example 7 |

TABLE 2-continued

| EX. | NAME | MASS SPEC/ METHOD | ANALYTICAL | SM |
|---|---|---|---|---|
| 41 | (E)-4-(1,3-bis(2-cyclohexylethyl)-1,2,3,6-tetrahydro-2,6-dioxo-9H-purin-8-yl)cinnamic Acid Nonaethylene Glycol Methyl Ether Ester | 930 (M + H)$^+$; FAB | Calcd for $C_{49}H_{76}N_4O_{13}$: C, 63.34; H, 8.24; N, 6.03; Found: C, 63.18; H, 8.21; N, 6.14 | Example 8 |
| 42 | (E)-4-(1,3-bis(phenyl)-1,2,3,6-tetrahydro-2,6-dioxo-9H-purin-8-yl)cinnamic Acid Nonaethylene Glycol Methyl Ether Ester | 861 (M + H)$^+$; FAB | Calcd for $C_{45}H_{56}N_4O_{13}$·1.22·$H_2O$: C, 61.22; H, 6.67; N, 6.35; Found: C, 61.21; H, 6.35; N, 6.48 | Example 9 |
| 43 | (E)-4-(1,3-bis(2-methylpropyl)-1,2,3,6-tetrahydro-2,6-dioxo-9H-purin-8-yl)cinnamic Acid Nonaethylene Glycol Methyl Ether Ester | 821 (M + H)$^+$; FAB | Calcd for $C_{41}H_{64}N_4O_{13}$: C, 59.98; H, 7.86; N, 6.82; Found: C, 59.73; H, 7.81; N, 6.87 | Example 10 |
| 44 | (E)-4-((1-propyl-3-cyclohexylmethyl)-1,2,3,6-tetrahydro-2,6-dioxo-9H-purin-8-yl)cinnamic Acid Nonaethylene Glycol Methyl Ether Ester | 848 (M + H)$^+$; FAB | Calcd for $C_{43}H_{66}N_4O_{13}$: C, 60.98; H, 7.85; N, 6.61; Found: C, 60.81; H, 7.81; N, 6.65 | Example 11 |
| 45 | (E)-4-(1,3-bis(bicyclo(2.2.1)hept-2-ylmethyl)-1,2,3,6-tetrahydro-2,6-dioxo-9H-purin-8-yl)cinnamic Acid Nonaethylene Glycol Methyl Ether Ester | 925 (M + H)$^+$; FAB | Calcd for $C_{49}H_{72}N_4O_{13}$·0.76·$H_2O$: C, 62.69; H, 7.89; N, 5.97; Found: C, 62.69; H, 7,77; N, 6.02 | Example 12 |
| 46 | (E)-3-(1,3-bis(benzyl)-1,2,3,6-tetrahydro-2,6-dioxo-9H-purin-8-yl)cinnamic Acid Nonaethylene Glycol Methyl Ether Ester | 889 (M + H)$^+$; FAB | Calcd for $C_{47}H_{60}N_4O_{13}$·0.79·$H_2O$: C, 62.50; H, 6.87; N, 6.20; Found: C, 62.50; H, 6.83; N, 6.21 | Example 13 |
| 47 | (E)-4-(1,3-bis(methyl)-1,2,3,6-tetrahydro-2,6-dioxo-9H-purin-8-yl)cinnamic Acid Nonaethylene Glycol Methyl Ether Ester | 737 (M + H)$^+$; FAB | Calcd for $C_{35}H_{52}N_4O_{13}$: C, 57.05; H, 7.11; N, 7.60; Found: C, 56.81; H, 7.09; N, 7.58 | Example 14 |
| 48 | (E)-4-(1-cyclohexylmethyl-3-butyl)-1,2,3,6-tetrahydro-2,6-dioxo-9H-purin-8-yl)cinnamic Acid Nonaethylene Glycol Methyl Ether Ester | 861 (M + H)$^+$; FAB | Calcd for $C_{44}H_{68}N_4O_{13}$: C, 61.38; H, 7.96; N, 6.51; Found: C, 61.19; H, 7.97; N, 6.56 | Example 15 |
| 49 | (E)-4-((1-cyclohexylmethyl-3-propyl)-1,2,3,6-tetrahydro-2,6-diox-9H-purin-8-yl)cinnamic Acid Nonaethylene Glycol Methyl Ether Ester | 847 (M + H)$^+$; FAB | Calcd for $C_{43}H_{66}N_4O_{13}$: C, 60.98; H, 7.85; N, 6.61; Found: C, 60.73; H, 7.71; N, 6.84 | Example 16 |
| 50 | (E)-4-(1,3-bis(benzyl)-1,2,3,6-tetrahydro-2-thioxo-6-oxo-9H-purin-8-yl)cinnamic Acid Nonaethylene Glycol Methyl Ether Ester | 905 (M + H)$^+$; FAB | Calcd for $C_{47}H_{60}N_4O_{12}S$·0.22·$H_2O$: C, 62.10; H, 6.70; N, 6.16; S, 3.35; Found: C, 62.10; H, 6.67; N, 6.20; S, 3.51 | Example 17 |
| 51 | (E)-4-(1-methyl-3-(4-cyanobenzyl)-1,2,3,6-tetrahydro-2,6-dioxo-9H-purin-8-yl)cinnamic Acid Nonaethylene Glycol Methyl Ether Ester | 838 (M + H)$^+$; FAB | Calcd for $C_{42}H_{55}N_4O_{13}$·0.42·$H_2O$: C, 59.60; H, 6.66; N, 8.29; Found: C, 59.66; H, 6.68; N, 8.28 | Example 18 |
| 52 | (E)-4-(1-methyl-3-(3-cyanobenzyl)-1,2,3,6-tetrahydro-2,6-dioxo-9H-purin-8-yl)cinnamic Acid Nonaethylene Glycol Methyl Ether Ester | 838 (M + H)$^+$; FAB | Calcd for $C_{42}H_{55}N_4O_{13}$·0.53·$H_2O$: C, 59.53; H, 6.67; N, 8.26; Found: C, 59.53; H, 6.69; N, 8.25 | Example 19 |
| 53 | (E)-4-(1,3-bis(3-fluorobenzyl)-1,2,3,6-tetrahydro-2,6-dioxo-9H-purin-8-yl)cinnamic Acid Nonaethylene Glycol Methyl Ether Ester | 925 (M + H)$^+$; FAB | Calcd for $C_{47}H_{58}N_4O_{13}F$·1.57·$H_2O$: C, 60.42; H, 6.60; N, 6.00; Found: C, 60.42; H, 6.23; N, 6.09 | Example 20 |
| 54 | (E)-4-(1,3-bis(2-fluorobenzyl)-1,2,3,6-tetrahydro-2,6-dioxo-9H-purin-8-yl)cinnamic Acid Nonaethylene Glycol Methyl Ether Ester | 925 (M + H)$^+$; FAB | Calcd for $C_{47}H_{58}N_4O_{13}F_2$·1.41·$H_2O$: C, 60.61; H, 6.58; N, 6.02; Found: C, 60.61; H, 6.29; N, 5.99 | Example 21 |
| 55 | (E)-4-(1,3-bis(2-phenylethyl)-1,2,3,6-tetrahydro-2,6-dioxo-9H-purin-8-yl)cinnamic Acid Nonaethylene Glycol Methyl Ether Ester | 917 (M + H)$^+$; FAB | Calcd for $C_{49}H_{64}N_4O_{13}$·1.43·$H_2O$: C, 62.42; H, 7.15; N, 5.94; Found: C, 62.42; H, 6.82; N, 5.98 | Example 22 |

TABLE 2-continued

| EX. | NAME | MASS SPEC/ METHOD | ANALYTICAL | SM |
|---|---|---|---|---|
| 56 | (E)-4-((1-cyclohexylmethyl-3-methyl)-1,2,3,6-tetrahydro-2,6-dioxo-9H-purin-8-yl)cinnamic Acid Nonaethylene Glycol Methyl Ether Ester | 819 (M + H)$^+$; FAB | Calcd for $C_{41}H_{62}N_4O_{13}$.1.59.$H_2O$: C, 58.10; H, 7.75; N, 6.61; Found: C, 58.10; H, 7.34; N, 6.85 | Example 23 |
| 57 | (E)-4-((1-H-3-(2-methylpropyl)-1,2,3,6-tetrahydro-2,6-dioxo-9H-purin-8-yl)cinnamic Acid Nonaethylene Glycol Methyl Ether Ester | 765 (M + H)$^+$; FAB | Calcd for $C_{37}H_{56}N_4O_{13}$.3.0.$H_2O$: C, 54.30; H, 7.58; N, 6.84; Found: C, 54.08; H, 6.93; N, 6.89 | Example 24 |
| 58 | (E)-4-(1,3-bis(4-fluorobenzyl)-1,2,3,6-tetrahydro-2,6-dioxo-9H-purin-8-yl)cinnamic Acid Nonaethylene Glycol Methyl Ether Ester | 925 (M + H)$^+$; FAB | Calcd for $C_{47}H_{58}N_4O_{13}F_2$.1.43.$H_2O$: C, 60.59; H, 6.58; N, 6.01; Found: C, 60.58; H, 6.23; N, 6.18 | Example 25 |
| 59 | (E)-4-(1,3-bis(cyclohexylmethyl)-1,2,3,6-tetrahydro-2,6-dioxo-9H-purin-8-yl)cinnamic Acid Hexaethylene Glycol dodecyl Ether Ester | 923 (M + H)$^+$; FAB | Calcd for $C_{52}H_{83}N_4O_{13}$: C, 67.65; H, 8.93; N, 6.07; Found: C, 67.41; H, 8.93; N, 6.45 | Example 1 |
| 60 | (E)-3-(1,3-bis(propyl)-1,2,3,6-tetrahydro-2,6-dioxo-9H-purin-8-yl)cinnamic Acid Nonaethylen Glycol Methyl Ether Ester | 793 (M + 1); ES+ | Calcd for $C_{39}H_{60}NO_{13}$.0.59.$H_2O$: C, 58.29; H, 7.67; N, 6.97; Found: C, 58.29; H, 7.64; N, 7.08 | Example 26 |
| 61 | (E)-4-(1,3-bis(cyclobutylmethyl)-1,2,3,6-tetrahydro-2,6-dioxo-9H-purin-8-yl)cinnamic Acid Nonaethylene Glycol Methyl Ether Ester | 845 (M + H)$^+$; ES+ | Calcd for $C_{43}H_{64}N_4O_{13}$.0.56.$H_2O$: C, 60.40; H, 7.68; N, 6.55; Found: C, 60.40; H, 7.52; N, 6.61 | Example 27 |
| 62 | (E)-4-(1-methyl-3-cyclohexylmethyl)-1,2,3,6-tetrahydro-2,6-dioxo-9H-purin-8-yl)cinnamic Acid Nonaethylene Glycol Methyl Ether Ester | 819 (M + H)$^+$; FAB | Calcd for $C_{41}H_{61}N_4O_{13}$.0.46.$H_2O$: C, 59.60; H, 7.55; N, 6.78; Found: C, 59.64; H, 7.41; N, 6.76 | Example 28 |
| 63 | (E)-4-(1-methyl-3-(2-methylpropyl)-1,2,3,6-tetrahydro-2,6-dioxo-9H-purin-8-yl)cinnamic Acid Nonaethylene Glycol Methyl Ether Ester | 779 (M + H)$^+$; FAB | Calcd for $C_{38}H_{58}N_4O_{13}$.0.87.$H_2O$: C, 57.44; H, 7.58; N, 7.05; Found: C, 57.44; H, 7.30; N, 7.16 | Example 29 |
| 64 | (E)-4-(1,3-Bis(3-pyridinylmethyl)-1,2,3,6-tetrahydro-2,6-dioxo-9H-purin-8-yl)cinnamic Acid Nonaethylene Glycol Methyl Ether Ester | 891 (M + H)$^+$; FAB | Calcd for $C_{45}H_{58}N_6O_{13}$.1.74.HCl: C, 56.63; H, 6.31; N, 8.81; Found: C, 56.63; H, 6.37; N, 8.63 | Example 30 |
| 65 | 4-(1,3-bis(cyclohexylmethyl)-1,2,3,6-tetrahydro-2,6-dioxo-9H-purin-8-yl)benzoic Acid Nonaethylene Glycol Methyl Ether Ester | | Calcd for $C_{45}H_{70}N_4O_{13}$: C, 61.77; H, 8.06; N, 6.40; Found: C, 61.55; H, 7.99; N, 6.52 | Example 32 |
| 66 | (E)-4-[1,3-Bis(cyclohexyl)-1,2,3,6-tetrahydro-2,6-dioxo-9H-purin-8-yl]cinnamic Acid Nonaethylene Glycol Methyl Ether Ester | 873 (M + H)$^+$; FAB | Calcd for $C_{45}H_{65}N_4O_{13}$.0.59 $H_2O$: C, 61.16; H, 7.89; N, 6.34; Found: C, 61.16; H, 7.969; N, 6.23 | Example 33 |

General Method for the Synthesis of Xanthine Carboxylic Acid Amides

Example 67

(E)-3-(1,3-bis(Cyclohexylmethyl)-1,2,3,6-tetrahydro-2,6-dioxo-9H-purin-8-yl)cinnamic Acid Nonaethylene Glycol Methyl Ether Amide (a) Amino Nonaethyleneglycol Methyl Ether To a solution of nonaethylene glycol monomethyl ether from Example 33, part (a), (8.0g. 18.7 mmol) in dichloromethane (75 ml) and triethylamine (5 ml, 3.74 mol) at 25° C. was added methanesulfonylchloride (2.36 g, 20.5 mmol). After stirring at room temperature 2 hours, the mixture was evaporated to a volume of 20 ml and filtered. The filtrate wash was evaporated to dryness and slurried in dichloromethane (20 ml) and filtered again. The filtrate wash was evaporated to a colorless oil (9.8 g). A solution of the above intermediate (8.50 g) in concentrated aqueous ammonium hydroxide (100 ml) was refluxed for 2.5 hours. The volatiles were removed in vacuo and the residual oil was dried by evaporation with toluene to give Amino nonaethyleneglycol methyl ether as a colorless oil (8.1 g). $^1$H -NMR (300 MHz, DMSO) δ: 3.60–3.40 (m, 36H, 18 $CH_2$ and $NH_2$), 3.20 (s, 3H, $CH_3$). MS (CI) 428 (m+1, 100%).

(b) (E)-3-(1,3-bis(Cyclohexylmethyl)-1,2,3,6-tetrahydro-2,6-dioxo-9H-purin-8-yl)cinnamic Acid Chloride A mixture of (E)-3-(1,3-bis(cyclohexylmethyl)-1,2,3,6-tetrahydro-2,6-dioxo-9H-purin-8-yl)cinnamic acid, from Example 31, (0.20 g, 0.41 mmol) in dichloromethane (5 ml) and thionyl chloride (Aldrich, 0.6 ml, 0.81 mmol) was refluxed for 1.5 hours. Volatiles were removed in vacuo to give (E)-3-(1,3-bis(cyclohexylmethyl)-1,2,3,6-tetrahydro-2, 6-dioxo-9H-purin-8-yl)cinnamic acid chloride as a yellow solid which was used without further purification.

(c) (E)-3-(1,3-bis(Cyclohexylmethyl)-1,2,3,6-tetrahydro-2,6-dioxo-9H-purin-8-yl)cinnamic Acid Nonaethylene Glycol Methyl Ether Amide To the intermediate from Example 67, part (b), was added dichloromethane (15 ml) and the reaction mixture stirred at 0° C. A solution of Amino nonaethyleneglycol methyl ether from part (a) of this Example (0.262 g, 0.49 mmol) and triethylamine (0.12 g, 1.22 mmol) in dichloromethane (5 ml) was added and the resulting solution was allowed to stir at room temperature for 1.5 hours. The solution was diluted with chloroform (100 ml) and washed with saturated aqueous sodium bicarbonate (20 ml), and saturated aqueous sodium chloride (20 ml). The organic layer was dried with magnesium sulfate filtered and evaporated to a yellow waxy solid. Elution from a silica gel column with 15% methanol-ethyl acetate gave the title compound as a yellow waxy solid which was dissolved in ethyl acetate (10 ml) and re-precipitated by addition of hexanes to give (E)-3-[1,3-bis(cyclohexylmethyl)-1,2,3,6-tetrahydro-2,6-dioxo-9H-purin-8-yl]cinnamic Acid Nonaethylene Glycol Methyl Ether Amide (0.167 g, 45%) as a waxy solid. $^1$H-NMR (300 MHz, DMSO-$d_6$) δ: 8.22 (t, J=5.5 Hz, 1H, NH), 8.13 (d, J=8.4 Hz, 2H, phenylCH), 7.68 (d, J=8.4 Hz, 2H, phenylCH), 7.44 (d, J=16 Hz, 1H, CH=), 6.73 (d, J=16.1 Hz, 1H, CH=), 3.99 (d, J=7.6Hz, 2H, CH$_2$N), 3.87 (d, J=7.6 Hz, 2H, CH$_2$N), 3.60–3.30 (m, 36H, 18CH$_2$), 3.20 (s, 3H, CH$_3$), 2.55–2.25 (m, 2H, 2CH), 1.80–1.20 (m, 12H, cyclopentyl CH$_2$'s).

Anal. Calcd For $C_{47}H_{73}N_5O_{12}$.1.06.$H_2O$: C, 61.41; H, 8.24; N, 7.62; Found: C, 61.41; H, 7.93; N, 7.65.

The compounds named in Table 3, below, were prepared by methods analogous to the method used above to prepare Example 67.

TABLE 3

| EX. | NAME | MASS SPEC/ METHOD | ANALYTICAL | SM |
|---|---|---|---|---|
| 68 | (E)-4-(1,3-Bis(cyclohexylmethyl)-1,2,3,6-tetrahydro-2,6-dioxo-9H-purin-8-yl)cinnamic Acid N-methyl Nonaethylene Glycol Methyl Ether Amide | | Calcd for $C_{48}H_{76}N_5O_{12}$.0.11.$H_2O$: C, 62.82; H, 8.25; N, 7.63; Found: C, 62.81; H, 8.35; N, 7.51 | Example 1 |
| 69 | (E)-4-(1,3-Bis(cyclohexylmethyl)-1,2,3,6-tetrahydro-2,6-dioxo-9H-purin-8-yl)cinnamic Acid Nonaethylene Glycol Methyl Ether Amide | 900 (M + H)$^+$; FAB | Calcd for $C_{47}H_{73}N_5O_{12}$.0.85.$H_2O$: C, 61.67; H, 8.22; N, 7.65; Found: C, 61.66; H, 8.07; N, 7.67 | Example 1 |
| 70 | (E)-4-[1,3-bis(benzyl)-1,2,3,6-tetrahydro-2,6-dioxo-9H-purin-8-yl]cinnamic Acid Nonaethylene Glycol Methyl Ether Amide | 888 (M + 1); ES+ | Calcd for $C_{47}H_{61}N_5O_{12}$.0.71.$H_2O$: C, 62.67; H, 6.98; N, 7.77; Found: C, 62.66; H, 6.84; N, 7.86 | Example 2 |
| 71 | (E)-4-(1,3-bis(cyclopentylmethyl)-1,2,3,6-tetrahydro-2,6-dioxo-9H-purin-8-yl)cinnamic Acid Nonaethylene Glycol Methyl Ether Amide | 872 (M + H)$^+$; FAB | Calcd for $C_{49}H_{69}N_5O_{12}$.0.95.$H_2O$: C, 60.79; H, 8.04; N, 7.88; Found: C, 60.79; H, 7.90; N, 7.94 | Example 3 |
| 72 | (E)-4-(1,3-bis(2-methylpropyl)-1,2,3,6-tetrahydro-2,6-dioxo-9H-purin-8-yl)cinnamic Acid Nonaethylene Glycol Methyl Ether Amide | 820 (M + 1); ES+ | Calcd for $C_{41}H_{65}N_5O_{12}$.0.88.$H_2O$: C, 58.92; H, 8.05; N, 8.38; Found: C, 58.92; H, 7.98; N, 8.54 | Example 10 |
| 73 | (E)-4-((1-propyl-3-cyclohexylmethyl)-1,2,3,6-tetrahydro-2,6-dioxo-9H-purin-8-yl)cinnamic Acid Nonaethylene Glycol Methyl Ether Amide | 846 (M + 1); ES+ | Calcd for $C_{41}H_{65}N_5O_{12}$.0.78.$H_2O$: C, 60.05; H, 8.03; N, 8.14; Found: C, 60.05; H, 7.89; N, 8.17 | Example 11 |
| 74 | (E)-4-((1-cyclohexylmethyl-3-propyl)-1,2,3,6-tetrahydro-2,6-dioxo-9H-purin-8-yl)cinnamic Acid Nonaethylene Glycol Methyl Ether Amide | 846 (M + H)$^+$; FAB | Calcd for $C_{43}H_{67}N_5O_{12}$.1.08.$H_2O$: C, 59.67; H, 8.05; N, 8.09; Found: C, 59.68; H, 7.93; N, 7.97 | Example 16 |
| 75 | 4-(1,3-Bis(cyclohexylmethyl)-1,2,3,6-tetrahydro-2,6-dioxo-9H-purin-8-yl)benzioc Acid Nonaethylene Glycol Methyl Ether Amide | 874 (M + H)$^+$; FAB | Calcd for $C_{46}H_{71}N_5O_{12}$.1.69.$H_2O$: C, 59.75; H, 8.29; N, 7.74; Found: C, 59.75; H, 8.10; N, 7.20 | Example 32 |
| 76 | 4-(1,3-Bis(cyclohexylmethyl)-1,2,3,6-tetrahydro-2,6- | 888 (M + H)$^+$; FAB | Calcd for $C_{46}H_{73}N_5O_{12}$.0.14.$H_2O$: C, 62.04; H, 8.29; N, | Example 32 |

TABLE 3-continued

| EX. | NAME | MASS SPEC/ METHOD | ANALYTICAL | SM |
|---|---|---|---|---|
| | dioxo-9H-purin-8-yl) benzoic Acid-N-methyl-Nonaethylene Glycol Methyl Ether Amide | | 7.86; Found: C, 62.03; H, 8.27; N, 7.85 | |

General Method for the Synthesis of N7-Substituted Xanthine Carboxylic Acid Esters and Amides Example 77

(E)-4-(1,3-bis(Cyclohexylmethyl)-2,3,6,7-tetrahydro-2,6-dioxo-7-benzyl-1H-purin-8-yl) cinnamic Acid Nonaethylene Glycol Methyl Ether Ester To (E)-4-(1,3-bis(cyclohexylmethyl)-1,2,3,6-tetrahydro-2,6-dioxo-9H-purin-8-yl)cinnamic Acid Nonaethylene Glycol Methyl Ether Ester (0.52 g, 0.6 mmol), from Example 35, N,N-dimethylformamide (10 mL) was added potassium carbonate (Aldrich, 0.17 g, 1.2 mmol) and benzyl bromide (Aldrich, 0.154 g, 0.9 mmol). This reaction mixture was stirred at room temperature for 12 hours. The reaction mixture was diluted with ethyl acetate and extracted with $H_2O$ (3x). The organic layer was dried over $MgSO_4$, filtered and concentrated under reduced pressure. The crude material was purified by silica gel flash chromatogrpahy (1% to 5% $MeOH/CHCl_3$ eluent) to yield the title compound (0.28 g, 87%) as a thick syrup. $^1$H-NMR (DMSO-$d_6$) δ: 7.84 (d, J=8.0 Hz, 2H), 7.68 (m, 3H), 7.23 (m, 3H), 6.97 (d, J=8.0 Hz, 2H), 6.76 (d, J=16 hz, 1H), 5.68 (s, 2H), 4.26 (m, 2H), 3.88 (d, J=7.0 Hz, 2H), 3.73–3.21 (m, 36H), 3.20 (s, 3H), 1.90 (br m, 1H), 1.55 (m, 11H), 1.07 (m, 10H); FAB-MS 991 $(M+H)^+$.

Anal. Calcd For $C_{54}H_{78}N_4O_{13} \cdot 0.5.H_2O$: C, 64.75; H, 7.97; N, 5.59; Found: C, 64.75; H, 7.74; N, 5.81.

The compounds named in Table 4, below, were prepared by methods analogous to the method used above to prepare Example 77.

TABLE 4

| EX. | NAME | MASS SPEC/ METHOD | ANALYTICAL | SM |
|---|---|---|---|---|
| 78 | (E)-4-(1,3-Bis(cyclohexylmethyl)-2,3,6,7-tetrahydro-2,6-dioxo-7-(2-oxo-2-phenylethyl)-1H-purin-8-yl)cinnamic Acid Nonaethylene Glycol Methyl Ether Ester | 1018 $(M + H)^+$; FAB | Calcd for $C_{55}H_{78}N_4O_{13} \cdot 0.95.H_2O$: C, 63.74; H, 7.77; N, 5.41; Found: C, 63.74; H, 7.55; N, 5.61 | Example 35 |
| 79 | (E)-4-(1,3-Bis(cyclohexylmethyl)-2,3,6,7-tetrahydro-2,6-dioxo-7-methyl-1H-purin-8-yl)cinnamic Acid Nonaethylene Glycol Methyl Ether Ester | 915 $(M + H)^+$; FAB | Calcd for $C_{48}H_{74}N_4O_{132} \cdot 0.4.H_2O$: C, 62.51; H, 8.17; N, 6.09; Found: C, 62.51; H, 8.05; N, 6.09 | Example 35 |
| 80 | (E)-4-(1,3-Bis(cyclohexylmethyl)-2,3,6,7-tetrahydro-2,6-dioxo-7-(2-propynyl)-1H-purin-8-yl)cinnamic Acid Nonaethylene Glycol Methyl Ether Ester | 938 $(M + H)^+$; FAB | Calcd for $C_{50}H_{74}N_4O_{13} \cdot 0.14.H_2O$: C, 63.77; H, 7.92; N, 5.97; Found: C, 63.77; H, 7.92; N, 6.08 | Example 35 |
| 81 | (E)-4-(1,3-Bis(cyclohexylmethyl)-2,3,6,7-tetrahydro-2,6-dioxo7-(2-oxo-2-methylethyl)-1H-purin-8-yl)cinnamic Acid Nonaethylene Glycol Methyl Ether Ester | 915 $(M + H)^+$; FAB | Calcd for $C_{50}H_{76}N_4O_{14} \cdot 1.23.H_2O$: C, 61.32; H, 8.08; N, 5.71; Found: C, 61.32; H, 7.69; N, 5.71 | Example 35 |
| 82 | (E)-4-(1,3-Bis(cyclohexylmethyl)-2,3,6,7-tetrahydro-2,6-dioxo-7-(4-morpholinylmethyl)-1H-purin-8-yl)cinnamic Acid Nonaethylene Glycol Methyl Ether Ester | 1028 $(M + H)^+$; FAB | Calcd for $C_{54}H_{85}N_5O_{14} \cdot 0.20.H_2O$: C, 62.85; H, 8.34; N, 6.79; Found: C, 62.85; H, 8.24; N, 6.70 | Example 35 |
| 83 | (E)-4-(1,3-Bis(cyclohexylmethyl)-2,3,6,7-tetrahdro-2,6-dioxo-7-ethyl-1H-purin-8-yl)cinnamic Acid Nonaethylene Glycol Methyl Ether Ester | 929 $(M + H)^+$; FAB | Calcd for $C_{49}H_{76}N_4O_{13} \cdot 0.21.H_2O$: C, 63.08; H, 8.26; N, 6.01; Found: C, 63.09; H, 8.22; N, 5.92 | Example 35 |
| 84 | (E)-4-(1,3-Bis(cyclohexylmethyl)-2,3,6,7-tetrahydro-2,6-dioxo-7-(2-ethoxy-2-oxoethyl)-1H-purin-8-yl)cinnamic Acid Nonaethylene Glycol Methyl Ether Ester | 987 $(M + H)^+$; FAB | Calcd for $C_{51}H_{78}N_4O_{15} \cdot 0.45.H_2O$: C, 61.55; H, 7.93; N, 5.63; Found: C, 61.54; H, 7.93; N, 5.55 | Example 35 |
| 85 | (E)-4-(1,3-Bis(cyclohexylmethyl)-2,3,6,7-tetrahydro-2,6-dioxo-7-propyl-1H-purin-8-yl)cinnamic | 943 $(M + H)^+$; FAB | Calcd for $C_{50}H_{78}N_4O_{13} \cdot 0.9.H_2O$: C, 63.47; H, 8.32; N, 5.92; | |

TABLE 4-continued

| EX. | NAME | MASS SPEC/ METHOD | ANALYTICAL | SM |
|---|---|---|---|---|
| | Acid Nonaethylene Glycol Methyl Ether Ester | | Found: C, 63.48; H, 8.33; N, 5.99 | |
| 86 | (E)-4-(1,3-Bis(cyclohexylmethyl)-2,3,6,7-tetrahydro-2,6-dioxo-7-(2-methyl-2-propenyl)-1H-purin-8-yl)cinnamic Acid Nonaethylene Glycol Methyl Ether Ester | 955 (M + H)$^+$; FAB | Calcd for $C_{51}H_{78}N_4O_{13}$·0.11.$H_2O$: C, 64.00; H, 8.24; N, 5.85; Found: C, 64.00; H, 8.20; N, 5.82 | Example 35 |
| 87 | (E)-4-(1,3-Bis(cyclohexylmethyl)-2,3,6,7-tetrahydro-2,6-dioxo-7-(cyanomethyl)-1H-purin-8-yl)cinnamic Acid Nonaethylene Glycol Methyl Ether Ester | 940 (M + 1); ES+ | Calcd for $C_{49}H_{73}N_5O_{13}$·0.5.$H_2O$/0.1.EtO Ac: C, 66.99; H, 7.87; N, 7.31; Found: C, 62.04; H, 7.71; N, 7.52 | Example 35 |
| 88 | 4-(1,3-Bis(cyclohexylemthyl)-2,3,6,7-tetrahydro-2,6-dioxo-7-bezyl-1H-purin-8-yl)benzoic Acid Nonaethylene Glycol methyl Ether Ester | 966 (M + H)$^+$; FAB | Calcd for $C_{52}H_{76}N_4O_{13}$·0.14.$H_2O$: C, 64.54; H, 7.95; N, 5.79; Found: C, 63.98; H, 7.785; N, 5.74 | Example 65 |
| 89 | 4-(1,3-Bis(cyclohexylmethyl)-2,3,6,7-tetrahydro-2,6-dioxo-7-methyl-1H-purin-8-yl)benzoic Acid Nonaethylene Glycol Methyl Ether Ester | 889 (M + H)$^+$; FAB | Calcd for $C_{46}H_{72}N_4O_{13}$·0.14.$H_2O$: C, 61.97; H, 8.17; N, 6.28; Found: C, 61.62; H, 8.12; N, 6.21 | Example 65 |
| 90 | 4-[(1,3-Bis(cyclohexylmethyl)-2,3,6,7-tetrahydro-2,6-dioxo-7-methyl-1H-purin-8-yl)phenyl] propionic Acid Nonaethylene Glycol Methyl Ether Ester | 917 (M + H)$^+$; FAB | Calcd for $C_{48}H_{76}N_4O_{13}$·0.11.$H_2O$: C, 62.73; H, 8.36; N, 6.10; Found: C, 62.73; H, 8.27; N, 5.95 | |
| 91 | (E)-4-(1,3-Bis(cyclohexylmethyl)-2,3,6,7-tetrahydro-2,6-dioxo-7-methyl-1H-purin-8-yl)cinnamic Acid Nonaethylene Glycol Methyl Ether Amide | 914 (M + H)$^+$; FAB | Calcd for $C_{48}H_{75}N_5O_{12}$·0.49.$H_2O$: C, 62.46; H, 8.30; N, 7.59; Found: C, 62.46; H, 8.20; N, 7.60 | Example 69 |
| 92 | (E)-4-(1,3-Bis(cyclohexylmethyl)-2,3,6,7-tetrahydro-2,6-dioxo-7-benzyl-1H-purin-8-yl)cinnamic Acid Nonaethylene Glycol Methyl Ether Amide | 990 (M + H)$^+$; FAB | Calcd for $C_{54}H_{79}N_5O_{12}$·1.95.$H_2O$: C, 63.25; H, 8.15; N, 6.83; Found: C, 63.26; H, 7.85; N, 6.68 | Example 69 |
| 93 | 4-(1,3-Bis(cyclohexylmethyl)-2,3,6,7-tetrahydro-2,6-dioxo-7-benzyl-1H-purin-8-yl)benzoic Acid Nonaethylene Glycol Methyl Ether Amide | 964 (M + H)$^+$; FAB | Calcd for $C_{52}H_{77}N_5O_{12}$·0.14.$H_2O$: C, 64.61; H, 8.06; N, 7.24; Found: C, 62.06; H, 7.70; N, 6.92 | Example 75 |
| 94 | 4-(1,3-Bis(cyclohexylmethyl)-2,3,6,7-tetrahydro-2,6-dioxo-7-methyl-1H-purin-8-yl)benzoic Acid Nonaethylene Glycol Methyl Ether Amide | 888 (M + H)$^+$; FAB | Calcd for $C_{46}H_{73}N_5O_{12}$· 0.14.$H_2O$: C, 62.04; H, 8.29; N, 7.86; Found: C, 61.20; H, 8.17; N, 7.66 | Example 75 |

Example 95

(E)-4-(1,3-bis(Cyclohexylmethyl)-1,2,3,6-tetrahydro-2,6-dioxo-9H-purin-8-yl)cinnamic Acid N,N-bis Triethylene Glycol Methyl Ether Amide (a) N,N-bis(Triethyleneglycolmonomethyl Ether)amine A mixture of triethylene glycol methyl tosyl ether from Example 33, part (a) (1.0 g, 3.14 mmol), potassium carbonate (Aldrich, 0.5 g, 10.8 mmol) and benzylamine (Aldrich, 0.168 g, 1.57 mmol) was stirred at 100° C. for 18 hours. Ethyl acetate (50 ml) was added to this mixture and the organic layer was washed with water, dried over magnesium sulfate and filtered. The volatiles were removed in vacuo and the residue eluted from a silica gel column with 10% methanol-chloroform. Concentration of the collected samples gave N,N-bis(triethyleneglycolmonomethyl ether) benzyl amine as a colorless oil (0.55 g). $^1$H-NMR DMSO-$d_6$) δ: 7.30–7.25 (m, 5H, $C_6H_5$), 4.10 (m, 2H, $CH_2$), 3.80–340 (m, 20H, 10–5 $CH_2$), 3.20 (s, 3H, $CH_3$) 2.60 (m, 4H, 2 $CH_2N$). This material was taken up in ethanol (50 ml) and a catalytic amount of 10% palladium on carbon (Aldrich, Degussa type) was added and this heterogeneous mixture was reacted under hydrogen (0.1 psi) for 18 hours. The catalyst was removed by filtration through a pad Celite and the volatiles were removed in vacuo to give N,N-bis (triethyleneglycolmonomethyl ether)amine which was used without further purification.

(b) (E)-4-(1,3-bis(Cyclohexylmethyl)-1,2,3,6-tetrahydro-2, 6-dioxo-9H-purin-8-yl)cinnamic Acid N,N-bis-Triethylene Glycol Methyl Ether Amide To (E)-4-(1,3-bis(cyclohexylmethyl)-1,2,3,6-tetrahydro-2,6-dioxo-9H-purin-8-yl)cinnamic acid chloride (0.25 g, 0.49 mmol) from the Example 66, part (b) above, in dichloromethane (10 ml) at 0° was added a solution of N,N-bis (triethyleneglycolmonomethyl ether)amine from Example 97, part (a) above, and triethylamine (0.15 g, 1.5 mmol) in dichloromethane (5 ml). The resulting solution was allowed to stir at room temperature for 2 hours. The mixture was diluted with chloroform (50 ml) and washed with saturated aqueous sodium bicarbonate (20 ml), saturated aqueous sodium chloride (20 ml), dried over magnesium sulfate and filtered. The volatiles were removed in vacuo and the crude material was purified by silica gel chromatography by elution with 15% methanol-ethyl acetate to provide the tide compound as a yellow solid (0.070 g, 18%). $^1$H-NMR (300 MHz DMSO-$d_6$) δ: 8.12 (d, J=8.3 Hz, 2H, phenylCH), 7.80 (d, J=8.2 Hz, 2H, phenylCH), 7.47 (d, J=15.3 Hz, 1H, CH=), 7.26 (d, J=15.5 Hz, 1H, CH=), 3.90 (d, J=7.1 Hz, 2H, CH$_2$N), 3.71 (d, J=7.6 Hz, overlapping m at 3.7, total 4H $_1$ CH$_2$N and CH$_2$O), 3.60–3.35 (m, 22H, 11 CH$_2$), 3.21 and 3.17 (2 s, 3 each, 2-CH$_3$), 2.05–1.50 and 1.30–0.95 (m, 22H, cyclopentyl CH$_2$'s).

Anal. Calcd For $C_{42}H_{63}N_5O_9$: C, 64.51; H, 8.12; N, 8.96; Found: C, 64.25; H, 8.00; N, 8.89.

Example 96

1,3-bis(Cyclohexylmethyl)-8-[4-(2,5,8,11,14,17,20, 23,26,29-decaoxatriacont-1-yl)phenyl]-3,7-dihydro-1H-purine-2,6-dione (a) Nonaethyleneglycol(4-carboxybenzyl)methyl Ether A solution of nonaethyleneglycol monomethyl ether (0.35 g, 0.82 mmol) from Example 33, part (a), 4-bromomethylbenzoic acid (Lancaster, 0.18 g, 0.82 mmol) and potassium carbonate (Aldrich, 0.23 g, 1.64 mmol) in tetrahydrofuran (20 ml) was stirred at reflux for 3 hours. The mixture was cooled to room temperature and sodium hydride (Aldrich, 0.065 g, 1.62 mmol as 60% dispersion in oil) was added. The mixture was allowed to reflux for an additional 2 hours and cooled to room temperature. The pH was adjusted to ~3.0 by addition of 1N hydrochloric acid, and the solution was diluted with chloroform (50 ml) and washed with water (25 ml). The organic layer was dried over magnesium sulfate and filtered. The volatiles were removed in vacuo to give nonaethyleneglycol(4-carboxybenzyl) methyl ether as an amber oil (0.45 g, 96%). $^1$H-NMR (300 MHz, DMSO-$d_6$) δ: 7.90 (d, J=8.1 Hz, 2H, 2 aryl CH), 7.42 (d, J=8.0 Hz, 2H, 2 aryl CH), 4.55 (s, 2H, CH$_2$), 3.60–3.20 (m, glycol CH$_2$'s, water and CH$_3$).

(b) 1,3-bis(Cyclohexylmethyl)-8-[4-(2,5,8,11,14,17,20,23, 26,29-decaoxatriacont-1-yl)phenyl]-3,7-dihydro-1H-purine-2,6-dione To a solution of nonaethyleneglycol(4-carboxybenzyl) methyl ether (0.45 g, 0.80 mmol) from Example 97 part (a) above, in dichloromethane (15 ml) was added oxalyl chloride (Fluka, 0.14 ml, 1.6 mmol) and N,N dimethylformamide (one drop). This solution was allowed to stir for 0.5 hours and the volatiles were removed in vacuo to give a tan oil. This material was dissolved in dichloromethane (20 ml) and a solution of triethylamine (0.5 ml, 3.8 mmol) and 1,3-bis(cyclohexylmethyl)-5,6-diaminouracil from Example 21, part (a), (0.270 g, 0.80 mmol) in dichloromethane (10 ml) were added. This solution was allowed to stir at room temperature for 18 hours and the volatiles were removed in vacuo. The residue was dissolved in ethanol (25 ml) and the pH was adjusted to ~13 by addition of 2N sodium hydroxide. The solution was allowed to stir at reflux for 0.5 hours and then cooled to room temperature. Chloroform (100 ml) was added and the solution was washed with 1N hydrochloric acid (50 ml), saturated aqueous sodium chloride (20 ml), dried over magnesium sulfate and filtered. The volatiles were removed in vacuo and the title compound was eluted from silica gel with 15% methanol-ethyl acetate as a tan waxy solid after solidification from ethyl acetate-hexanes (0.098 g, 14%). $^1$H-NMR (300 MHz, DMSO-$d_6$) δ: 8.07 (d, J=8.2 Hz, 2H, phenylCH), 7.44 (d, J=8.1 Hz, 2H, phenylCH), 4.54 (s, 2H, CH$_2$-phenyl), 3.89 (d, J=7.2 Hz, 2H, CH$_2$N), 3.70 (d, J=7.2 Hz, 2H, CH$_2$N ), 3.60–3.35 (m, 36H, 18CH$_2$), 3.20 (s, 3H, CH$_3$), 2.05–1.50 and 1.30–0.95 (m, 22H, cyclohexyl CH$_2$'s).

Anal. Calcd For $C_{45}H_{72}N_4O_{12}$: C, 62.77; H, 8.43; N, 6.51; Found: C, 62.43; H, 8.53; N, 6.68.

Example 97

(E)-4-(1,3-bis(Cyclohexylmethyl)-2,3,6,7-tetrahydro-2,6-dioxo-7-(triethylene Glycol Methyl Ether-1H-purin-8-yl)cinnamic Acid Triethylene Glycol Methyl Ether Ester (a) (E)-4-(1,3-bis(Cyclohexylmethyl)-1,2,3,6-tetrahydro-2,6-dioxo-9H-purin-8-yl]cinnamic Acid Methyl Ester In the manner of Example 36, part (b), (E)-4-[1,3-bis (cyclohexylmethyl)-1,2,3,6-tetrahydro-2,6-dioxo-9H-purin-8-yl]cinnamic acid was converted to (E)-1,3-bis (cyclohexylmethyl)-8-(3-(2-(1H-imidazol-1-ylcarbonyl) vinyl)phenyl)-9H-purin-2,6(1H,3H)-dione as a yellow powder. Such a sample (2.50 g, 4.62 mmol) was stirred at reflux in acetonitrile (75 ml) with potassium carbonate (1.28 g, 9.25 mmol) and methanol, (10 ml) for 24 hours. The mixture was cooled to room temperature and filtered and the filtrate-wash was adjusted to pH ~3 by addition of 6N hydrochloric acid. The resulting precipitate was filtered and washed with methanol and dried to give (E)-4-[1,3-bis (cyclohexylmethyl)-1,2,3,6-tetrahydro-2,6-dioxo-9H-purin-8-yl]cinnamic acid methyl ester (1.70 g, 74%) as a white solid. $^1$H-NMR (300 MHz, DMSO-$d_6$) δ: 8.16 (d, J=8.2 Hz, 2H, phenylCH), 7.83 (d, J=8.4 Hz, 2H, 2 phenylCH), 7.63 (d, J=15.9 Hz, 1H, CH=), 6.70 (d, J=15.9 Hz, 1H, CH—), 3.95 (d, J=7.0 Hz, 2H, CH$_2$N), 3.75 (d, J=6.8 Hz, 2H, CH$_2$N), 3.70 (s, 3H, CH$_3$), 2.0–1.50 and 1.20–0.80 (m, 22H, 2C$_6$H$_{11}$).

(b) (E)-4-(1,3-bis(Cyclohexylmethyl)-2,3,6,7-tetrahydro-2, 6-dioxo-7-(triethylene Glycol Methyl Ether-1H-purin-8-yl) cinnamic Acid Triethylene Glycol Methyl Ether Ester To a mixture of (E)-4-(1,3-bis(cyclohexylmethyl)-1,2,3, 6-tetrahydro-2,6-dioxo-9H-purin-8-yl)cinnamic acid methyl ester (0.25 g, 0.49 mmol) from part (a) above, triethylene glycol methyl tosyl ether (from Example 34, part (a), 0.158 g, 0.49 mmol) and potassium carbonate (Aldrich, 0.137 g, 0.99 mmol) in N,N-dimethylformamide (5 ml) was stirred at room temperature 24 hours. Additional triethylene glycol methyl tosyl ether (0.48 g) was added and the mixture stirred at 70° C. for three days. The mixture was diluted with ethyl acetate (20 ml) and washed with water and dried over magnesium sulfate and filtered. The volatiles were removed in vacuo and the crude material was purified by silica gel chromatography by elution with 10% methanol-chloroform to provide the title compound as a amber oil (0.100 g, 31%). $^1$H-NMR (300 MHz DMSO-$d_6$) δ: 7.90 (m, 4H, $C_6H_4$), 7.75 (d, J=15.3 Hz, 1H, CH=), 6.80 (d, J=15.5 Hz, 1H, CH=), 4.45 (m, 2H, CH$_2$O), 4.30 (m, 2H, CH$_2$O), 3.65 (m, 2H, CH$_2$O), 3.60–3.35 (m, overlapping H$_2$O, glycol CH$_2$'s), 3.21 and 3.17 (2 s, 3H each, 2-CH$_3$), 2.00–1.50 and 1.30–0.95 (m, 22H, cyclopentyl CH$_2$'s).

Anal. Calcd For $C_{42}H_{62}N_4O_{10}$: C, 64.43; H, 7.98; N, 7.15; Found: C, 64.11; H, 7.90; N, 7.12.

Example 98

(E)-3-5-[1,3-bis(Cyclohexylmethyl)-2,3,6,7-tetrahydro-2,6-dioxo-1H-purin-8-yl]-2-thienyl-2-propenoic Acid Nonaethylene Glycol Methyl Ether Ester (a) 5-(Methyl Propenoate)-2-thiophenecarboxylic Acid To 5-formyl-2-thiophenecarboxylic acid (TCl, 4.0 g, 26.0 mmol) in dichloromethane (100 mL) was added carbomethoxymethylene triphenylphosphorane (Lancaster, 12.8 g, 38.0 mmol) and this reaction mixture was allowed to stir at room temperature for 12 hours. The reaction was diluted with dichloromethane and washed with 10% aqueous sodium hydroxide and the layers separated. The aqueous layer was acidified (pH~2) with concentrated hydrochloric acid and extracted with ethyl acetate (×2). The organic layers were combined, dried over sodium sulfate, filtered and concentrated to give 5-(methyl propenoate)-2-thiophenecarboxylic acid (4.1 g, 75%). mp 154–156° C.; $^1$H-NMR (300 MHz, DMSO-d$_6$) δ: 13.34 (br s, 1H), 7.80 (d, J=15.7 Hz, 1H), 7.68 (d, J=4 Hz, 1H), 7.58 (d, J=15.7 Hz, 1H), 6.47 (d, J=15.7 Hz, 1H), 3.71 (s, 3H).

(b) 5-(Methyl Propenoate)-2-thiophenecarboxylic Acid Chloride

To 5-(methyl propenoate)-2-thiophenecarboxylic acid (2.0 g, 9.42 mmol) from part (a), was added thionyl chloride (Aldrich, 25 mL) and this reaction mixture was heated to reflux for 2 hours. The reaction mixture was cooled to room temperature and concentrated under reduced pressure to give the intermediate 5-(methyl propenoate)-2-thiophenecarboxylic acid chloride as a tan solid which was used without further purification.

(c) (E)-3-[5-[1,3-bis(Cyclohexylmethyl)-2,3,6,7-tetrahydro-2,6-dioxo-1H-purin-8-yl]-2-thienyl]-2-propenoic Acid To 1,3-bis(cyclohexylmethyl)-5,6-diaminouracil (1.45 g, 4.33 mmol), from Example 1, part (d), in dichloromethane (25 mL) was added the intermediate 5-(methyl propenoate)-2-thiophenecarboxylic acid chloride (1.0 g, 4.33 mmol) from part (b) above, and diisopropylethylamine (Aldrich, 0.84 g, 6.5 mmol). This reaction mixture was stirred at room temperature for 4 hours. The reaction mixture was concentrated under reduced pressure and the crude material was taken up in 1N sodium hydroxide and heated to reflux for 3 hours. The reaction mixture was cooled to room temperature, diluted with acetic acid and the product precipitated from the reaction mixture to provide (E)-3-[5-[1,3-bis(cyclohexylmethyl)-2,3,6,7-tetrahydro-2,6-dioxo-1H-purin-8-yl]-2-thienyl]-2-propenoic Acid (0.503 g, 23%) as a light green solid. mp >300° C.; $^1$H-NMR (300 MHz, DMSO-d$_6$) δ: 7.68 (d, J=15.7 Hz, 1H), 7.60 (br s, 1H), 7.45 (d, J=3.7 Hz, 1H), 6.18 (d, J=15.7 Hz, 1H), 3.78 (d, J=7.3 Hz, 2H), 3.73 (d, J=7.1 Hz, 2H), 1.89–1.40 (m, 12H), 1.20–0.90 (m, 10H).

(d) (E)-3-[5-[1,3-bis(Cyclohexylmethyl)-2,3,6,7-tetrahydro-2,6-dioxo-1H-purin-8-yl]-2-thienyl]-2-propenoic Acid Nonaethylene Glycol Methyl Ether Ester In the manner of Example 34, (E)-3-[5-[1,3-bis(cyclohexylmethyl)-2,3,6,7-tetrahydro-2,6-dioxo-1H-purin-8-yl]-2-thienyl]-2-propenoic Acid (0.30 g, 0.6 mmol) from part (c) above, was coupled to nonaethylene glycol methyl ether alcohol (0.26 g, 0.6 mmol) to provide the title compound as a waxy solid (75 mg, 14%). $^1$H-NMR (300 MHz, DMSO-d$_6$) δ: 8.03 (d, J=3.9 Hz, 1H), 7.80 (d, J=15.7 Hz, 1H), 7.28 (d, J=3.9 Hz, 1H), 6.39 (d, J=15.7 Hz, 1H), 3.72 (m, 2H), 4.02 (dd, J=13.0, 7.4 Hz, 4H), 3.86–3.76 (m, 36H), 3.36 (s, 3H), 2.02–1.66 (m, 12H), 1.14 (m, 10H); FAB-MS 907 (M+H)$^+$.

Anal. Calcd For C$_{45}$H$_{70}$N$_4$O$_{13}$.0.19 H$_2$O: C, 59.36; H, 7.78; N, 6.18; Found: C, 59.36; H, 7.78; N, 6.12.

Example 99

6-(1,3-bis(Cyclohexylmethyl)-1,2,3,6-tetrahydro-2,6-dioxo-9H-purin-8-yl)nicotinic Acid Nonaethylene Glycol Methyl Ether Amide (a) 5-(Methoxycarbonyl)pyridine-2-carboxylic Acid Chloride To 5-(Methoxycarbonyl)pyridine-2-carboxylic acid (Maybridge, 1.0 g, 5.52 mmol) was added thionyl chloride (Aldrich, 25 mL) and this reaction mixture was heated to reflux for 2 hours. The reaction mixture was cooled to room temperature and concentrated under reduced pressure to give the intermediate 5-(methoxycarbonyl)pyridine-2-carboxylic acid chloride as a tan solid which was used without further purification.

(b) 6-(1,3-bis(Cyclohexylmethyl)-1,2,3,6-tetrahydro-2,6-dioxo-9H-purin-8-yl)nicotinic Acid To 1,3-bis(cyclohexylmethyl)-5,6-diaminouracil (1.45 g, 4.33 mmol), from Example 1, part (d) above, in dichloromethane (25 mL) was added the intermediate 5-(methoxycarbonyl)pyridine-2-carboxylic acid (1.78 g, 5.52 mmol) and diisopropylethylamine (Aldrich, 0.84 g, 6.5 mmol). This reaction mixture was stirred at room temperature for 4 hours. The reaction mixture was concentrated under reduced pressure and the crude material was taken up in 1N sodium hydroxide and heated to reflux for 3 hours. The reaction mixture was cooled to room temperature, diluted with acetic acid and the product precipitated from the reaction mixture to provide 6-(1,3-Bis(cyclohexylmethyl)-1,2,3,6-tetrahydro-2,6-dioxo-9H-purin-8-yl)nicotinic Acid (1.44 g, 56%) as a green solid. $^1$H-NMR (300 MHz, DMSO-d$_6$) δ: 9.68 (s, 1H), 9.10 (d, J=3.1 Hz, 1H), 8.43 (m, 1H), 8.12 (m, 1H), 6.71 (br s, 1H), 4.12–3.60 (br m, 4H), 1.80–1.40 (m, 11H), 1.35–0.91 (m, 11H).

(c) 6-(1,3-bis(Cyclohexylmethyl)-1,2,3,6-tetrahydro-2,6-dioxo-9H-purin-8-yl)nicotinic Acid Nonaethylene Glycol Methyl Ether Amide In the manner of Example 67, 6-(1,3-Bis(cyclohexylmethyl)-1,2,3,6-tetrahydro-2,6-dioxo-9H-purin-8-yl)nicotinic Acid (0.56 g, 1.2 mmol) from part (b), was coupled to Aminononaethyleneglycol monomethyl ether (0.512 g, 1.2 mmol) to provide the title compound as a brown syrup (45 mg, 5%). $^1$H-NMR (300 MHz, DMSO-d$_6$) δ: 9.08 (s, 1H), 8.87 (t, J=5.0 Hz, 1H), 8.20 (d, J=8.1 Hz, 1H), 3.91 (d, J=7.1 Hz, 2H), 3.76 (d, J=7.1 Hz, 2H), 3.64–3.14 (m, 41H), 1.93 (br m, 1H), 1.89–1.57 (br m, 11H), 1.19–0.98 (br m, 10H).

Anal. Calcd for C$_{44}$H$_{70}$N$_6$O$_{12}$.0.50.H$_2$O: C, 59.78; H, 8.09; N, 9.51; Found: C, 59.78; H, 8.19; N, 9.45.

Example 100

(E)-4-(1,3-bis(Cyclohexylmethyl)-1,2,3,6-tetrahydro-2,6-dioxo-9H-purin-8-yl)cinnamic Acid N-cyclopronylmethyl Nonaethylene Glycol Methyl Ether Amide A solution of nonaethyleneglycolmonomethylether methane sulfonate (example 67, part a) (1.0 g, 1.97 mmol) in tetrahydrofuran (15 ml) and triethylamine (4.2 ml, 29.6 mmol) was refluxed with (aminomethyl)cyclopropane (Aldrich, 2.11 g, 19.7 mmol) for 24 hours. Additional (aminomethyl)cyclopropane was added (2.11 g) and reflux continued for an additional 8 hours. Volatiles were removed in vacuo and the residual oil was dissolved in tetrahydrofuran (10 ml) and triethyl amine (0.65 ml, 4.9 mmol). (E)-3-(1,3-bis(cyclohexylmethyl)-1,2,3,6-tetrahydro-2,6-dioxo-9H-purin-8-yl)cinnamic acid chloride (example 67, part b, 0.50 g, 0.98 mmol) was added and the resulting mixture was stirred at room temperature overnight The reaction was diluted with chloroform (100 ml), washed with saturated aqueous sodium bicarbonate solution (2×50 ml), and brine (25 ml). Volatiles were removed in vacuo and the residue was chromatographed on silica gel. The title compound eluted in 10% methanol-chloroform as a yellow waxy solid, (0.260 g) $^1$H-NMR (300 MHz, DMSO-d$_6$) δ: 8.2 (m, 2H, phenyl CH), 7.80 (m, 2H, phenyl CH), 7.50 (m, 1H, CH=), 7.3 (m, 1H, CH=), 3.85 (m, 2H, CH$_2$N), 3.70 (m, 2H, CH$_2$N), 3.60 (m, 2H, CH$_2$N), 3.55–3.35 (m, 36H, 18CH$_2$), 3.40 (s, 3H, CH$_3$), 2.0 (m, 1H, CH), 1.80 (m, 1H, CH), 1.80–1.20 (m, 20H, 10 CH$_2$).

Anal. Calcd For $C_{51}H_{71}N_5O_{12}$·1.1.$H_2O$·2.0 $C_4H_8O_2$: C, 61.62; H, 8.52; N, 6.10. Found: C, 61.52; H, 8.37; N, 6.10.

Example 101

(E)-4-(1,3-bis(Cyclohexylmethyl)-1,2,3,6-tetrahydro-2,6-dioxo-9H-purin-8-yl)cinnamic Acid Hexaethylene Glycol Benzyl Ether Amide (a) Amino Hexaethylene Glycol Benzyl Ether Triethylamine (1.45 mL, 10.74 mmol) and methanesulfonyl chloride (0.48 mL, 5.9 mmol) were added to a solution of hexaethyleneglycol monobenzyl ether (2.0 g, 5.37 mmol) in methylene chloride (30 mL) at 0° C. and the solution was stirred for 30 min at ice bath temperature. The reaction mixture was filtered and concentrated to an oil which was dissolved in 30% ammonium hydroxide solution (50 mL). The reaction mixture was heated at reflux for 3 days and concentrated. Residual water was removed by evaporation from toluene and the crude material was slurried with THF and filtered. The filtrate was concentrated at reduced pressure to provide the title compound as an amber oil (1.14 g, 57% yield). $^1$H-NMR (300 MHz DMSO-$d_6$) δ: 7.77 (br s, 2H), 7.40–7.10 (m, 5H), 4.48 (s, 2H), 3.61–3.48 (m, 24H).

(b) (E)-4-(1,3-bis(Cyclohexylmethyl)-1,2,3,6-tetrahydro-2,6-dioxo-9H-purin-8-yl)cinnamic Acid Hexaethylene Glycol Benzyl Ether Amide Amino hexaethyleneglycol benzyl ether (Example 101a) and the title compound of Example 1 were reacted using the procedures of examples 67b and 67c to provide the title compound as a waxy solid (34 mg, 10% yield); $^1$H NMR (400 MHz, DMSO-$d_6$) δ: 8.24 (t, J=5.5 Hz, 1H), 8.14 (d, J=8.2 Hz, 2H), 7.69 (d, J=8.2 Hz, 2H), 7.45 (d, J=15.8 Hz, 1H), 7.34–7.25 (m, 5H), 6.75 (d, J=15.8 Hz, 1H), 4.46 (s, 2H), 3.91 (br d, J=7.2 Hz, 2H), 3.78 (br d, J=7.2 Hz, 2H), 3.52–3.42 (m, 24H), 1.92 (m, 1H), 1.74 (m, 1H), 1.65–1.54 (m, 10H), 1.14–0.97 (m, 10H).

Anal. Calcd for $C_{47}H_{65}N_5O_9$·0.55.$H_2O$: C, 66.88; H, 7.76; N, 8.30. Found: C, 66.11; H, 7.69; N, 8.19.

Example 102

(E)-4-[(3-Cyclohexylmethyl)-1,2,3,6-tetrahydro-2,6-dioxo-9H-purin-8-yl]cinnamic Acid In the manner of Example 1, the title compound was synthesized as an off-white solid (6.75 g); $^1$H-NMR (300 MHz, DMSO-$d_6$) δ: 11.1 (s, 1H, NH), 8.10 (d, J=8.2 Hz, 2H, phenyl CH), 7.79 (d, J=7.3 Hz, 2H, phenyl CH), 7.59 (d, J=15.9 Hz, 1H, CH=), 6.59 (d, J=16 Hz, 1H, CH=), 3.82 (d, J=7.1 Hz, 2H, $CH_2$N), 1.90 (m, 1H, CH), 1.80–1.50 and 1.20–0.90 (m, 10H, 5 $CH_2$).

Example 103

(E)-4-[(Cyclohexylmethyl)-2,3,6,7-tetrahydro-2,6-dioxo-7-methyl-1H-purin-8-yl]cinnamic Acid Heptaethylene Glycol Methyl Ether Ester (a) (E)-4-[(3 Cyclohexylmethyl)-1,2,3,6-tetrahydro-2,6-dioxo-9H-purin-8-yl]cinnamic Acid Heptaethylene Glycol Methyl Ether Ester This compound was prepared from heptaethylene glycol monomethyl ether (Heimann, U.; Voegtle, F. Liebigs Ann. Chem. 1980, 6, 858–862) and the title compound of Example 102 using methods similar to those described in Example 34b and was obtained as a waxy solid (100 mg, 6% yield). $^1$H-NMR (400 MHz, DMSO-$d_6$) δ: 11.25 (s, 1H), 8.22 (d, J=8.4 Hz, 2H), 7.96 (d, J=8.4 Hz, 2H), 7.79 (d, J=16 Hz, 1H), 6.86 (d, J=16 Hz, 1H), 4.36 (m, 2H), 3.93 (m, 2H), 3.77 (m, 2H), 3.60–3.40 (m, 24H), 3.30 (s, 3H), 2.00 (1H, m), 1.70 (m, 5H), 1.24–1.10 (m, 5H). MS (ES–): 715 (M–1).

(b) (E)-4-[(3-Cyclohexylmethyl)-2,3,6,7-tetrahydro-2,6-dioxo-7-methyl-1H-purin-8-yl]cinnamic Acid Heptaethylene Glycol Methyl Ether Ester To a solution of the title compound from Example 103a (98 mg, 0.137 mmol) in DMF (2 mL) was added potassium carbonate (38 mg, 0.27 mmol) and methyl iodide (13 μL, 0.2 mmol) and the reaction mixture was stirred at room temperature overnight and at 60° C. for 2 h. The solvent was removed at reduced pressure and the resulting material was partitioned between dichloromethane and 1N hydrochloric acid. The organic layer was dried, filtered and concentrated and the crude product purified by flash chromatography on silica gel eluting with 10% methanol-ethyl acetate. The title compound was obtained as a waxy solid (10 mg, 10% yield). $^1$H-NMR (400 MHz, DMSO-$d_6$) δ: 11.17 (s, 1H), 7.95 (d, J=8.2 Hz, 2H), 7.86 (d, J=8.2 Hz, 2H), 7.77 (d, J=16 Hz, 1H), 4.31 (m, 2H), 4.02 (s, 3H), 3.83 (m, 2H), 3.71 (m, 2H), 3.58–3.42 (m, 24H), 3.24 (s, 3H), 1.91 (m, 1H), 1.64 (m, 5H), 1.25–1.04 (m, 5H). MS (ES+): 731 (M+1).

Example 104

(E)-4-[(3-Cyclohexylmethyl)-2,3,6,7-tetrahydro-2,6-dioxo-7-methyl-1H-purin-8-yl]cinnamic Acid Nonaethylene Glycol Methyl Ether Ester (a) (E)-4-[(3-Cyclohexylmethyl)-1,2,3,6-tetrahydro-2,6-dioxo-9H-purin-8-yl]cinnamic Acid Nonaethylene Glycol Methyl Ether Ester This compound was prepared from nonaethylene glycol monomethyl ether (Example 34a) and the title compound of Example 102 using methods similar to those described in Example 34b and was obtained as a waxy solid (1.3 g, 66% yield). $^1$H-NMR (400 MHz, DMSO-$d_6$) δ: 13.91 (s, 1H), 11.16 (s, 1H), 8.13 (d, J=8.4 Hz, 2H), 7.87 (d, J=8.4 Hz, 2H), 7.69 (d, J=16 Hz, 1H), 4.27 (m, 2H), 3.85 (m, 2H), 3.67 (m, 2H), 3.55–3.40 (m, 32H), 3.21 (s, 3H), 1.92 (m, 1H), 1.63 (m, 5H), 1.30–0.98 (m, 5H).

(b) (E)-4-[(3-Cyclohexylmethyl)-2,3,6,7-tetrahydro-2,6-dioxo-7-methyl-1H-purin-8-yl]cinnamic Acid Nonaethylene Glycol Methyl Ether Ester This compound was prepared from the product of Example 104a and methyl iodide using methods similar to those described in Example 103b and was obtained as a waxy solid (450 mg, 68% yield). $^1$H-NMR (400 MHz, DMSO-$d_6$) δ: 11.16 (s, 1H), 7.92 (d J=8.4 Hz, 2H), 7.83 (d, J=8.4 Hz, 2H), 7.73 (d, J=16 Hz, 1H), 6.80 (d, J=16 Hz, 1H), 4.28 (m, 2H), 3.99 (s, 3H), 3.79 (m, 2H), 3.68 (m, 2H), 3.56–3.38 (m, 32H), 3.21 (s, 3H), 1.87 (m, 1H), 1.60 (m, 5H), 1.13–0.98 (m, 5H). MS (ES–): 817 (M–1).

Anal. Calcd for $C_{41}H_{62}N_4O_{13}$·0.5.$H_2O$: C, 59.48; H, 7.67; N, 6.77. Found: C, 59.45; H, 7.51; N, 6.71.

Example 105

(E)-4-[(3-Cyclohexylmethyl)-2,3,6,7-tetrahydro-2,6-dioxo-1,7-dimethyl-1H-purin-8-yl]cinnamic Acid Nonaethylene Glycol Methyl Ether Ester Title compound was prepared from the product of Example 104b and methyl iodide in DMF at 75° C. using methods similar to those described in Example 103b and was obtained as a waxy solid (62 mg, 46% yield). $^1$H-NMR (400 MHz, DMSO-$d_6$) δ: 7.92 (d, J=8.4 Hz, 2H), 7.83 (d, J=8.4 Hz, 2H), 7.73 (d, J=16 Hz, 1H), 6.80 (d, J=16 Hz, 1H), 428 (m, 2H), 4.02 (s, 3H), 3.87 (m, 2H), 3.67 (m, 2H), 3.56–3.39 (m, 32H), 3.24 (s, 3H), 3.21 (s, 3H), 1.97 (m, 1H), 1.60 (m, 5H), 1.17–0.99 (m, 5H). MS (ES+): 833 (M+1).

Anal. Calcd for $C_{42}H_{64}N_4O_{13}$: C, 60.56; H, 7.74; N9 6.73. Found: C, 60.33; H, 7.64; N, 6.76.

Example 106

4-[1,3-bis(Cyclohexylmethyl)-1,2,3,6-tetrahydro-2,6-dioxo-9H-purin-8-yl]benzylamine N-Heptaethylene Glycol Methyl Ether

(a) 4-[1,3-bis(Cyclohexylmethyl)-1,2,3,6-tetrahydro-2,6-dioxo-9H-purin-8-yl]benzaldehyde 1,3-Bis(cyclohexylmethyl5,6-diaminouracil (143.5 mmol) was freshly prepared as described in Example 1d and dissolved in absolute ethanol (1 L). Terepthaldehyde monodiethylacetal (Aldrich, 28.54 ml, 143.5 mmol) was added and the solution was stirred at room temperature for 3 h. The reaction mixture was concentrated at reduced pressure, and residual ethanol was removed by evaporation from dimethoxyethane (400 ml). The resulting yellow solid was dissolved in dimethoxyethane (1 L) and iodine crystals (40.06 g, 157.85 mmol) were added. The reaction mixture was stirred at 50° C. for 4 h and at room temperature overnight. Saturated $Na_2S_2O_3$ (300 ml) was added and the dimethoxyethane was removed at reduced pressure. The resulting solid was collected by filtration and combined with methanol (300 ml), $H_2O$ (100 ml) and conc. Hydrochloric acid (3 ml). After heating at reflux for ten minutes, the solids were collected by filtration and dried to provide the title compound as a tan solid (53.05 g, 82% yield). $^1$H-NMR (400 MHz, DMSO-$d_6$) δ: 14.13 (s, 1H), 10.05 (s, 1H), 8.31 (d, J=8.2 Hz, 2H), 8.03 (d, J=8.2 Hz, 2H), 3.91 (br d, J=7 Hz, 2H), 3.77 (br d, J=7 Hz, 2H), 1.93 (m, 1H), 1.74 (m, 1H), 1.60 (m, 10H), 1.20–0.90 (m, 10H). MS (ES–): 447 (M–1).

(b) Amino Heptaethylene Glycol Methyl Ether Methanesulfonic Acid Salt

This compound was prepared from heptaethylene glycol monomethyl ether (Heimann, U.; Voegtle, F. Liebigs Ann. Chem. 1980, 6, 858–862), methanesulfonyl to chloride and ammonium hydroxide using methods similar to those described in Example 101a. The crude product was obtained as a white solid and was used without further purification (2.19, 96% yield). $^1$H-NMR (400 MHz, DMSO-$d_6$) δ: 7.3 (br s, 3H), 3.60–3.35 (m, 28H), 3.21 (s, 3H), 2.31 (s, 3H).

(c) 4-[1,3-bis(Cyclohexylmethyl)-1,2,3,6-tetrahydro-2,6-dioxo-9H-purin-8-yl]benzylamine N-Heptaethylene Glycol Methyl Ether To a mixture of the product of Example 106a (908 mg, 2.01 mmol) and the product of Example 106b (1.1 g, 2.53 mmol) in N,N-dimethyformamide (20 mL) was added sodium triacetoxyborohydnde (639 mg, 3.02 mmol). The reaction mixture was stirred at room temperature overnight, concentrated at reduced pressure and the resulting crude material partitioned between methylene chloride and $NaHCO_3$ solution. After separating the two phases, the methylene chloride layer was dried, filtered and concentrated. Flash chromatographic purification on silica gel eluting with 5% methanol-methylene chloride provided the title compound as a waxy solid (95 mg, 6% yield). $^1$H-NMR (400 MHz, DMSO-$d_6$) δ: 8.07 (d, J=8.2 Hz, 2H), 7.50 (d, J=8.2 Hz, 2H), 3.90 (m, 4H), 3.76 (br d, J=7 Hz, 2H), 3.59–3.36 (m, 26H), 3.21 (s, 3H), 2.78 (m, 2H), 1.91 (m, 1H), 1.73 (m, 11H), 1.64–1.53 (m, 10H), 1.20–0.95 (m, 10H). MS (ES+): 772 (M+1).

Anal. Calcd for $C_{41}H_{65}N_5O_9 \cdot 1.2.H_2O$: C, 62.05; H, 8.56; N, 8.82. Found: C, 61.97; H, 8.47; N, 8.78.

Example 107

4-[1,3-bis(Cyclohexylmethyl)-1,2,3,6-tetrahydro-2,6-dioxo-9H-purin-8-yl]benzylamine N-Heptaethylene Glycol Methyl Ether Hydrochloride

The title compound from Example 106 (41 mg, 0.053 mmol) was dissolved methylene chloride (ca. 1 mL) and a 1M solution of hydrochloric acid in diethyl ether (ca. 2 mL) was added. The reaction mixture was concentrated at reduced pressure to yield the title compound as a hydroscopic foam (41 mg, 96% yield). $^1$H-NMR (400 MHz, DMSO-$d_6$) δ: 13.88 (s, 1H), 9.19 (br s, 2H), 8.13 (d, J=8 Hz, 2H), 7.65 (d, J=8 Hz, 2H), 4.21 (m, 2H), 3.89 (br d, J=7 Hz, 2H), 3.76 (br d, J=7 Hz, 2H), 3.69 (m, 2H), 3.55–3.37 (m, 24H), 3.20 (s, 3H), 3.08 (m, 2H), 1.91 (m, 1H), 1.73 (m, 1H), 1.70–1.50 (m, 10H), 1.20–0.90 (m, 10H). MS (ES+): 772 (M+1).

Anal. Calcd for $C_{41}H_{65}N_5 9 \cdot (2.H_2O) \cdot (2.HCl)$: C, 55.90; H, 8.12; N, 7.95; Cl, 8.05. Found: C, 56.10; H, 7.74; N, 7.59; Cl, 7.82.

Example 108

4-[1,3-bis(Cyclohexylmethyl)-1,2,3,6-tetrahydro-2,6-dioxo-9H-purin-8-yl]benzylamine N-Nonaethylene Glycol Methyl Ether

Title compound was prepared from the product of Example 106a and amino nonaethylene glycol methyl ether (Example 67a) using methods similar to those described in Example 106c and was isolated as a waxy solid (50 mg, 4% yield). $^1$H-NMR (400 MHz, DMSO-$d_6$) δ: 8.05 (d, J=8 Hz, 2H), 7.46 (d, J=8Hz, 2H), 3.90 (br d, J=7.2 Hz, 2H), 3.80 (m, 2H), 3.77 (br d, J=7.3 Hz, 2H), 3.40 (m, 4H), 3.22 (s, 3H), 2.68 (br t, J=5.4 Hz, 2H), 3.50–3.40 (m, 26H), 1.92 (m, 1H), 1.76 (m, 1H), 1.70–1.50 (m, 10H), 1.20–0.90 (m, 10H). MS (ES+): 860 (M+1).

Anal. Calcd for $C_{45}H_{73}N_5O_{11} \cdot (1.1.H_2O)$ C, 61.42; H, 8.61; N, 7.96. Found: C, 61.69; H, 8.69; N, 7.57.

Example 109

4-[1,3-bis(Cyclohexylmethyl)-8-[26-methoxy-3,6,9,12,15,18,21,24(octaoxahexacosyloxy)phenyl]-3,7-dihydro-1H-purine-2,6-dione

(a) 4-[26-Methoxy-3,6,9,12,15,18,21,24 (octaoxahexacosyloxy)benzaldehyde

[3,3-Dimethyl-1,2,5-thiadiazolidine-1,1-dioxidato(2)-N5]triphenylphosphorus (Castro, J. L.; Matassa, V. G. J. Org. Chem. 1994, 59, 2289–2291) (1.07 g, 2.61 mmol) was added to a solution of 4-hydroxybenzaldehyde (214 mg, 1.75 mmol) in methylene chloride (75 mL) and the solution was stirred at room temperature overnight. The solvent was removed at reduced pressure and the crude material was purified by flash chromatography on silica gel eluting with 5–10% methanol-ethyl acetate which provided the title compound as an oil (0.79 g, 85% yield). $^1$H-NMR (400 MHz, CDCl$_3$) δ: 9.92 (s, 1H), 7.86 (d, J=8.7 Hz, 2H), 7.05 (d, J=8.7 Hz, 2H), 4.25 (m, 2H), 3.92 (m, 2H), 3.59 (m, 2H), 3.80–3.60 (m, 30H), 3.41 (s, 3H). MS (ES+): 555 (M+Na$^+$).

(b) 4-[1,3-bis(Cyclohexylmethyl)-26-methoxy-3,6,9,12,15,18,21,24(octaoxahexaoosyloxy)phenyl)-3,7-dihydro-1H-purine-2,6-dione 1,3-Bis(cyclohexylmethyl)-5,6-diaminouracil (250 mg, 0.75 mmol), freshly prepared as described in Example 1d, and the product from Example 109a (400 mg, 0.75 mmol) were dissolved in toluene (2.5 mL) and the solution heated at reflux overnight with azeotropic removal of water. The solution was concentrated and the crude material dissolved in dimethoxyethane (4 μL) and treated with iodine (190 mg, 0.75 mmol). The dark reaction mixture was heated at 50° C. overnight and then quenched with saturated $Na_2S_2O_3$ solution and extracted with methylene chloride. The methylene chloride layer was concentrated and the crude product purified by flash chromatography on silica gel eluting with 2% methanol-methylene chloride to provide the title compound as a waxy solid (280 mg, 44% yield). $^1$H-NMR (400 MHz, CDCl$_3$) δ: 12.24 (br s, 1H), 8.11 (d, J=8.8 Hz, 2H), 7.01 (d, J=8.8 Hz, 2H), 4.18 (t, J=5 Hz, 2H), 4.02 (d, J=7.3 Hz, 2H), 3.94 (d, J=7.4 Hz, 2H), 3.87 (t, J=5 Hz, 2H), 3.71 (m, 2H), 3.66 (m, 2H), 3.63–3.58 (m, 26H), 3.50 (m, 2H), 3.33 (s, 3H), 2.02 (m, 1H), 1.85 (m, 1H), 1.70–1.55 (m, 10H), 1.25–4.95 (m, 10H). MS (ES+): 847 (M+1).

Anal. Calcd for $C_{44}H_{70}N_4O_{12}\cdot(0.5H_2O)$ C, 61.73; H, 8.36; N, 6.54; Found: C, 61.65; H, 8.27; N, 6.61.

Example 110

1,3-bis(Cyclohexylmethyl)-8-[3-(2,5,8,11,14,17,20,23,26,29-decaoxatriacont-1-yl)phenyl]-3,7-dihydro-1H-purine-2,6-dione A solution of nonaethyleneglycol monomethyl ether (0.25 g, 0.58 mmol) from Example 33, part (a), 3-chloromethylbenzoic acid (Aldrich, Q.10 g, 0.58 mmol) and sodium hydride (Aldrich, 0.052 g, 1.28 mmol as 60% dispersion in oil) with catalytic sodium iodide (1.0 mg) was allowed to reflux 24 hours and cooled to room temperature. The pH was adjusted to ~3.0 by addition of 1N hydrochloric acid, and the volatiles were removed in vacuo. To the residue was added a solution of oxalyl chloride (Fluka, 0.53 ml, 5.8 mmol) and N,N-dimethylformamide (one drop) in methylene chloride (20 mL). The resulting mixture was stirred for 1.5 hours and the volatiles were removed in vacuo to leave a tan semisolid. This material was stirred in dichloromethane (20 ml) and a solution of triethylamine (0.4 ml, 2.86 mmol) and 1,3-bis(cyclohexylmethyl)-5,6-diaminouracil from Example 21, part (a), (0.193 g, 0.58 mmol) in dichloromethane (10 ml) was added. The solution stirred at room temperature for 1 h and the volatiles evaporated in vacuo. The residue was dissolved in ethanol (20 ml) and the pH was adjusted to ~13 by addition of 1N sodium hydroxide. The solution was refluxed for 0.5 hours, cooled to room temperature, and the pH adjusted to 5.0 by addition of 1N hydrochloric acid. The mixture was partitioned between water (25 ml) and chloroform (100 ml), and the aqueous layer was washed with additional chloroform (25 ml). The combined organic layers were washed with saturated aqueous sodium chloride (20 ml), dried over magnesium sulfate, and filtered. Volatiles were removed in vacuo and the residue chromatographed on silica gel. Title compound was eluted with 5% methanol-chloroform as a yellow waxy solid, after solidification from chloroform-hexanes (0.090 g, 17%); $^1$H-NMR (300 MHz, DMSO-d$_6$) δ: 8.08–7.98 m, 2H phenyl CH) 7.5–7.38 (m, 2H, phenyl CH), 4.5 (s, 2H, CH$_2$-phenyl), 3.85 (d, J=7.2 Hz, 2H, CH$_2$N), 3.75 (d, J=7.2 Hz, 2H, CH$_2$N), 3.60–3.35 (m, 36H, 18CH$_2$), 3.20 (s, 3H, CH$_3$), 2.05–1.50 and 1.30–0.95 (m, 22H 2 cyclohexyl).

Anal. Calcd For $C_{45}H_{72}N_4O_{12}$: 0.86 H$_2$O C, 61.66; H, 8.48; N, 6.39. Found: C, 61.66; H, 8.37; N, 6.81.

Example 111

(E-4-(1,3-bis(Cyclohexylmethyl)-2,3,6,7-tetrahydro-2,6-dioxo-7-methyl-1H-purin-8-yl)cinnamic Acid Heptaethylene Glycol Methyl Ether Ester (a) (E)-4-(1,3-bis(Cyclohexylmethyl)-1,2,3,6-tetrahydro-2,6-dioxo-9H-purin-8-yl)cinnamic Acid Heptaethylene Glycol Methyl Ether Ester Title compound was prepared from the title compound of Example 1 and heptaethylene glycol monomethyl ether (Heimann, U.; Voegtle, F. Liebigs Ann. Chem. 1980, 6, 858–862) using methods similar to those described in Example 1b and was obtained as a waxy solid (800 mg, 49% yield). $^1$H-NMR (400 MHz, DMSO-d$_6$) δ: 8.22 (d, J=8.2 Hz, 2H), 7.96 (d, J=8.2 Hz, 2H), 7.77 (d, J=16 Hz, 1H), 6.84 (d, J=16 Hz, 1H), 4.35 (t, J=5 Hz, 2H), 3.99 (d, J=7.3 Hz, 2H), 3.85 (d, J=7.2 Hz, 2H), 3.76 (t, J=5 Hz, 2H), 3.65–3.45 (m, 24H), 3.29 (s, 3H), 2.00 (m, 1H), 1.82 (m, 1H), 1.75–1.70 (m, 10H), 1.30–1.10 (m, 10H). MS (ES+): 813 (M+1).

(b) (E)-4-(1,3-bis(Cyclohexylmethyl)-2,3,6,7-tetrahydro-2,6-dioxo-7-methyl-1H-purin-8-yl)cinnamic Acid Heptaethylene Glycol Methyl Ether Ester Title compound was prepared from the title compound of Example 111a and methyl iodide using methods similar to those described in Example 77 and was obtained as an oil (35 mg, 10% yield). $^1$H-NMR (400 MHz, DMSO-d$_6$) δ: 7.72 (d, J=16 Hz, 1H), 7.71 (d, J=8.2 Hz, 2H), 7.64 (d, J=8.2 Hz, 2H), 6.54 (d, J=16 Hz, 1H), 4.37 (br t, J=5 Hz, 2H), 4.06 (s, 3H), 3.97 (d, J=7.3 Hz, 2H), 3.88 (d, J=7.2 Hz, 2H), 3.77 (t, J=5 Hz, 2H), 3.68–3.60 (m, 22H), 3.52 (m, 2H), 3.35 (s, 3H), 1.95 (m, 1H), 1.82 (m, 1H). 1.75–1.58 (m, 10H), 1.24–0.98 (m, 10H). MS (ES+): 827 (M+1).

Anal. Calcd For $C_{44}H_{66}N_4O_{11}$: C, 63.90; H, 8.04; N, 6.7. Found: C, 63.86; H, 8.00; N, 6.81.

The compounds named in Table 5, below, were prepared by methods similar to those described above for Example 111. (SM=starting material).

TABLE 5

| EX. | NAME | MASS SPEC/METHOD | ANALYTICAL | SM |
|-----|------|------------------|------------|-----|
| 112 | (E)-4-(1,3-Bis(cyclohexylmethyl)-2,3,6,7-tetrahydro-2,6-dioxo-7-methyl-1H-purin-8-yl)cinnamic Acid Methyl Ester | 519 (M + H)$^+$; FAB | Calcd for $C_{30}H_{38}N_4O_4$: 0.21 H$_2$O: C, 68.97; H, 7.32; N, 10.67; Found: C, 68.98; H, 7.32; N, 10.67 | Example 1 |
| 113 | (E)-4-(1,3-Bis(cyclohexylmethyl)-2,3,6,7-tetrahydro-2,6-dioxo-7-methyl-1H-purin-8-yl)cinnamic Acid Ethylene Glycol Methyl Ether Ester | 563 (M + H)$^+$; ES+ | Calcd for $C_{32}H_{42}N_4O_5$: C, 68.30; H, 7.52; N, 9.96; Found: C, 68.57; H, 7.59; N, 9.87 | Example 1 |
| 114 | (E)-4-(1,3-Bis(cyclohexylmethyl)-2,3,6,7-tetrahydro-2,6-dioxo-7-methyl-1H-purin-8-yl)cinnamic Acid Diethylene Glycol Methyl Ether Ester | 607 (M + H)$^+$; ES+ | Calcd for $C_{34}H_{46}N_4O_6$: C, 67.30; H, 7.64; N, 9.23; Found: C, 67.05; H, 7.62; N, 9.12 | Example 1 |
| 115 | (E)-4-(1,3-Bis(cyclohexylmethyl)-2,3,6,7-tetrahydro-2,6-dioxo-7-methyl-1H-purin-8-yl)cinnamic Acid Triethylene Glycol Methyl Ether Ester | 651 (M + H)$^+$; ES+ | Calcd for $C_{36}H_{50}N_4O_7$: C, 66.44; H, 7.74; N, 8.61; Found: C, 66.53; H, 7.72; N, 8.59 | Example 1 |
| 116 | (E)-4-(1,3-Bis(cyclohexylmethyl)-2,3,6,7-tetrahydro-2,6-dioxo-7-methyl-1H-purin-8-yl)cinnamic Acid Tetraethylene Glycol Methyl Ether Ester | 695 (M + H)$^+$; ES+ | Calcd for $C_{38}H_{54}N_4O_8$: C, 65.68; H, 7.83; N, 8.06; Found: C, 65.61; H, 7.88; N, 8.04 | Example 1 |
| 117 | (E)-4-(1,3-Bis(cyclohexylmethyl)-2,3,6,7-tetrahydro-2,6-dioxo-7-methyl-1H-purin-8-yl)cinnamic Acid Pentaethylene Glycol Methyl Ether Ester | 739 (M + H)$^+$; ES+ | Calcd for $C_{40}H_{58}N_4O_9$: C, 65.02; H, 7.91; N, 7.58; Found: C, 64.77; H, 8.00; N, 7.61 | Example 1 |

Example 118

4-[1,3-bis(Cyclohexylmethyl)-8-11-methoxy-3,6,9-trioxaundecyloxy)phenyl]-3,7-dihydro-1H-purine-2,6-dione

This compound was from 1,3-bis(cyclohexylmethyl)-5,6-diaminouracil and 4-(11-methoxy-3,6,9-trioxaundecyloxy) benzaldehyde using methods similar to those described in Example 109b and was obtained as a yellow solid (240 mg, 32% yield): $^1$H-NMR (400 MHz, CDCl$_3$) δ: 12.36 (br s, 1H), 8.14 (d, J=8.8 Hz, 2H), 7.01 (d, J=8.8 Hz, 2H), 4.18(t, J=5 Hz, 2H), 4.03(d, J=7.4 Hz, 2H), 3.96(d, J=7.4 Hz, 2H), 3.88 (t, J=5 Hz, 2H), 3.72 (m, 2H), 3.67 (m, 2H), 3.65 (m, 4H), 3.62 (m, 2H), 3.53 (m, 2H), 3.36 (s, 3H), 2.01 (m, 1H), 1.85 (m, 1H), 1.68–1.59 (m, 10H), 1.22–0.97 (m, 10H). MS (ES+): 627 (M+1).

Anal. Calcd for C$_{34}$H$_{50}$N$_4$O$_7$.(0.25.H$_2$O) C, 64.69; H, 8.06; N, 8.88; Found: C, 64.66; H, 7.92; N, 9.24.

Pharmaceutical Formulation Examples

In the following Examples, the "active ingredient" may be any compound of formula (I) or (Ia) or a pharmaceutically acceptable salt or solvate thereof preferably compound of Examples 34, 35, 36, 37, 40, 41, 42, 43,44, 45, 48, 49, 53, 54, 55, 57, 58, 59, 61, 63, 65, 67, 68, 69, 71, 75, 77, 78, 79, 80, 81, 82, 83, 84, 85, 86, 87, 88, 89, 91, 92, 93, 96, 98, 99, 100, 104, 107, 110.

(1) Tablet formulations

(i) Oral

| | mg/tablet | | |
|---|---|---|---|
| | A | B | C |
| Active ingredient | 25 | 25 | 25 |
| Avicel | 13 | — | 7 |
| Lactose | 78 | 47 | — |
| Starch (maize) | — | 9 | — |
| Starch (pregelatinised, NF15) | — | — | 32 |
| Sodium starch glycollate | 5 | — | — |
| Povidone | 3 | 3 | — |
| Magnesium stearate | 1 | 1 | 1 |
| | 125 | 85 | 65 |

(ii) Sublingual

| | mg/tablet | |
|---|---|---|
| | D | E |
| Active ingredient | 25 | 25 |
| Avicel | 10 | — |
| Lactose | — | 36 |
| Mannitol | 51 | 57 |
| Sucrose | — | 3 |
| Acacia | — | 3 |
| Povidone | 3 | — |
| Magnesium stearate | 1 | 1 |
| | 90 | 125 |

Formulations A to E may be prepared by wet granulation of the first six ingredients with the providone, followed by addition of the magnesium stearate and compression.

(iii) Buccal

| | mg/tablet |
|---|---|
| Active ingredient | 25 |
| Hydroxypropylmethyl cellulose (HPMC) | 25 |
| Polycarbophil | 39 |
| Magnesium stearate | 1 |
| | 90 |

The formulation may be prepared by direct compression of the admixed ingredients.

(2) Capsule formulations

(i) Powder

| | mg/Capsule | |
|---|---|---|
| | F | G |
| Active ingredient | 25 | 25 |
| Avicel | 45 | — |
| Lactose | 153 | — |
| Starch (1500 NF) | — | 117 |
| Sodium starch glycollate | — | 6 |
| Magnesium stearate | 2 | 2 |
| | 225 | 150 |

Formulations F and G may be prepared by admixing the ingredients and filling two-part hard gelatin capsules with the resulting mixture.

(ii) Liquid fill

| | mg/Capsule | |
|---|---|---|
| | H | I |
| Active ingredient | 25 | 25 |
| Macrogol 4000 BP | 200 | — |
| Lecithin | — | 100 |
| Arachis oil | — | 100 |
| | 225 | 225 |

Formulation H may be prepared by melting the Macrogol 4000 BP, dispersing the active ingredient in the melt and filling two-part hard gelatin capsules therewith. Formulation I may be prepared by dispersing the active ingredient in the lecithin and arachis oil and filling soft, elastic gelatin capsules with the dispersion.

(iii) Controlled release

| | mg/tablet |
|---|---|
| Active ingredient | 25 |
| Avicel | 123 |
| Lactose | 62 |
| Triethylcitrate | 3 |
| Ethyl cellulose | 12 |
| | 225 |

The formulation may be prepared by mixing and extruding the first four ingredients and spheronising and drying the extrudate. The dried pellets are coated with ethyl cellulose as a release controlling membrane and filled into two-part, hard gelatin capsules.

(3) Intravenous injection formulation (i)

| | % by weight |
|---|---|
| Active ingredients | 2% |
| Sodium hydroxide | q.s to pH 7 |
| Water for Injections | to 100% |

The active ingredient is taken up in the citrate buffer and sufficient hydrochloric acid added to affect solution and adjust the pH to 7. The resulting solution is made up to volume and filtered through a micropore filter into sterile glass vials which are sealed and oversealed.

(ii)

| | mg/mL | |
|---|---|---|
| | A | B |
| Active ingredients | 2.0 | 25.0 |
| Hydroxypropyl Beta Cyclodextrin | 200.0 | — |
| Soybean Oil | — | 200.0 |
| Phospholipids | — | 12.0 |
| Glycerin | — | 22.5 |
| Sodium hydroxide | q.s to pH 7 | — |
| Water for Injections | q.s. to 1.0 mL | q.s. to 1.0 mL |

Formulation A: The active ingredient is dissolved in a solution of hydroxypropyl beta cyclodextrin and adjusted the pH to 7. The resulting solution is made up to volume and filtered through a micropore filter into sterile glass vials, which are sealed and oversealed.

Formulation B: The active ingredient is dissolved in the soybean oil and phospholipids. The remaining ingredients are added and the solution is made up to volume. The resulting solution is then homogenized until the desired consistency is achieved.

Example G

Powder Capsules for Inhalation

| | |
|---|---|
| Active Ingredient (0.5–7.0 μm powder) | 1.0 mg |
| Lactose (30–90 μm powder) | 49.0 mg |

The powders were mixed until homogeneous and filled into suitably sized hard gelatin capsules (50 mg per capsule).

Example H

Inhalation Aerosol

| | |
|---|---|
| Active Ingredient (0.5–7.0 μm powder) | 50.0 mg |
| Sorbitan Trioleate | 100.00 mg |
| Saccharin Sodium (0.5–7.0 μm powder) | 5.0 mg |

-continued

| | |
|---|---|
| Methanol | 2.0 mg |
| Trichlorofluoromethane | 4.2 g |
| Dichlorodifluoromethane | to 10.0 ml |

The sorbitan trioleate and methanol were dissolved in the trichlorofluoromethane. The saccharin sodium and active ingredient were dispersed in the mixture which was then transferred to a suitable aerosol canister and the dichlorofluoromethane injected through the valve system. This composition provides 0.5 mg of active ingredient in each 100 μl dose.

Example I

Oral Suspension

| | mg/mL | | | |
|---|---|---|---|---|
| | A | B | C | D |
| Active ingredient | 25 | 25 | 25 | 25 |
| Sucrose | 200.0 | — | — | — |
| Sorbitol | — | 250.0 | — | — |
| Saccharin Sodium | — | 0.4 | 2.0 | 50 |
| Propylene Glycol | 20.0 | — | — | — |
| Polyethylene Glycol | — | 150.0 | — | — |
| Methylparaben | 1.5 | — | — | 1.5 |
| Propylparaben | 0.15 | — | — | 0.18 |
| Sodium Benzoate | — | 2.0 | — | — |
| Artificial Strawberry Flavor | 0.8 | — | 3.0 | — |
| Artificial Banana Flavor | 0.6 | — | — | — |
| Mint Flavor | — | 5.0 | — | 3.0 |
| HPMC | — | — | — | 4.5 |
| Xanthan Gum | — | — | 7.5 | — |
| Poloxamer 188 | — | — | 5.0 | — |
| Citric Acid | 1 | — | — | 5 |
| Sodium Hydroxide | to pH 6.0 | — | — | to pH 4.0 |
| Purified Water | to 1.0 mL | to 1.0 mL | to 1.0 mL | to 1.0 mL |

Formulation A: The parabens are dissolved in polypropyleneGlycol. The remaining inactive ingredients are dissolved in water and the polypropylene glycol solution of the parabens is added to the solution. The active ingredient is added and the resulting solution is mixed until the desired consistency is achieved. The pH is adjusted and the solution brought to final volume.

Formulation B: The sodium benzoate is dissolved in the polyethylene glycol. The remaining inactive ingredants are dissolved in water and the polyethylene glycol solution of the sodium benzoate is added to this solution. The active ingredient is added and the resulting solution is mixed until the desired consistency is achieved. The solution is then brought to final volume.

Formulation C and D: The in active ingredients are dissolved in water. The active is added and the resulting solution is mixed until the desired consistency is achieved. The pH is adjusted and the solution brought to final volume.

Biological Activity

1) Cell Adhesion Assay

The antiadhesion activity of compounds of the invention was determined using a modification of the previously described method, Jurgensen, C. H. et. al., J. Immunol. 1990, 44:653–661. The adhesiveness of cytokine-stimulated human umbilical vein endothelial cells was assessed by quantitating the adherence of fluorescently-labelled (calcein-AM, Molecular Probes, Eugene, Oreg.) leukocytes to endothelial cell monolayers. Activity was determined by calculating inhibition of cytokine-stimulated adhesion minus the basal adhesion (unstimulated).

Results
Cell Adhesion Assay

| Example | IC$_{50}$ (nm) |
|---|---|
| 38 | 150 ± 83 |
| 61 | 11 ± 4 |
| 36 | 11 ± 8 |
| 71 | 240 ± 200 |
| 35 | 29 ± 3 |
| 69 | 62 ± 27 |
| 68 | 72 ± 19 |
| 100 | 25 ± 8 |
| 67 | 2000 ± 820 |
| 40 | 14 ± 7 |
| 41 | 21 ± 12 |
| 66 | 230 ± 100 |
| 45 | 42 ± 24 |
| 48 | <0.1 |
| 49 | 13 ± 9 |
| 74 | 360 ± 160 |
| 44 | 20 ± 10 |
| 73 | >1000 |
| 56 | 160 ± 70 |
| 62 | 160 ± 85 |
| 105 | 200 ± 80 |
| 104 | 86 ± 54 |
| 103 | 230 ± 110 |
| 57 | 83 ± 41 |
| 63 | 55 ± 34 |
| 43 | 7.1 ± 2 |
| 72 | >2000 |
| 37 | 98 ± 33 |
| 60 | >1000 |
| 47 | 710 ± 410 |
| 42 | 12 ± 12 |
| 39 | 130 ± 80 |
| 34 | <0.1 |
| 70 | >1000 |
| 46 | 890 ± 420 |
| 58 | <0.1 |
| 53 | 39 ± 13 |
| 54 | 76 ± 28 |
| 51 | >2000 |
| 52 | 410 ± 60 |
| 64 | >1000 |
| 55 | 51 ± 45 |
| 65 | 48 ± 19 |
| 75 | 60 ± 25 |
| 76 | 350 ± 130 |
| 90 | 240 ± 140 |
| 98 | 37 ± 23 |
| 99 | 77 ± 29 |
| 79 | 3.0 ± 1.0 |
| 91 | 60 ± 29 |
| 111 | <0.1 |
| 83 | 28 ± 12 |
| 78 | 0.1 ± 0.09 |
| 77 | 9.6 ± 5.0 |
| 92 | 23 ± 12 |
| 80 | 10 ± 4 |
| 87 | 37 ± 13 |
| 81 | 16 ± 18 |
| 86 | 8.0 ± 3 |
| 84 | 7.0 ± 4 |
| 82 | 19 ± 16 |
| 89 | 38 ± 18 |
| 94 | 220 ± 87 |
| 88 | 49 ± 19 |
| 93 | 69 ± 97 |
| 50 | 270 ± 150 |
| 96 | 49 ± 16 |

Results
Cell Adhesion Assay

| Example | IC$_{50}$ (nm) |
|---|---|
| 110 | 29 ± 11 |
| 108 | 300 ± 82 |
| 106 | 110 ± 56 |
| 107 | 39 ± 19 |
| 101 | 340 ± 94 |
| 59 | 57 ± 24 |
| 95 | 1700 ± 690 |
| 97 | >1000 |

2) Carrageenan Pleurisy Assay

The antiinflammatory activity of compounds of the invention was determined by the procedure of Vinegar, R, et al., Proc. Soc. Exp. Biol. Med., 1981, 168, 24–32, using male Lewis rats of 150±20 grams. The carrageenan dose was 0.075 mg/rat. Pleural exudate was harvested four hours after injection of carrageenan. Acute antiinflammatory activity was determined by inhibition of pleural edema and inflammatory cells (neutrophils) from a negative (vehicle) control group.

Results
Carrageenan-Induced Pleurisy

| EXAMPLE | % Inhibition Cells | % Inhibition Exudate |
|---|---|---|
| 36 | 47 | 38 |
| 68 | 92 | 80 |
| 49 | 28 | 53 |
| 74 | 85 | 70 |
| 44 | 44 | 24 |
| 73 | 0 | 0 |
| 34 | 20 | 59 |
| 79 | 55 | 7 |

What is claimed is:

1. A method of treating periodontal disease, which comprises administering to a subject in need thereof a therapeutically effective amount of a compound of formula (Ib)

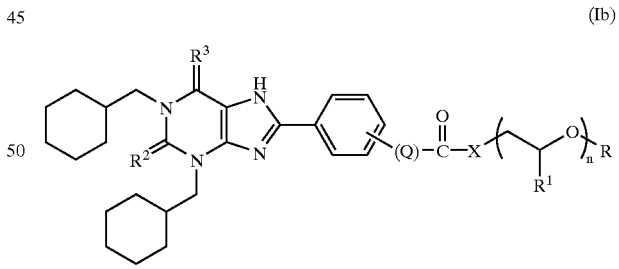

(Ib)

or a solvate thereof wherein:

X is —O— or —NH—.

Q is (—CH$_2$—)$_p$, (—CH=CH—)$_p$, (—C≡C—)$_p$ where p is an integer of from 0 to 4;

R$^1$ is hydrogen or methyl;

R$^2$ and R$^3$ independently represent O or S, n is an integer of 1 to 50; and

R is hydrogen or methyl.

2. A method of treating periodontal disease, which comprises administering to a subject in need thereof a therapeutically effective amount of a compound which is:

(E)-4-(1,3-Bis(cyclohexylmethyl)-1,2,3,6-tetrahydro-2,6-dioxo-9H-purin-8-yl)cinnamic Acid Decaethylene Glycol Methyl Ether Ester; and (E)-4-(1,3-Bis(cyclohexylmethyl)-1,2,3,6-tetrahydro-2,6-dioxo-9H-purin-8-yl)cinnamic Acid Nonaethylene Glycol Methyl Ether Ester;

(E)-3-[1,3-Bis(cyclohexylmethyl)-1,2,3,6-tetrahydro-2,6-dioxo-9H-purin-8-yl]cinnamic Acid Nonaethylene Glycol Methyl Ether Ester;

(E)-4-[1,3-Bis(cyclohexylmethyl)-1,2,3,6-tetrahydro-2,6-dioxo-9H-purin-8-yl]cinnamic acid Nonaethylene Glycol Methyl Ether Amide; or (E)-4-[1,3-Bis(cyclohexylmethyl)-1,2,3,6-tetrahydro-2,6-dioxo-9H-purin-8-yl]benzoic acid Nonaethylene Glycol Methyl Ether Ester.

3. A method of treating periodontal disease in a subject in need thereof which comprises administration of a therapeutically effective amount of (E)-4-(1,3-Bis(cyclohexylmethyl)-1,2,3,6-tetrahydro-2,6-dioxo-9H-purin-8-yl)cinnamic Acid Nonaethylene Glycol Methyl Ether Ester.

4. A method of treating periodontal disease, which comprises administering to a subject in need thereof a therapeutically effective amount of a compound of formula (I):

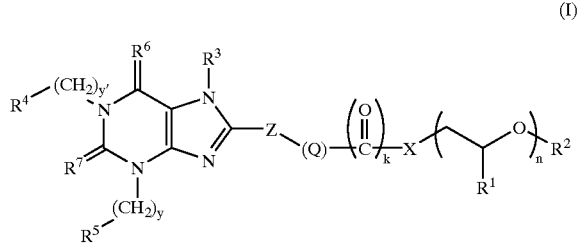

(I)

wherein

Z represents a 5 or 6 membered cycloalkyl, aryl, substituted cycloalkyl, substituted aryl, pyridine, thiophene or nicotine;

$R^1$ represents hydrogen or methyl;

$R^2$ represents hydrogen, $C_{1-12}$alkyl, aryl, or aralkyl;

k represents 0 or 1;

n represents an integer of 1–50;

X represents —O—, —N(H)—, —N($C_{1-6}$alkyl)—, —N($C_{3-8}$cycloalkyl)—, —N($C_{1-8}$alkyl)($C_{3-8}$cycloalkyl), —N[($CH_2CH_2O)_m$($C_{1-12}$alkyl, aryl, or aralkyl)]—, —$CH_2$O—, —$CH_2$NH—, —$CH_2$N($C_{1-8}$alkyl)—, —$CH_2$N($C_{3-8}$cycloalkyl)—, or —$C_{1-12}$alkylene-;

m represents 0–12;

Q represents (—$CH_2$—)$_p$, (—CH=CH—)$_p$, (—C≡C—)$_p$, (—O)$_{p1}$CH$_2$—)$_p$ or (—$CH_2$(O)$_{p1}$)$_p$ where p is an integer of from 0 to 4 and p1 is 0;

y and y' independently represent integers from 0 to 10;

$R^3$ represents H, straight or branched $C_{1-12}$alkyl (optionally substituted by phenyl, —CO-phenyl, CN, —CO($C_{1-3}$)alkyl, —$CO_2$($C_{1-3}$)alkyl, or containing one or more O atoms in the alkyl chain); $C_{2-6}$straight or branched alkenyl, $C_{2-6}$straight or branched alkynyl or a group —$C_{1-3}$alkylene-NR$^8$R$^9$;

wherein $R^8$ and $R^9$ are independently H, $C_{1-3}$alkyl or together form a 5 or 6 membered heterocyclic group, optionally containing other heteroatoms selected from O, N or S;

$R^4$ and $R^5$ independently represent
$C_{3-8}$cycloalkyl
straight chain or branched $C_{1-6}$alkyl
hydrogen
straight chain or branched $C_{2-6}$alkenyl
aryl or substituted aryl;
heterocyclic group, substituted heterocyclic group, heteroaryl group or substituted heteroaryl group;

$R^6$ and $R^7$ independently represent O or S;

or a solvate thereof.

5. A method of treating periodontal disease, which comprises administering to a subject in need thereof a therapeutically effective amount of a compound of formula (Ia):

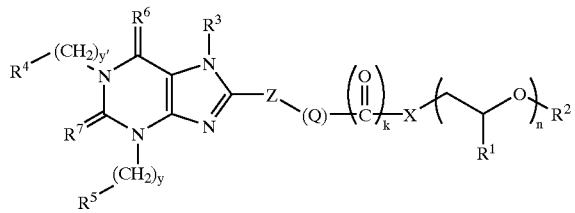

(Ia)

wherein

Z represents a 5 or 6 membered cycloalkyl, aryl, substituted cycloalkyl, substituted aryl, pyridine, thiophene or nicotine;

$R^1$ represents hydrogen or methyl;

$R^2$ represents hydrogen, $C_{1-12}$alkyl, aryl, or aralkyl;

k represents 0 or 1;

n represents an integer of 1–50;

X represents —O—, —N(H)—, —N($C_{1-6}$alkyl)—, —N($C_{3-8}$cycloalkyl)—, —N(($CH_2CH_2O)_m$($C_{1-12}$alkyl, aryl, or aralkyl)]—, —$CH_2$O—, —$CH_2$NH—, —$CH_2$N($C_{1-6}$alkyl)—, —$CH_2$N($C_{3-8}$cycloalkyl)—, or —$C_{1-12}$alkylene-;

m represents 0–12;

Q represents (—$CH_2$—)$_p$, (—CH=CH—)$_p$, (—C≡C—)$_p$, (—O)$_{p1}$CH2—)$_p$ or (—$CH_2$(O)$_{p1}$)$_p$ where p is an integer of from 0 to 4 and p1 is 0;

y and y' independently represent integers from 0 to 10;

$R^3$ represents H, straight chain or branched $C_{1-12}$alkyl (optionally substituted by phenyl, —CO-phenyl, CN, —CO($C_{1-3}$)alkyl, —$CO_2$($C_{1-3}$)alkyl, or containing one or more O atoms in the alkyl chain); $C_{1-6}$straight or branched alkenyl, $C_{1-6}$straight or branched alkynyl or a group —$C_{1-3}$alkylene-NR$^8$R$^9$;

wherein $R^8$ and $R^9$ are independently H, $C_{1-3}$alkyl or together form a 5 or 6 membered heterocyclic group, optionally containing other heteroatoms selected from O, N or S;

$R^4$ and $R^5$ independently represent
—$C_{3-8}$cycloalkyl
straight chain or branched $C_{1-6}$alkyl
hydrogen
straight chain or branched $C_{2-6}$alkenyl
aryl or substituted aryl, or
heterocyclic group, substituted heterocyclic group, heteroaryl group or substituted heteroaryl group;

$R^6$ and $R^7$ independently represent O or S;

or a solvate thereof.

6. A method of treating periodontal disease, which comprises administering to a subject in need thereof a therapeutically effective amount of a compound selected from the group consisting of:

(E)-4-(1,3-bis(benzyl)-1,2,3,6-tetrahydro-2,6-dioxo-9H-purin-8-yl)cinnamic Acid Nonaethylene Glycol Methyl Ether Ester;

(E)-4-[1,3-Bis(cyclohexylmethyl)-1,2,3,6-tetrahydro-2,6-dioxo-9H-purin-8-yl]cinnamic Acid Nonaethylene Glycol Methyl Ether Ester;

(E)-4-(1,3-bis(cyclopentylmethyl)-1,2,3,6-tetrahydro-2,6-dioxo-9H-purin-8-yl)cinnamic Acid Nonaethylene Glycol Methyl Ether Ester;

(E)-4-(1,3-bis(propyl)-1,2,3,6-tetrahydro-2,6-dioxo-9H-purin-8-yl)cinnamic Acid Nonaethylene Glycol Methyl Ether Ester;

(E)-4-(1,3-bis(cyclopropylmethyl)-1,2,3,6-tetrahydro-2,6-dioxo-9H-purin-8-yl)cinnamic Acid Nonaethylene Glycol Methyl Ether Ester;

(E)-3-((1-propyl-3-benzyl)-1,2,3,6-tetrahydro-2,6-dioxo-9H-purin-8-yl)cinnamic Acid Nonaethylene Glycol Methyl Ether Ester;

(E)-4-(1,3-bis(cycloheptylmethyl)-1,2,3,6-tetrahydro-2,6-dioxo-9H-purin-8-yl)cinnamic Acid Nonaethylene Glycol Methyl Ether Ester;

(E)-4-(1,3-bis(cyclohexylethyl)-1,2,3,6-tetrahydro-2,6-dioxo-9H-purin-8-yl)cinnamic Acid Nonaethylene Glycol Methyl Ether Ester;

(E)-4-(1,3-bis(phenyl)-1,2,3,6-tetrahydro-2,6-dioxo-9H-purin-8-yl)cinnamic Acid Nonaethylene Glycol Methyl Ether Ester;

(E)-4-(1,3-bis(2-methyl-propyl)-1,2,3,6-tetrahydro-2,6-dioxo-9H-purin-8-yl)cinnamic Acid Nonaethylene Glycol Methyl Ether Ester;

(E)-4-((1-propyl-3-cyclohexylmethyl)-1,2,3,6-tetrahydro-2,6-dioxo-9H-purin-8-yl)cinnamic Acid Nonaethylene Glycol Methyl Ether Ester;

(E)-4-(1,3-bis(bicyclo(2.2.1)hept-2-ylmethyl)-1,2,3,6-tetrahydro-2,6-dioxo-9H-purin-8-yl)cinnamic Acid Nonaethylene Glycol Methyl Ether Ester;

(E)-4-(1-cyclohexylmethyl-3-butyl)-1,2,3,6-tetrahydro-2,6-dioxo-9H-purin-8-yl)cinnamic Acid Nonaethylene Glycol Methyl Ether Ester;

(E)-4-([1-cyclohexylmethyl-3-propyl)-1,2,3,6-tetrahydro-2,6-dioxo-9H-purin-8-yl]cinnamic Acid Nonaethylene Glycol Methyl Ether Ester;

(E)4-(1,3-bis(benzyl)-1,2,3,6-tetrahydro-2-thioxo-6-oxo-9H-purin-8-yl)cinnamic Acid Nonaethylene Glycol Methyl Ether Ester;

(E)-4-(1-methyl-3-(3-cyanobenzyl))-1,2,3,6-tetrahydro-2,6-dioxo-9H-purin-8-yl)cinnamic Acid Nonaethylene Glycol Methyl Ether Ester;

(E)-4-((1,3-bis(3-fluorobenzyl)-1,2,3,6-tetrahydro-2,6-dioxo-9H-purin-8-yl)cinnamic Acid Nonaethylene Glycol Methyl Ether Ester;

(E)-4-((1,3-bis[2-fluorobenzyl]-1,2,3,6-tetrahydro-2,6-dioxo-9H-purin-8-yl)cinnamic Acid Nonaethylene Glycol Methyl Ether Ester;

(E)-4-((1,3-bisphenethyl)-1,2,3,6-tetrahydro-2,6-dioxo-9H-purin-8-yl)cinnamic Acid Nonaethylene Glycol Methyl Ether Ester;

(E)-4-((1-cyclohexylmethyl-3-methyl)-1,2,3,6-tetrahydro-2,6-dioxo-9H-purin-8-yl)cinnamic Acid Nonaethylene Glycol Methyl Ether Ester;

(E)-4-((1-H-3-(2-methyl-propyl)-1,2,3,6-tetrahydro-2,6-dioxo-9H-purin-8-yl)cinnamic Acid Nonaethylene Glycol Methyl Ether Ester;

(E)-4-[1,3-bis(4-fluorobenzyl)-1,2,3,6-tetrahydro-2,6-dioxo-9H-purin-8-yl]cinnamic Acid Nonaethylene Glycol Methyl Ether Ester;

(E)-4-(1,3-bis(cyclohexylmethyl)-1,2,3,6-tetrahydro-2,6-dioxo-9H-purin-8-yl)cinnamic Acid Hexaethylene Glycol dodecyl Ether Ester;

(E)-4-(1,3-bis(cyclobutylmethyl)-1,2,3,6-tetrahydro-2,6-dioxo-9H-purin-8-yl)cinnamic Acid Nonaethylene Glycol Methyl Ether Ester;

(E)-4-(1-methyl-3-cyclohexylmethyl)-1,2,3,6-tetrahydro-2,6-dioxo-9H-purin-8-yl)cinnamic Acid Nonaethylene Glycol Methyl Ether Ester;

(E)-4-(1-methyl-3-isobutyl)-1,2,3,6-tetrahydro-2,6-dioxo-9H-purin-8-yl)cinnamic Acid Nonaethylene Glycol Methyl Ether Ester;

4-[1,3-bis(cyclohexylmethyl]-1,2,3,6-tetrahydro-2,6-dioxo-9H-purin-8-yl)benzoic Acid Nonaethylene Glycol Methyl Ether Ester;

(E)-4-[1,3-bis(cyclohexyl]-1,2,3,6-tetrahydro-2,6-dioxo-9H-purin-8-yl)cinnamic Acid Nonaethylene Glycol Methyl Ether Ester;

(E)-4-(1,3-Bis(cyclohexylmethyl)-1,2,3,6-tetrahydro-2,6-dioxo-9H-purin-8-yl)cinnamic Acid Nonaethylene Glycol Methyl Ether Amide;

(E)-4-(1,3-bis(cyclopentylmethyl)-1,2,3,6-tetrahydro-6-oxo-2-thioxo-9H-purin-8-yl)cinnamic Acid Nonaethylene Glycol Methyl Ether Amide;

(E)-4-(1,3-bis(2-methyl-propyl)-1,2,3,6-tetrahydro-2,6-dioxo-9H-purin-8-yl)cinnamic Acid Nonaethylene Glycol Methyl Ether Amide;

(E)-4-((1-cyclohexylmethyl-3-propyl)-1,2,3,6-tetrahydro-2,6-dioxo-9H-purin-8-yl)cinnamic Acid Nonaethylene Glycol Methyl Ether Amide;

4-(1,3-Bis(cyclohexylmethyl)-1,2,3,6-tetrahydro-2,6-dioxo-9H-purin-8-yl)benzoic Acid Nonaethylene Glycol Methyl Ether Amide;

4-(1,3-Bis(cyclohexylmethyl)-1,2,3,6-tetrahydro-2,6-dioxo-9H-purin-8-yl)benzoic Acid-N-methyl-Nonaethylene Glycol Methyl Ether Amide;

(E)-4-(1,3-Bis(cyclohexylmethyl)-2,3,6,7-tetrahydro-2,6-dioxo-7-benzyl-1H-purin-8-yl)cinnamic Acid Nonaethylene Glycol Methyl Ether Ester;

(E)-4-(1,3-Bis(cyclohexylmethyl)-2,3,6,7-tetrahydro-2,6-dioxo-7-[2-oxo-2-phenylethyl)-1H-purin-8-yl) cinnamic Acid Nonaethylene Glycol Methyl Ether Ester;

(E)-4-(1,3-Bis(cyclohexylmethyl)-2,3,6,7-tetrahydro-2,6-dioxo-7-methyl-1H-purin-8-yl)cinnamic Acid Nonaethylene Glycol Methyl Ether Ester;

(E)-4-(1,3-Bis(cyclohexylmethyl)-2,3,6,7-tetrahydro-2,6-dioxo-7-(2-propynyl)-1H-purin-8-yl)cinnamic Acid Nonaethylene Glycol Methyl Ether Ester;

(E)-4-(1,3-Bis(cyclohexylmethyl)-2,3,6,7-tetrahydro-2,6-dioxo-7-(2-oxo-2-methylethyl)-1H-purin-8-yl) cinnamic Acid Nonaethylene Glycol Methyl Ether Ester;

(E)-4-(1,3-Bis(cyclohexylmethyl)-2,3,6,7-tetrahydro-2,6-dioxo-7-(3-morpholinopropyl)-1H-purin-8-yl) cinnamic Acid Nonaethylene Glycol Methyl Ether Ester;

(E)-4-(1,3-Bis(cyclohexylmethyl)-2,3,6,7-tetrahydro-2,6-dioxo-7-ethyl-1H-purin-8-yl)cinnamic Acid Nonaethylene Glycol Methyl Ether Ester;

(E)-4-1,3-Bis(cyclohexylmethyl)-2,3,6,7-tetrahydro-2,6-dioxo-7-(2-ethoxy-2-oxoethyl)-1H-purin-8-yl) cinnamic Acid Nonaethylene Glycol Methyl Ether Ester;

(E)-4-(1,3-Bis(cyclohexylmethyl)-2,3,6,7-tetrahydro-2,6-dioxo-7-(2-methyl-2-propenyl)-1H-purin-8-yl)cinnamic Acid Nonaethylene Glycol Methyl Ether Ester;

(E)-4-(1,3-Bis(cyclohexylmethyl)-2,3,6,7-tetrahydro-2,6-dioxo-7-(cyanomethyl)-1H-purin-8-yl)cinnamic Acid Nonaethylene Glycol Methyl Ether Ester;

4-(1,3-Bis(cyclohexylmethyl)-2,3,6,7-tetrahydro-2,6-dioxo-7-benzyl-1H-purin-8-yl)benzoic Acid Nonaethylene Glycol Methyl Ether Ester;

4-(1,3-Bis(cyclohexylmethyl)-2,3,6,7-tetrahydro-2,6-dioxo-7-methyl-1H-purin-8-yl)benzoic Acid Nonaethylene Glycol Methyl Ether Ester;

4-[(1,3-Bis(cyclohexylmethyl)-2,3,6,7-tetrahydro-2,6-dioxo-7-methyl-1H-purin-8-yl)phenyl]propionic Acid Nonaethylene Glycol Methyl Ether Ester;

(E)-4-(1,3-Bis(cyclohexylmethyl)-2,3,6,7-tetrahydro-2,6-dioxo-7-methyl-1H-purin-8-yl)cinnamic Acid Nonaethylene Glycol Methyl Ether Amide;

(E)-4-(1,3-Bis(cyclohexylmethyl)-2,3,6,7-tetrahydro-2,6-dioxo-7-benzyl-1H-purin-8-yl)cinnamic Acid Nonaethylene Glycol Methyl Ether Amide;

4-(1,3-Bis(cyclohexylmethyl)-2,3,6,7-tetrahydro-2,6-dioxo-7-benzyl-1H-purin-8-yl)benzoic Acid Nonaethylene Glycol Methyl Ether Amide;

4-(1,3-Bis(cyclohexylmethyl)-2,3,6,7-tetrahydro-2,6-dioxo-7-methyl-1H-purin-8-yl)benzoic Acid Nonaethylene Glycol Methyl Ether Amide;

1,3-Bis(cyclohexylmethyl)-8-[4-(2,5,8,11,14,17,20,23,26,29-decaoxatriacont-1-yl)phenyl]-3,7-dihydro-1H-purine-2,6-dione;

(E)-3-[5-[1,3-bis(cyclohexylmethyl)-2,3,6,7-tetrahydro-2,6-dioxo-1H-purin-8-yl]-2-thienyl]-2-propenoic Acid Nonaethylene Glycol Methyl Ether Ester;

6-(1,3-Bis(cyclohexylmethyl)-1,2,3,6-tetrahydro-2,6-dioxo-9H-purin-8-yl)nicotinic Acid Nonaethylene Glycol Methyl Ether Amide;

(E)-3-(1,3-Bis(cyclohexylmethyl)-1,2,3,6-tetrahydro-2,6-dioxo-9H-purin-8-yl)cinnamic Acid N-cyclopropylmethyl Nonaethylene Glycol Methyl Ether Amide;

(E)-4-(1,3-Bis(cyclohexylmethyl)-1,2,3,6-tetrahydro-2,6-dioxo-9H-purin-8-yl)cinnamic Acid Hexaethylene Glycol Benzyl Ether Amide;

(E)-4-[(3-Cyclohexylmethyl)-2,3,6,7-tetrahydro-2,6-dioxo-7-methyl-1H-purin-8-yl)cinnamic Acid Heptaethylene Glycol Methyl Ether Ester;

(E)-4-[(3-Cyclohexylmethyl)-2,3,6,7-tetrahydro-2,6-dioxo-7-methyl-1H-purin-8-yl]cinnamic Acid Nonaethylene Glycol Methyl Ether Ester;

(E)-4-[(3-Cyclohexylmethyl)-2,3,6,7-tetrahydro-2,6-dioxo-1,7-dimethyl-1H-purin-8-yl]cinnamic Acid Nonaethylene Glycol Methyl Ether Ester;

4-[1,3-Bis(cyclohexylmethyl)-1,2,3,6-tetrahydro-2,6-dioxo-9H-purin-8-yl]benzylamine Heptaethylene Glycol Methyl Ether;

4-[1,3-Bis(cyclohexylmethyl)-1,2,3,6-tetrahydro-2,6-dioxo-9H-purin-8-yl]benzylamine N-Heptaethylene Glycol Methyl Ether Hydrochloride;

4-[1,3-Bis(cyclohexylmethyl)-1,2,3,6-tetrahydro-2,6-dioxo-9H-purin-8-yl]benzylamine N-Nonaethylene Glycol Methyl Ether;

1,3-Bis(cyclohexylmethyl)-8-[3-(2,5,8,11,14,17,20,23,26,29-decaoxatriacont-1-yl)phenyl]-3,7-dihydro-1H-purine-2,6-dione;

(E)-4-(1,3-Bis(cyclohexylmethyl)-2,3,6,7-tetrahydro-2,6-dioxo-7-methyl-1H-purin-8-yl)cinnamic Acid Heptaethylene Glycol Methyl Ether Ester;

(E)-(1,3-Bis(cyclohexylmethyl)-2,3,6,7-tetrahydro-2,6-dioxo-7-methyl-1H-purin-8-yl]cinnamic Acid Pentaethylene Glycol Methyl Ether Ester; and (E)-4-(1,3-Bis(cyclohexylmethyl)-2,3,6,7-tetrahydro-2,6-dioxo-7-propyl-1H-purin-8-yl)cinnamic Acid Nonaethylene Glycol Methyl Ether Ester.

7. A method of treating periodontal disease, which comprises administering to a subject in need thereof a therapeutically effective amount of a compound selected from the group consisting of:

(E)-4-(1,3-bis(benzyl)-1,2,3,6-tetrahydro-2,6-dioxo-9H-purin-8-yl)cinnamic Acid Nonaethylene Glycol Methyl Ether Ester;

(E)-4-[1,3-Bis(cyclohexylmethyl)-1,2,3,6-tetrahydro-2,6-dioxo-9H-purin-8-yl]cinnamic Acid Nonaethylene Glycol Methyl Ether Ester;

(E)-4-(1,3-bis(cyclopentylmethyl)-1,2,3,6-tetrahydro-2,6-dioxo-9H-purin-8-yl)cinnamic Acid Nonaethylene Glycol Methyl Ether Ester;

(E)-4-(1,3-bis(propyl)-1,2,3,6-tetrahydro-2,6-dioxo-9H-purin-8-yl)cinnamic Acid Nonaethylene Glycol Methyl Ether Ester;

(E)-4-(1,3-bis(cycloheptylmethyl)-1,2,3,6-tetrahydro-2,6-dioxo-9H-purin-8-yl)cinnamic Acid Nonaethylene Glycol Methyl Ether Ester;

(E)-(1,3-bis(cyclohexylethyl)-1,2,3,6-tetrahydro-2,6-dioxo-9H-purin-8-yl)cinnamic Acid Nonaethylene Glycol Methyl Ether Ester;

(E)-4-(1,3-bis(phenyl)-1,2,3,6-tetrahydro-2,6-dioxo-9H-purin-8-yl)cinnamic Acid Nonaethylene Glycol Methyl Ether Ester;

(E)-4-(1,3-bis(2-methyl-propyl)-1,2,3,6-tetrahydro-2,6-dioxo-9H-purin-8yl)cinnamic Acid Nonaethylene Glycol Methyl Ether Ester;

(E)-4-((1-propyl-3-cyclohexylmethyl)-1,2,3,6-tetrahydro-2,6-dioxo-9H-purin-8-yl)cinnamic Acid Nonaethylene Glycol Methyl Ether Ester;

(E)-4-(1,3-bis(bicyclo(2.2.1)hept-2-ylmethyl)-1,2,3,6-tetrahydro-2,6-dioxo-9H-purin-8-yl)cinnamic Acid Nonaethylene Glycol Methyl Ether Ester;

(E)-4-(1-cyclohexylmethyl-3-butyl)-1,2,3,6-tetrahydro-2,6-dioxo-9H-purin-8-yl)cinnamic Acid Nonaethylene Glycol Methyl Ether Ester;

(E)-4-((1-cyclohexylmethyl-3-propyl)-1,2,3,6-tetrahydro-2,6-dioxo-9H-purin-8-yl)cinnamic Acid Nonaethylene Glycol Methyl Ether Ester;

(E)-4-((1,3-bis(3-fluorobenzyl)-1,2,3,6-tetrahydro-2,6-dioxo-9H-purin-8-yl)cinnamic Acid Nonaethylene Glycol Methyl Ether Ester;

(E)-4-((1,3-bis(2-fluorobenzyl)-1,2,3,6-tetrahydro-2,6-dioxo-9H-purin-8-yl)cinnamic Acid Nonaethylene Glycol Methyl Ether Ester;

(E)-4-((1,3-bisphenethyl)-1,2,3,6-tetrahydro-2,6-dioxo-9H-purin-8-yl)cinnamic Acid Nonaethylene Glycol Methyl Ether Ester;

(E)-4-((1-H-3-(2-methyl-propyl)-1,2,3,6-tetrahydro-2,6-dioxo-9H-purin-8-yl)cinnamic Acid Nonaethylene Glycol Methyl Ether Ester;

(E)-4-(1,3-bis(4-fluorobenzyl)-1,2,3,6-tetrahydro-2,6-dioxo-9H-purin-8-yl)cinnamic Acid Nonaethylene Glycol Methyl Ether Ester;

(E)-4-(1,3-bis(cyclohexylmethyl)-1,2,3,6-tetrahydro-2,6-dioxo-9H-purin-8-yl)cinnamic Acid Hexaethylene Glycol dodecyl Ether Ester;

(E)-4-(1,3-bis(cyclobutylmethyl)-1,2,3,6-tetrahydro-2,6-dioxo-9H-purin-8-yl)cinnamic Acid Nonaethylene Glycol Methyl Ether Ester;

(E)-4-(1-methyl-3-isobutyl)-1,2,3,6-tetrahydro-2,6-dioxo-9H-purin-8-yl)cinnamic Acid Nonaethylene Glycol Methyl Ether Ester;

4-(1,3-bis(cyclohexylmethyl)-1,2,3,6-tetrahydro-2,6-dioxo-9H-purin-8-yl)benzoic Acid Nonaethylene Glycol Methyl Ether Ester;

(E)-3-(1,3-bis(cyclohexylmethyl)-1,2,3,6-tetrahydro-2,6-dioxo-9H-purin-8-yl)cinnamic Acid Nonaethylene Glycol Methyl Ether Amide;

(E)-4-(1,3-Bis(cyclohexylmethyl)-1,2,3,6-tetrahydro-2,6-dioxo-9H-purin-8-yl)cinnamic Acid-N-methyl Nonaethylene Glycol Methyl Ether Amide;

(E)-4-(1,3-Bis(cyclohexylmethyl)-1,2,3,6-tetrahydro-2,6-dioxo-9H-purin-8-yl)cinnamic Acid Nonaethylene Glycol Methyl Ether Amide;

4-(1,3-Bis(cyclohexylmethyl)-1,2,3,6-tetrahydro-2,6-dioxo-9H-purin-8-yl)benzoic Acid Nonaethylene Glycol Methyl Ether Amide;

(E)-4-(1,3-Bis(cyclohexylmethyl)-2,3,6,7-tetrahydro-2,6-dioxo-7-benzyl-1H-purin-8-yl)cinnamic Acid Nonaethylene Glycol Methyl Ether Ester;

(E)-4-(1,3-Bis(cyclohexylmethyl)-2,3,6,7-tetrahydro-2,6-dioxo-7-(2-oxo-2-phenylethyl)-1H-purin-8-yl)cinnamic Acid Nonaethylene Glycol Methyl Ether Ester;

(E)-4-(1,3-Bis(cyclohexylmethyl)-2,3,6,7-tetrahydro-2,6-dioxo-7-methyl-1H-purin-8-yl)cinnamic Acid Nonaethylene Glycol Methyl Ether Ester;

(E)-4-(1,3-Bis(cyclohexylmethyl)-2,3,6,7-tetrahydro-2,6-dioxo-7-(2-propynyl)-1H-purin-8-yl)cinnamic Acid Nonaethylene Glycol Methyl Ether Ester;

(E)-4-(1,3-Bis(cyclohexylmethyl)-2,3,6,7-tetrahydro-2,6-dioxo-7-(2-oxo-2-methylethyl)-1H-purin-8-yl)cinnamic Acid Nonaethylene Glycol Methyl Ether Ester;

(E)-4-(1,3-Bis(cyclohexylmethyl)-2,3,6,77-tetrahydro-2,6-dioxo-7-(3-morpholinopropyl)-1H-purin-8-yl)cinnamic Acid Nonaethylene Glycol Methyl Ether Ester;

(E)-4-(1,3-Bis(cyclohexylmethyl)-2,3,6,7-tetrahydro-2,6-dioxo-7-ethyl-1H-purin-8-yl)cinnamic Acid Nonaethylene Glycol Methyl Ether Ester;

(E)-(1,3-Bis(cyclohexylmethyl)-2,3,6,7-tetrahydro-2,6-dioxo-7-(2-ethoxy-2-oxoethyl)-1H-purin-8-yl)cinnamic Acid Nonaethylene Glycol Methyl Ether Ester;

(E)-4-(1,3-Bis(cyclohexylmethyl)-2,3,6,7-tetrahydro-2,6-dioxo-7-(2-methyl-2-propenyl)-1H-purin-8-yl)cinnamic Acid Nonaethylene Glycol Methyl Ether Ester;

(E)-4-(1,3-Bis(cyclohexylmethyl)-2,3,6,7-tetrahydro-2,6-dioxo-7-(cyanomethyl)-1H-purin-8-yl)cinnamic Acid Nonaethylene Glycol Methyl Ether Ester;

4-(1,3-Bis(cyclohexylmethyl)-2,3,6,7-tetrahydro-2,6-dioxo-7-benzyl-1H-purin-8-yl)benzoic Acid Nonaethylene Glycol Methyl Ether Ester;

4-(1,3-Bis(cyclohexylmethyl)-2,3,6,7-tetrahydro-2,6-dioxo-7-methyl-1H-purin-8-yl)benzoic Acid Nornaethylene Glycol Methyl Ether Ester;

(E)-4-(1,3-Bis(cyclohexylmethyl)-2,3,6,7-tetrahydro-2,6-dioxo-7-methyl-1H-purin-8-yl)cinnamic Acid Nonaethylene Glycol Methyl Ether Amide;

(E)-4-(1,3-Bis(cyclohexylmethyl)-2,3,6,7-tetrahydro-2,6-dioxo-7-benzyl-1H-purin-8-yl)cinnamic Acid Nonaethylene Glycol Methyl Ether Amide;

4-(1,3-Bis(cyclohexylmethyl)-2,3,6,7-tetrahydro-2,6-dioxo-7-benzyl-1H-purin-8-yl)benzoic Acid Nonaethylene Glycol Methyl Ether Amide;

1,3-Bis(cyclohexylmethyl)-8-[4-(2,5,8,11,14,17,20,23,26,29-decaoxatriacont-1-yl)phenyl]-3,7-dihydro-1H-purine-2,6-dione;

(E)-3-[5-[1,3-bis(cyclohexylmethyl)-2,3,6,7-tetrahydro-2,6-dioxo-1H-purin-8-yl]-2-thienyl]-2-propenoic Acid Nonaethylene Glycol Methyl Ether Ester;

6-(1,3-Bis(cyclohexylmethyl)-1,2,3,6-tetrahydro-2,6-dioxo-9H-purin-8-yl)nicotinic Acid Nonaethylene Glycol Methyl Ether Amide;

(E)-3-(1,3-Bis(cyclohexylmethyl)-1,2,3,6-tetrahydro-2,6-dioxo-9H-purin-8-yl)cinnamic Acid N-cyclopropylmethyl Nonaethylene Glycol Methyl Ether Amide;

(E)-4-[(3-Cyclohexylmethyl)-2,3,6,7-tetrahydro-2,6-dioxo-7-methyl-1H-purin-8-yl]cinnamic Acid Nonaethylene Glycol Methyl Ether Ester;

4-[1,3-Bis(cyclohexylmethyl)-1,2,3,6-tetrahydro-2,6-dioxo-9H-purin-8-yl]benzylamine N-Heptaethylene Glycol Methyl Ether Hydrochloride;

1,3-Bis(cyclohexylmethyl)-8-[3-(2,5,8,11,14,17,20,23,26,29-decaoxatriacont-1-yl)phenyl]-3,7-dihydro-1H-purine-2,6-dione;

(E)-4-(1,3-bis(cyclopentylmethyl)-1,2,3,6-tetrahydro-6-oxo-2-thioxo-9H-purin-8-yl)cinnamic Acid Nonaethylene Glycol Methyl Ether Amide; and (E)-4-(1,3-Bis(cyclohexylmethyl)-2,3,6,7-tetrahydro-2,6-dioxo-7-propyl-1H-purin-8-yl)cinnamic Acid Nonaethylene Glycol Methyl Ether Ester.

\* \* \* \* \*